US012378208B2

(12) United States Patent
Ma et al.

(10) Patent No.: US 12,378,208 B2
(45) Date of Patent: Aug. 5, 2025

(54) N-SUBSTITUTED OSELTAMIVIR DERIVATIVES WITH ANTIMICROBIAL ACTIVITY

(71) Applicants: THE HONG KONG POLYTECHNIC UNIVERSITY, Hong Kong (CN); The Chinese University of Hong Kong, Hong Kong (CN)

(72) Inventors: Cong Ma, Hong Kong (CN); Xiao Yang, Hong Kong (CN); Jiqing Ye, Hong Kong (CN); Paul Kay-Sheung Chan, Hong Kong (CN); Wan Yi Chan, Hong Kong (CN)

(73) Assignees: The Hong Kong Polytechnic University, Hong Kong (CN); The Chinese University of Hong Kong, Hong Kong (CN)

( * ) Notice: Subject to any disclaimer, the term of this patent is extended or adjusted under 35 U.S.C. 154(b) by 824 days.

(21) Appl. No.: 17/596,207

(22) PCT Filed: Jun. 23, 2020

(86) PCT No.: PCT/CN2020/097602
§ 371 (c)(1),
(2) Date: Dec. 6, 2021

(87) PCT Pub. No.: WO2020/259471
PCT Pub. Date: Dec. 30, 2020

(65) Prior Publication Data

US 2022/0306592 A1 Sep. 29, 2022

Related U.S. Application Data

(60) Provisional application No. 62/865,347, filed on Jun. 24, 2019.

(51) Int. Cl.

| | |
|---|---|
| *C07D 271/06* | (2006.01) |
| *A61K 31/341* | (2006.01) |
| *A61K 31/415* | (2006.01) |
| *A61K 31/42* | (2006.01) |
| *A61P 31/16* | (2006.01) |
| *C07D 261/08* | (2006.01) |
| *C07D 307/52* | (2006.01) |

(52) U.S. Cl.
CPC .......... *C07D 271/06* (2013.01); *A61K 31/341* (2013.01); *A61K 31/415* (2013.01); *A61K 31/42* (2013.01); *A61P 31/16* (2018.01); *C07D 261/08* (2013.01); *C07D 307/52* (2013.01)

(58) Field of Classification Search

CPC ............................ C07D 271/06; A61K 31/341

See application file for complete search history.

(56) References Cited

FOREIGN PATENT DOCUMENTS

| | | |
|---|---|---|
| CN | 103923060 A | 7/2014 |
| CN | 107056636 A | 8/2017 |
| CN | 109553554 A | 4/2019 |

OTHER PUBLICATIONS

Zima et al.; Investigation of flexibility of neuraminidase 150-loop using Tamiflu derivatives in influenza A viruses H1N1 and H5N1; Bioorganic & Medicinal Chemistry; May 17, 2019; vol. 27; pp. 2935-2947.

Ye et al.; Novel N-Substituted oseltamivir derivatives as potent influenza neuramindase inhibitors: Design, synthesis, biological evaluation, ADME prediction and molecular docking studies; European Journal of Medicinal Chemistry; Aug. 22, 2019; vol. 182; 111635.

Ye et al.; Design, Synthesis, Biological Evaluation and In Silico Studies of Pyrazole-Based NH2-Acyl Oseltamivir Analogues as Potent Neuraminidase Inhibitors; Pharmaceuticals; Apr. 16, 2021; vol. 14; 371.

*Primary Examiner* — Kamal A Saeed

(74) *Attorney, Agent, or Firm* — S&F/WEHRW

(57) ABSTRACT

Provided herein are oseltamivir analogs useful for the treatment and prevention of viral infections, pharmaceutical compositions comprising the same and methods preparation and use thereof.

15 Claims, 7 Drawing Sheets

N-SUBSTITUTED OSELTAMIVIR DERIVATIVES WITH ANTIMICROBIAL ACTIVITY

CROSS-REFERENCE TO RELATED APPLICATIONS

This application is a National Phase entry application of PCT International Application No. PCT/CN2020/097602, filed on Jun. 23, 2020, which claims the benefit of priority of United States Provisional Application No. 62/865,347, filed on Jun. 24, 2019, the contents of which being hereby incorporated by reference in their entirety for all purposes.

TECHNICAL FIELD

The present disclosure generally relates to compounds with antiviral activity. More particularly, the present disclosure relates to oseltamivir derivatives, pharmaceutical compositions comprising the same, and methods of use thereof.

BACKGROUND

Influenza, commonly known as flu, remains a severe viral infection which can outbreak with several characteristic symptoms such as fever, chills, pains, etc. The first isolation of influenza virus from fowls was in 1901. However, it was until the 1950s that the relationship of this and other bird-flu viruses with mammalian influenza A virus was first demonstrated. Particularly, influenza viruses are unique among the viruses with regard to their antigenic variability, seasonality, and impact on the general population. The continual emergence of new strains of influenza virus presents an ongoing threat to humankind.

Influenza A viruses contain two important surface antigenic glycoproteins, hemagglutinin (HA) and neuraminidase (NA). NA is an integral membrane glycoprotein which functions to free virus particles from host cell receptors. As NA has a major role in the virus' life cycle by promoting the release of virus progeny from the infected cell, so they are promising targets for anti-influenza drugs. NA inhibitors (NAIs) can prevent nascent viruses infecting intact cells by inhibiting their release from host cells. The most successful in clinical using NAIs including oseltamivir for oral administration, a prodrug of the corresponding oseltamivir carboxylate (OC) and zanamivir for inhalation, Laninamivir, and peramivir (4). However, various influenza virus mutants with resistance to these four drugs have been identified.

Thus, there is an urgent need to discover novel NAIs for influenza therapy.

SUMMARY

Accordingly, it is an object of the present disclosure to provide compounds that can inhibit viruses, in particular influenza viruses. In particular, the object of the present disclosure is to provide compounds that can inhibit neuraminidase, in particular can selectively inhibit viral neuraminidases.

An additional object of the present disclosure is to provide neuraminidase inhibitors that have enough oral bioavailability to be therapeutically effective. A still further object is to provide improved methods for administration of known and novel neuraminidase inhibitors.

In a first aspect, provided herein is a compound of Formula I:

I 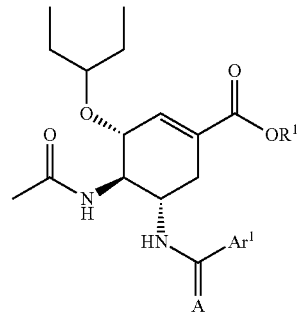 or a pharmaceutically acceptable salt thereof, wherein

A is O, S, or $H_2$;

$Ar^1$ is an optionally substituted 5 membered heteroaryl containing 1, 2, or 3 ring heteroatoms selected from the group consisting of O, C, N, P, S, and Se; and $R^1$ is hydrogen, alkyl, alkenyl, alkynyl, cycloalkyl, heterocycloalkyl, aryl, or heteroaryl.

In a first embodiment of the first aspect, provided herein is the compound of the first aspect, wherein the compound has Formula II:

II 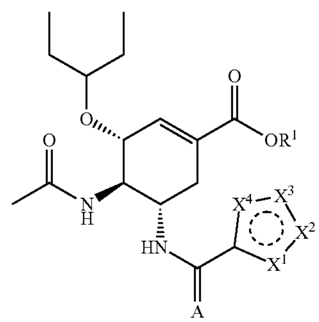 wherein each of $X^1$, $X^2$, $X^3$, and $X^4$ are independently selected from the group consisting of O, S, $NR^2$, and $CR^3$, wherein $R^2$ for each instance is independently a lone pair, hydrogen, alkyl, alkenyl, alkynyl, cycloalkyl, heterocycloalkyl, aryl, aralkyl, heteroaryl, —(C═O)R, —(C═O)OR, —(C═O)$NR_2$, —(C═NR)$NR_2$, —(S═O)R, —S(O)$_2$R, —S(O)$_2$OR, —S(O)$_2$$NR_2$, —(P═O)(OR)$_2$, or —$(CR_2)_m$Y; and $R^3$ for each instance is independently hydrogen, alkyl, alkenyl, alkynyl, cycloalkyl, heterocycloalkyl, aryl, aralkyl, heteroaryl, OR, SR, $NR_2$, —(C═O)R, —(C═O)OR, —O(C═O)R, —O(C═O)OR, —(C═O)$NR_2$, —(NR)(C═O)R, —(NR)(C═O)OR, —O(C═O)$NR_2$, —O(C═NR)$NR_2$, —(NR)(C═O)$NR_2$, —(C═NR)$NR_2$, —(NR)(C═NR)$NR_2$, —(S═O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, —(P═O)(OR)$_2$, halide, nitrile, nitro, or —$(CR_2)_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, $NR_2$, —(C═O)R, —(C═O)OR, —O(C═O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)NR₂, —(NR)S(O)₂NR₂, —(NR)S(O)₂OR, and —(P=O)(OR)₂.

In a second embodiment of the first aspect, provided herein is the compound of the first embodiment of the first aspect, wherein X² is CR³ or NR².

In a third embodiment of the first aspect, provided herein is the compound of the first embodiment of the first aspect, wherein A is O or H₂; and X² is CR³ or NR².

In a fourth embodiment of the first aspect, provided herein is the compound of the first aspect, wherein Ar¹ is selected from the group consisting of:

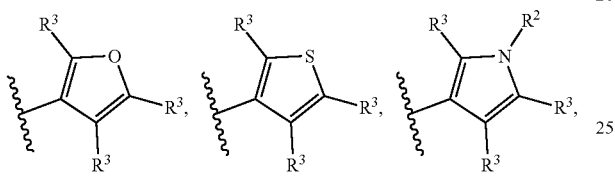

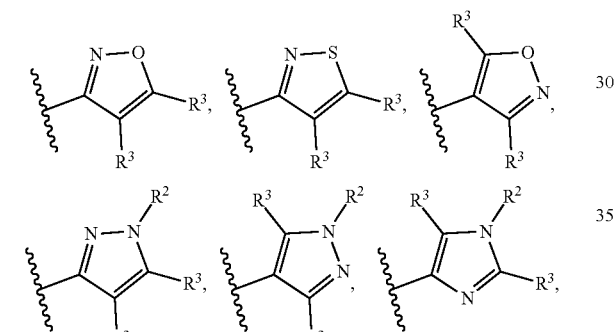

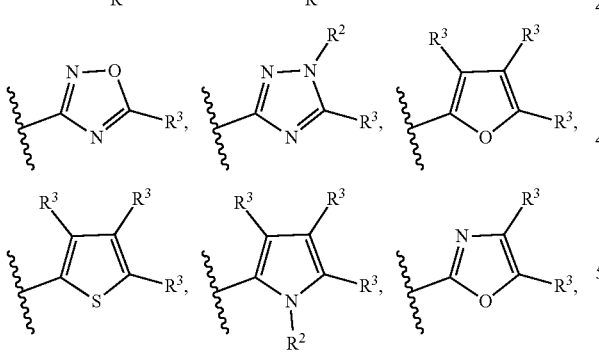

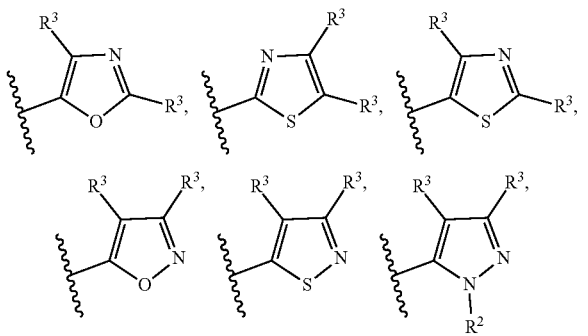

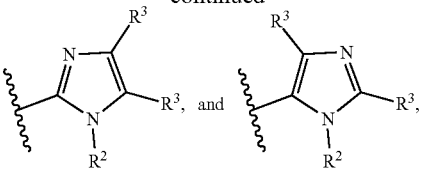

wherein R² is hydrogen, alkyl, alkenyl, alkynyl, cycloalkyl, heterocycloalkyl, aryl, aralkyl, heteroaryl, —(C=O)R, —(C=O)OR, —(C=O)NR₂, —(C=NR)NR₂, —(S=O)R, —S(O)₂R, —S(O)₂OR, —S(O)₂NR₂, —(P=O)(OR)₂, or —(CR₂)ₘY; and R³ for each instance is independently hydrogen, alkyl, alkenyl, alkynyl, cycloalkyl, heterocycloalkyl, aryl, aralkyl, heteroaryl, OR, SR, NR₂, —(C=O)R, —(C=O)OR, —O(C=O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)₂NR₂, —(NR)S(O)₂NR₂, —(NR)S(O)₂OR, —(P=O)(OR)₂, halide, nitrile, nitro, or —(CR₂)ₘY, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR₂, —(C=O)R, —(C=O)OR, —O(C=O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)₂NR₂, —(NR)S(O)₂NR₂, —(NR)S(O)₂OR, and —(P=O)(OR)₂.

In a fifth embodiment of the first aspect, provided herein is the compound of the first aspect, wherein Ar¹ is selected from the group consisting of:

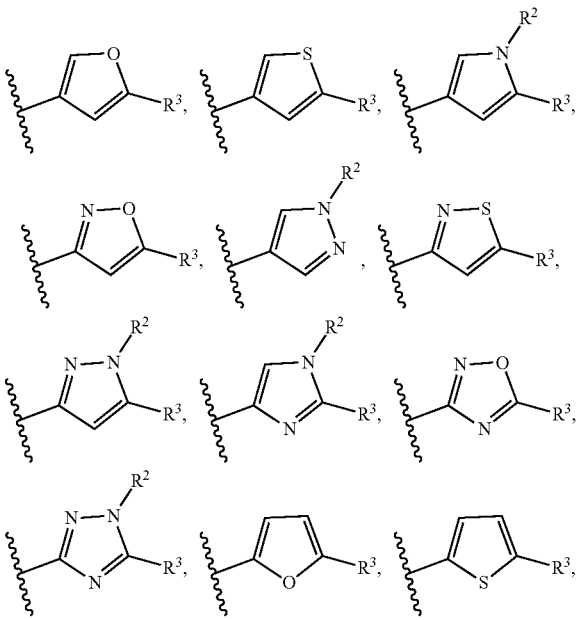

-continued

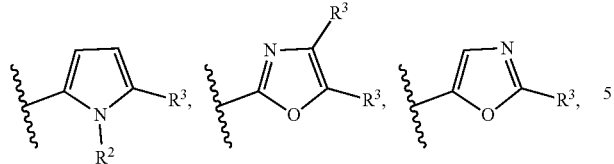

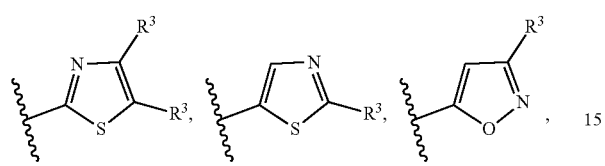

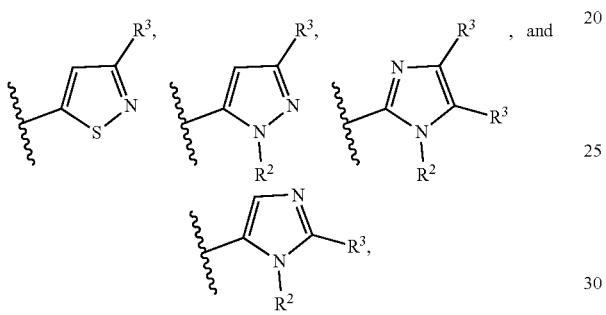

wherein R² is hydrogen, alkyl, alkenyl, alkynyl, cycloalkyl, heterocycloalkyl, aryl, aralkyl, heteroaryl, —(C=O)R, —(C=O)OR, —(C=O)NR₂, —(C=NR)NR₂, —(S=O)R, —S(O)₂R, —S(O)₂OR, —S(O)₂NR₂, —(P=O)(OR)₂ or —(CR₂)ₘY; and R³ for each instance is independently hydrogen, alkyl, alkenyl, alkynyl, cycloalkyl, heterocycloalkyl, aryl, aralkyl, heteroaryl, OR, SR, NR₂, —(C=O)R, —(C=O)OR, —O(C=O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)NR₂, —(NR)S(O)₂NR₂, —(NR)S(O)₂OR, —(P=O)(OR)₂, halide, nitrile, nitro, or —(CR₂)ₘY, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR₂, —(C=O)R, —(C=O)OR, —O(C=O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)₂NR₂, —(NR)S(O)₂NR₂, and —(P=O)(OR)₂.

In a sixth embodiment of the first aspect, provided herein is the compound of the first aspect, wherein the compound has the Formula III:

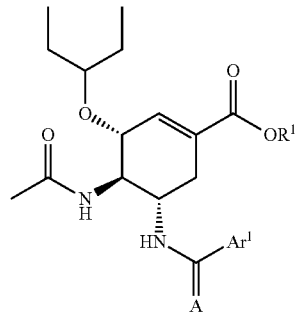

or a pharmaceutically acceptable salt thereof, wherein A is O or H₂;
Ar¹ is selected from the group consisting of:

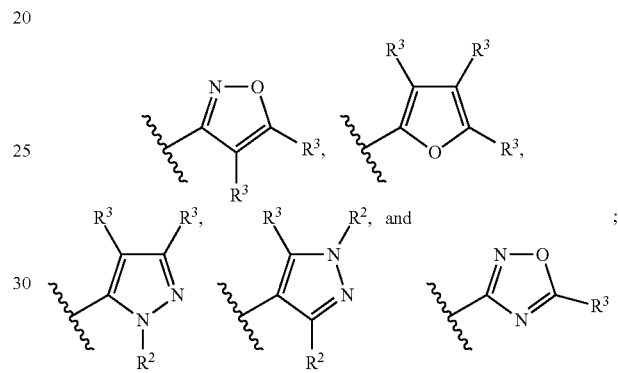

wherein R² is hydrogen, alkyl, alkenyl, alkynyl, cycloalkyl, heterocycloalkyl aryl, aralkyl, heteroaryl, —(C=O)R, —(C=O)OR, —(C=O)NR₂, —(C=NR)NR₂—(S=O)R, —S(O)₂R, —S(O)₂OR, —S(O)₂NR₂, —(P=O)(OR)₂, or —(CR₂)ₘY; and R for each instance is independently hydrogen, alkyl, alkenyl, alkynyl, cycloalkyl, heterocycloalkyl, aryl, aralkyl, heteroaryl, OR, SR, NR₂, —(C=O)R, —(C=O)OR, —O(C=O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)₂NR₂, —(NR)S(O)₂NR₂, —(NR)S(O)₂OR, —(P=O)(OR)₂, halide, nitrile, nitro, or —(CR₂)ₘY, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR₂, —(C=O)R, —(C=O)OR, —O(C=O)R, —O(C=O)OR, —(C=O)NR₂, —(NR)(C=O)R, —(NR)(C=O)OR, —O(C=O)NR₂, —O(C=NR)NR₂, —(NR)(C=O)NR₂, —(C=NR)NR₂, —(NR)(C=NR)NR₂, —(S=O)R, —S(O)₂R, —S(O)₂OR, —S(O)₂NR₂, —OS(O)₂R, —(NR)S(O)₂R, —OS(O)₂OR, —OS(O)₂NR₂, —(NR)S(O)₂NR₂, —(NR)S(O)₂OR, and —(P=O)(OR)₂; and R¹ is hydrogen, alkyl, alkenyl, alkynyl, cycloalkyl, heterocycloalkyl, aryl, or heteroaryl.

In a seventh embodiment of the first aspect, provided herein is the compound of the sixth embodiment of the first aspect, wherein $Ar^1$ is selected from the group consisting of:

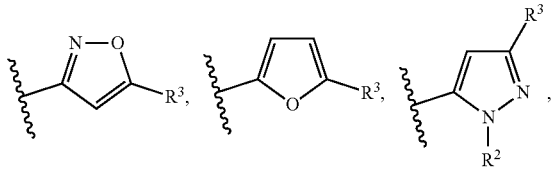

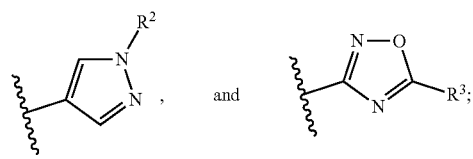

wherein $R^2$ is hydrogen, heterocycloalkyl, aryl, aralkyl, or heteroaryl; and $R^3$ is heterocycloalkyl, aryl, aralkyl, or heteroaryl.

In an eighth embodiment of the first aspect, provided herein is the compound of the first aspect, wherein the compound is selected from the group consisting of:

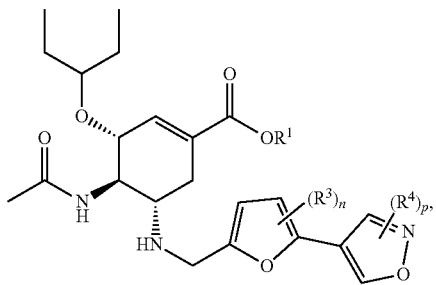

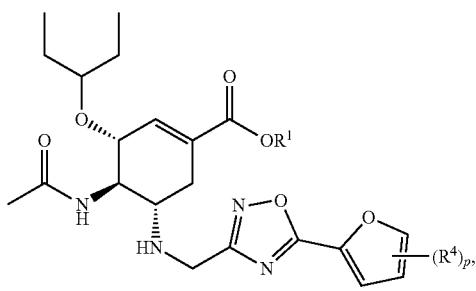

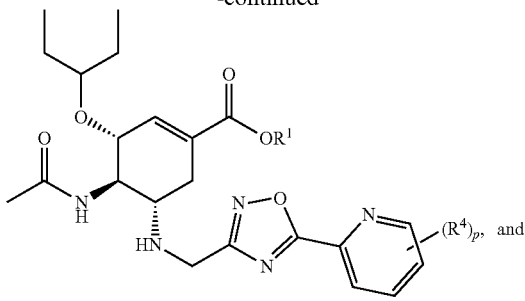

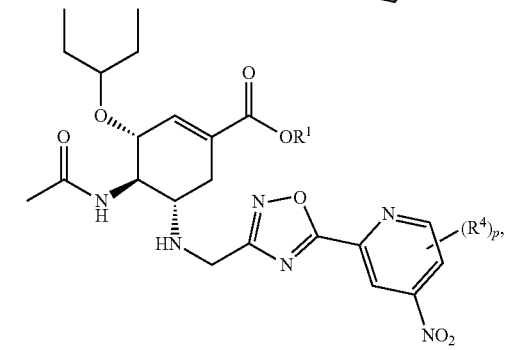

wherein n is 0, 1, or 2; p is 0, 1, or 2; and each of $R^3$ and $R^4$ for each occurrence is independently alkyl, alkenyl, alkynyl, cycloalkyl, heterocycloalkyl, aryl, aralkyl, heteroaryl, OR, SR, $NR_2$, —(C═O)R, —(C═O)OR, —O(C═O)R, —O(C═O)OR, —(C═O)$NR_2$, —(NR)(C═O)R, —(NR)(C═O)OR, —O(C═O)$NR_2$, —O(C═NR)$NR_2$, —(NR)(C═O)$NR_2$, —(C═NR)$NR_2$, —(NR)(C═NR)$NR_2$, —(S═O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, —(P═O)(OR)$_2$, halide, nitrile, nitro, or —(CH$_2$)$_m$Y, wherein in for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, $NR_2$, —(C═O)R, —(C═O)OR, —O(C═O)R, —O(C═O)OR, —(C═O)$NR_2$, —(NR)(C═O)R, —(NR)(C═O)OR, —O(C═O)$NR_2$, —O(C═NR)$NR_2$, —(NR)(C═O)$NR_2$, —(C═NR)$NR_2$, —(NR)(C═NR)$NR_2$, —(S═O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, and —(P═O)(OR)$_2$.

The compound of claim 9, wherein n is 0; and $R^4$ for each occurrence is independently alkyl, cycloalkyl, heterocycloalkyl, aryl, aralkyl, heteroaryl, OR, $NR_2$, —(C═O)R, —(C═O)OR, —O(C═O)R, —O(C═O)OR, —(C═O)$NR_2$, —(NR)(C═O)R, —(NR)(C═O)OR, —O(C═O)$NR_2$, —O(C═NR)$NR_2$, —(NR)(C═O)$NR_2$, —(C═NR)$NR_2$, —(NR)(C═NR)$NR_2$, —(S═O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, —(P═O)(OR)$_2$, halide, nitrile, nitro, or —(CH$_2$)$_m$Y, wherein m is 1-6; and R for each occurrence is independently hydrogen, alkyl, cycloalkyl, aryl, or heteroaryl.

In a ninth embodiment of the first aspect, provided herein is the compound of the first aspect, wherein the compound is selected from the group consisting of:

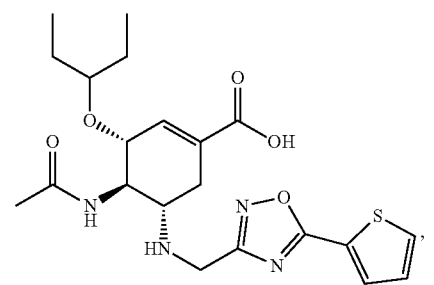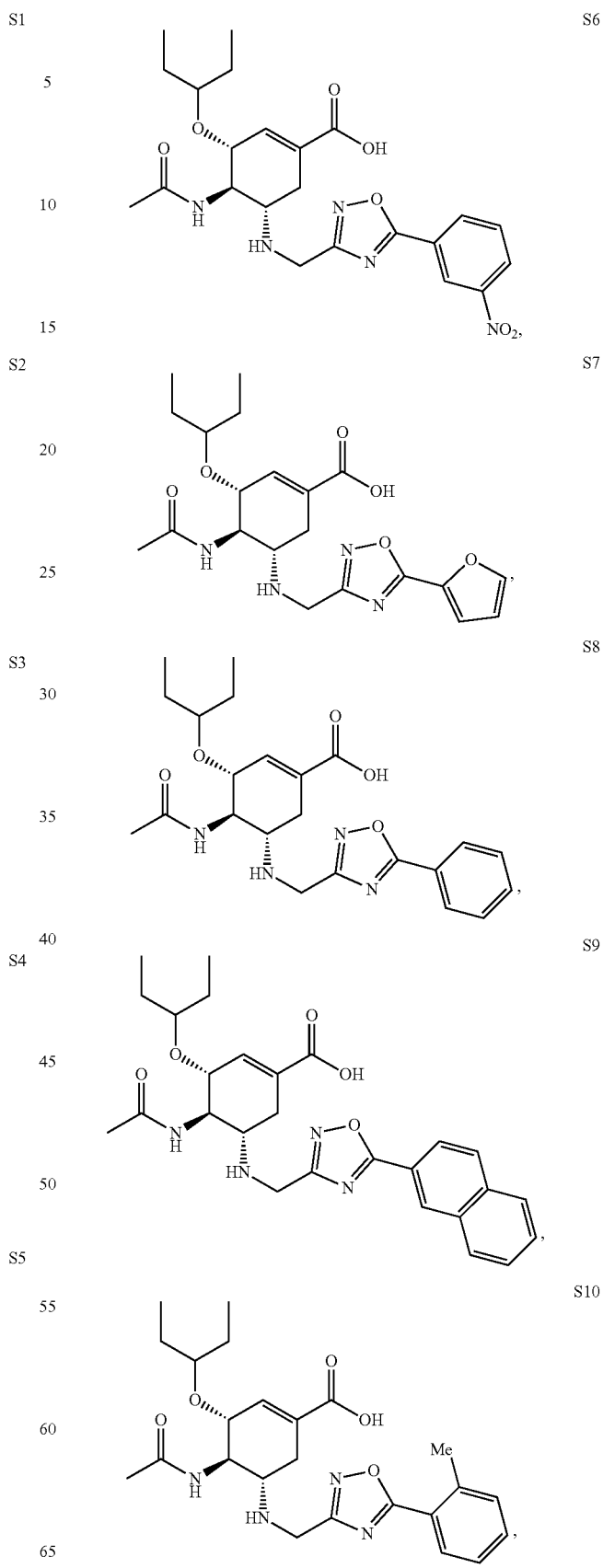

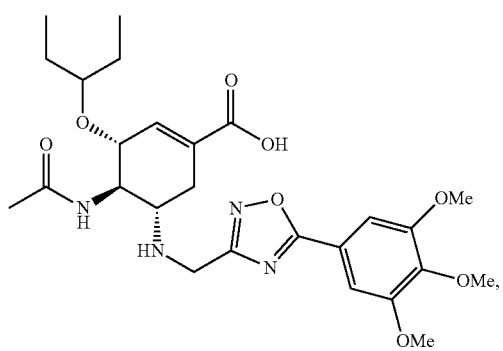
S11
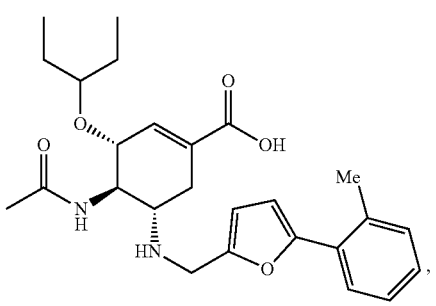
S16
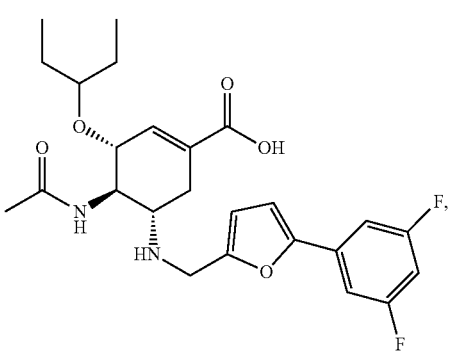
S12, S17
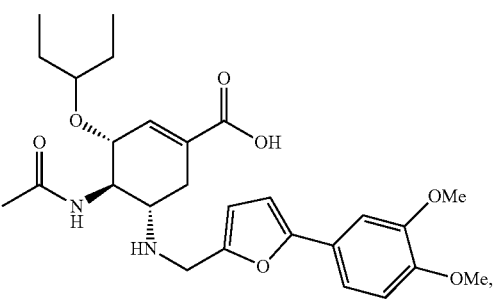
S13, S18
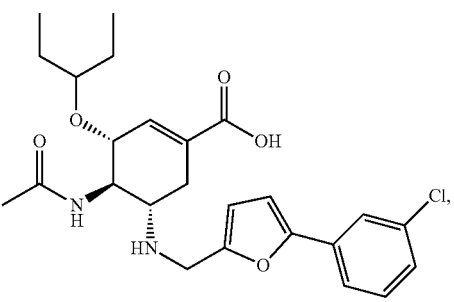
S14, S19
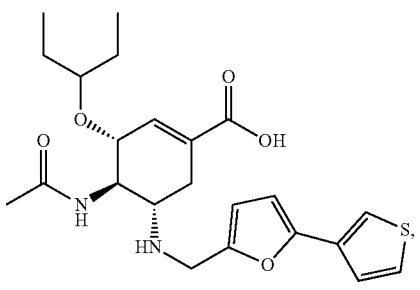
S15, S20

S21
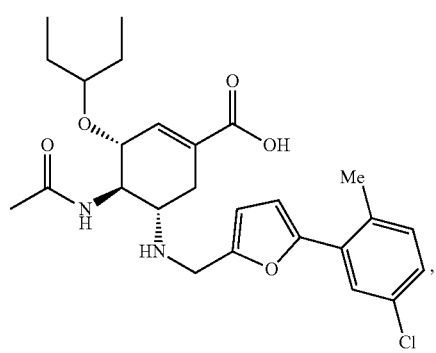
S22
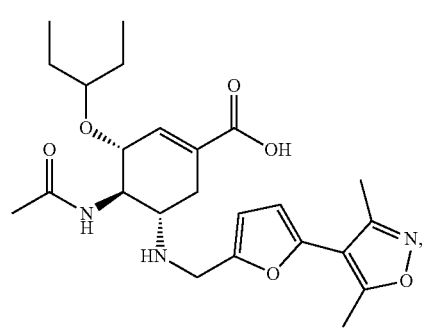
S23
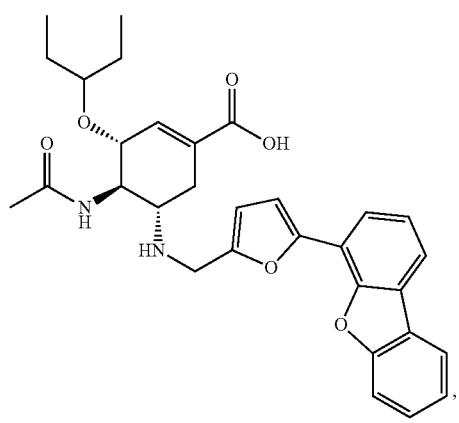
S24
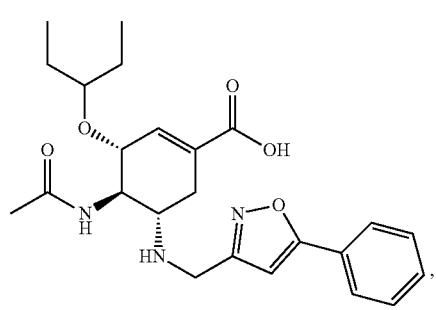
S25
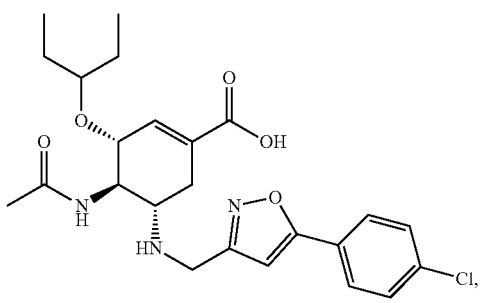
S26
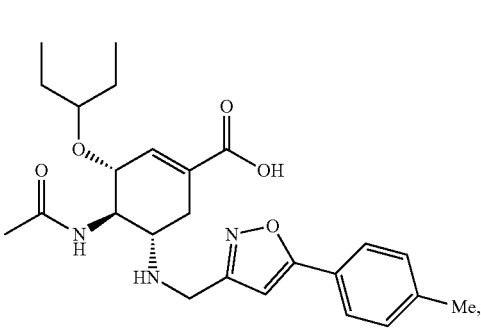
S27
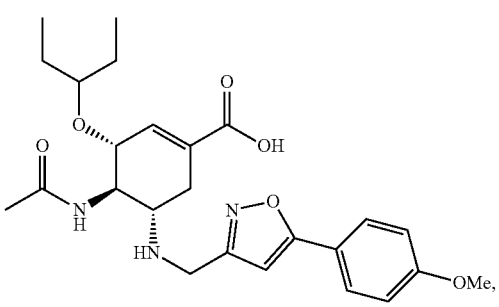
S28
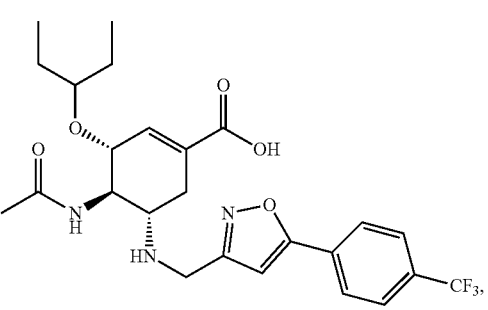
S29
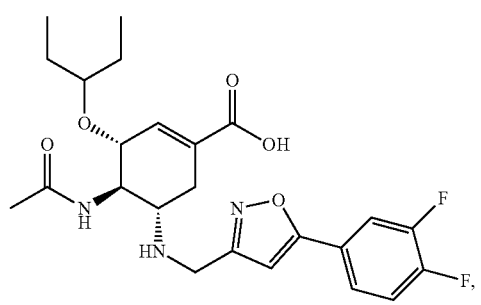

S30
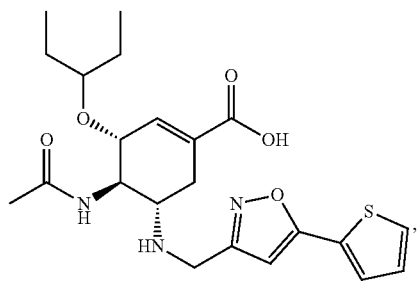
S31
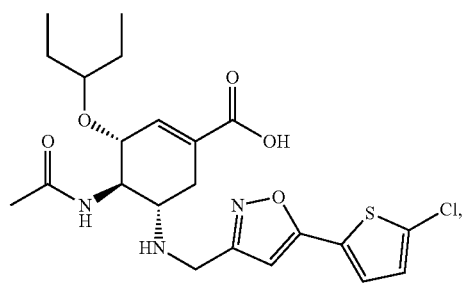
OC-001
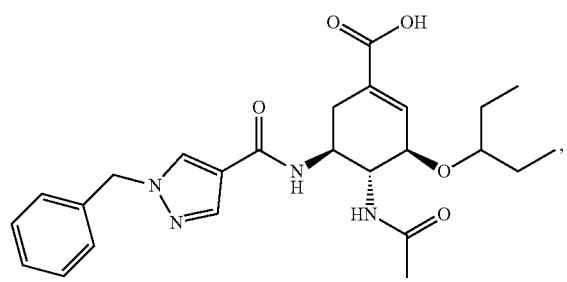
OC-002
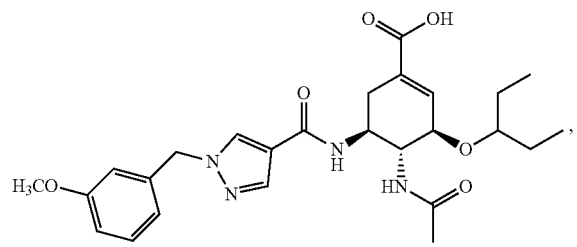
OC-003
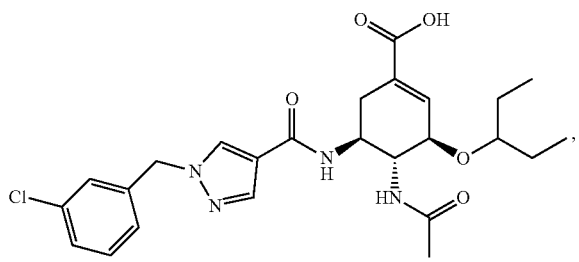
OC-004
OC-005
OC-006
OC-007
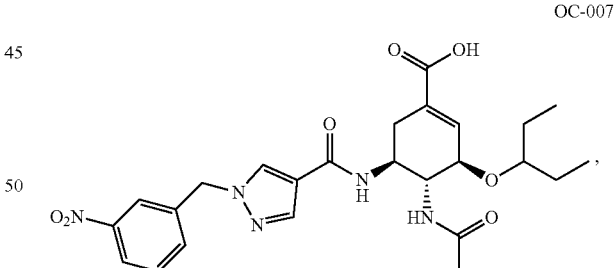
OC-008

OC-009
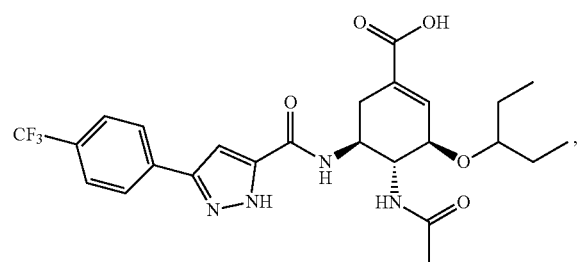
OC-010
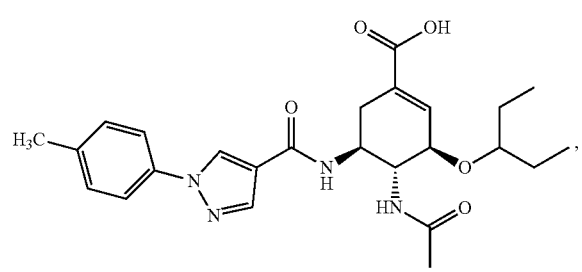
OC-011
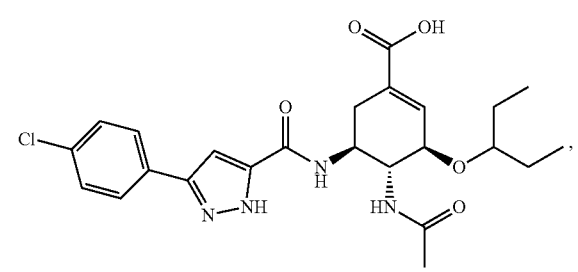
OC-012
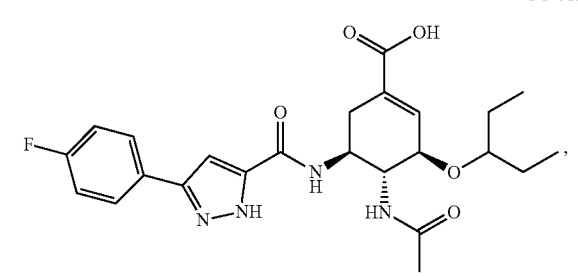
OC-013
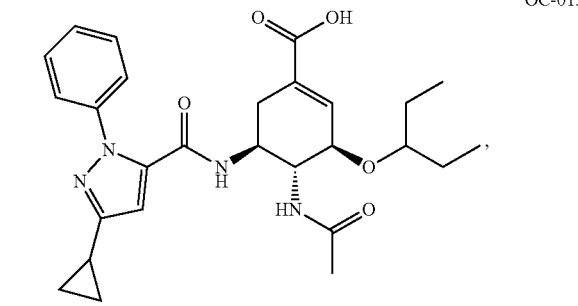
OC-014
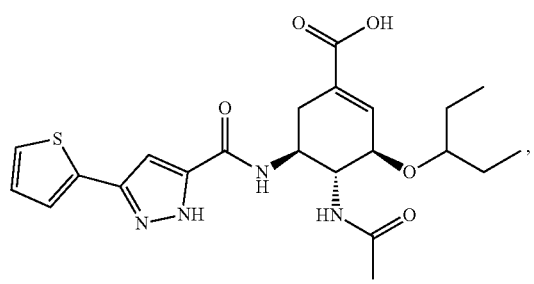
OC-015
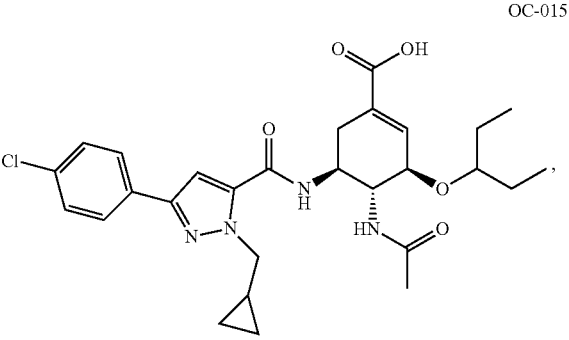
OC-016
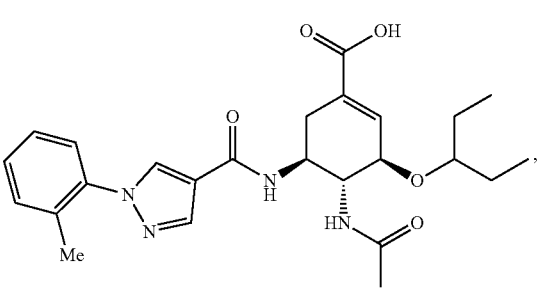
OC-017
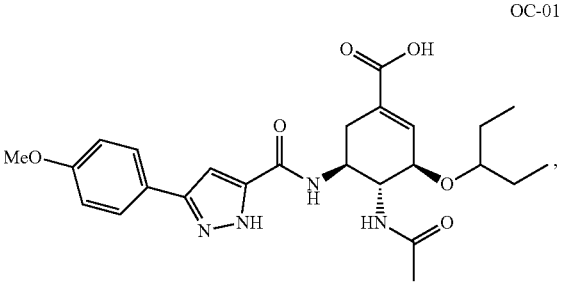
OC-018
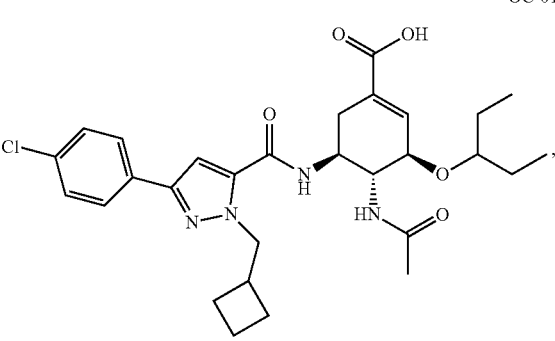

OC-0019
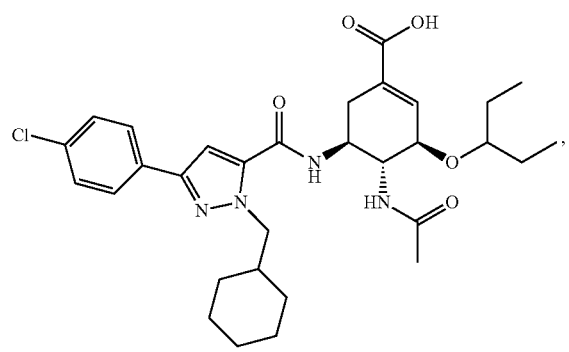
OC-0020
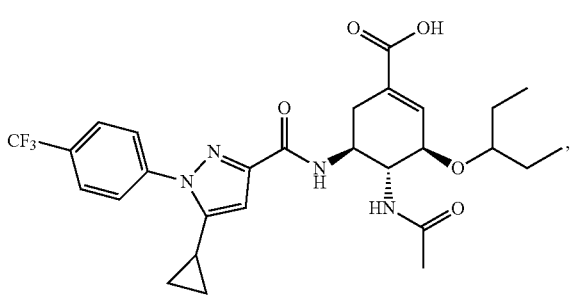
OC-0021
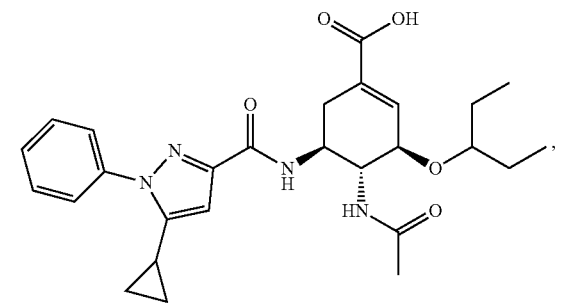
OC-022
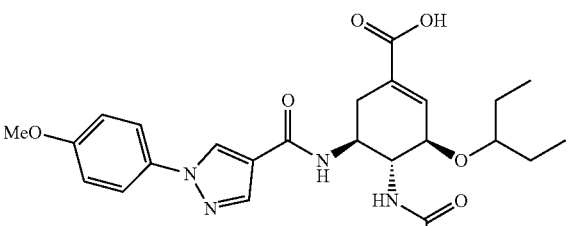
OC-023
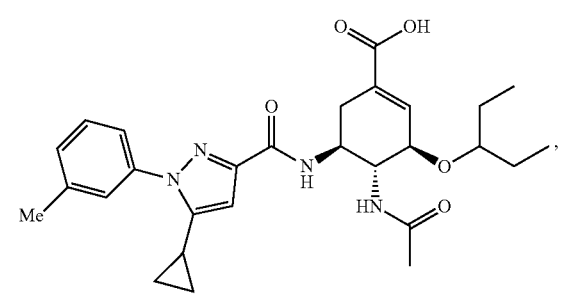
OC-024
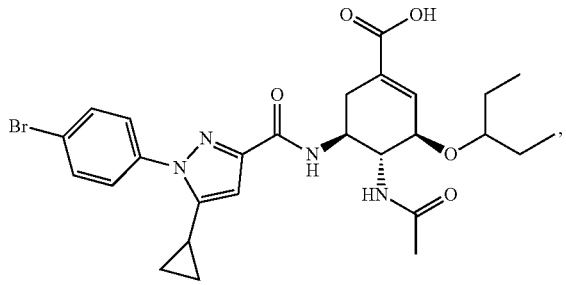
OC-025
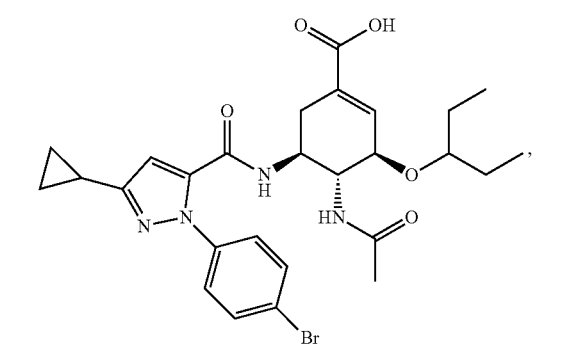
OC-026
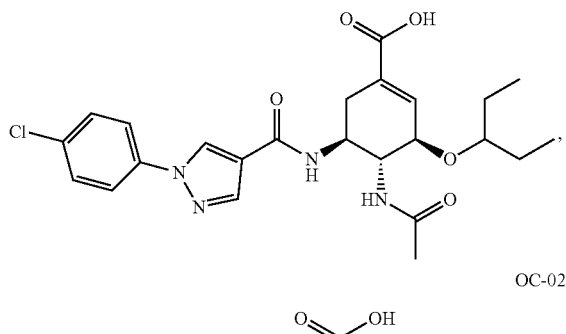
OC-027
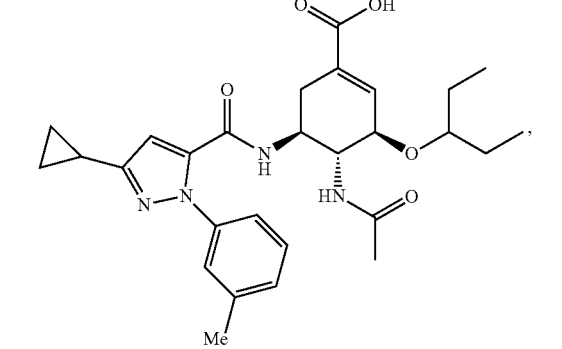
OC-028
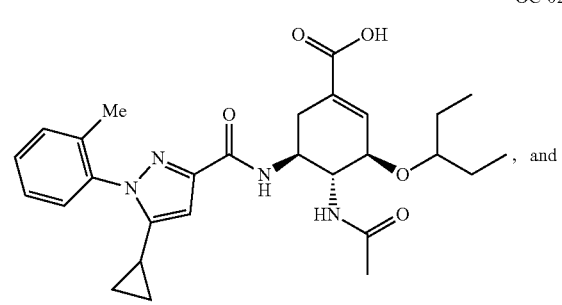
, and -continued

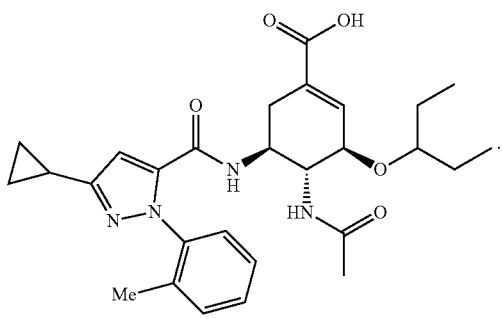

OC-029

In a tenth embodiment of the first aspect, provided herein is the compound of the first aspect, wherein the compound is selected from the group consisting of:

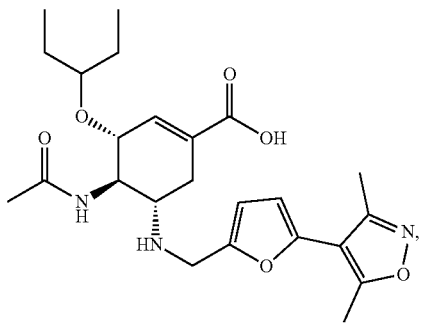

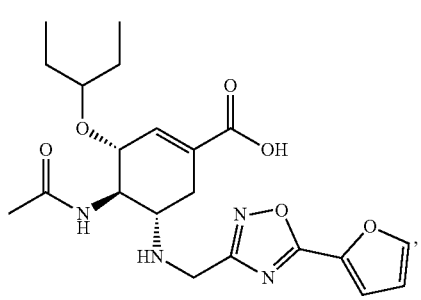

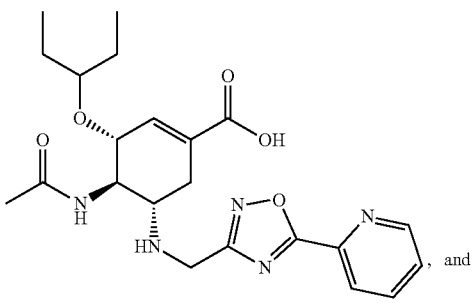, and

-continued

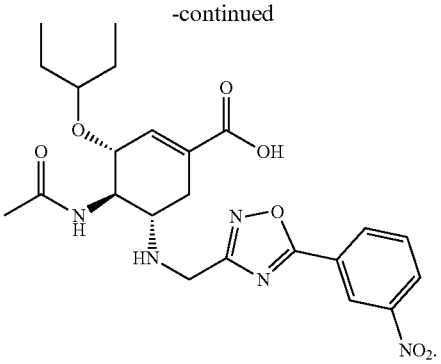

In a second aspect, provided herein is a pharmaceutical composition comprising a compound of the first aspect and at least one pharmaceutically acceptable carrier.

In a third aspect, provided herein is a method of preparing a compound of claim 1, the method comprising: contacting a compound of Formula IV:

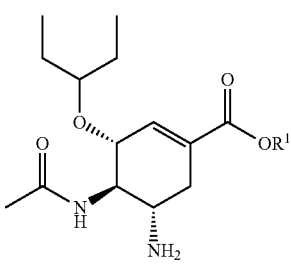

IV wherein $R^1$ is hydrogen, alkyl, alkenyl, alkynyl, cycloalkyl, heterocycloalkyl, aryl, or heteroaryl; with a compound Formula V:

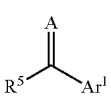

V wherein A is O, S, or $H_2$; $R^5$ is a leaving group; and $Ar^1$ is an optionally substituted 5 membered heteroaryl containing 1, 2, or 3 ring heteroatoms selected from the group consisting of O, C, N, P, S, and Se; or contacting the compound of Formula 3 with a compound Formula VI:

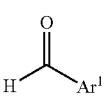

VI wherein $Ar^1$ is an optionally substituted 5 membered heteroaryl containing 1, 2, or 3 ring heteroatoms selected from the group consisting of O, C, N, P, S, and Se; and a reducing agent; thereby forming the compound of claim 1.

In a first embodiment of the third aspect, provided herein is the method of the third aspect, wherein $R^5$ is a halide; and the reducing agent is $NaCNBH_3$.

In a fourth aspect, provided herein is a method of treating a viral infection in a subject in need thereof comprising the step of administering a therapeutically effective amount of the compound of claim 1 to the subject.

In a first embodiment of the fourth aspect, provided herein is the method of the first aspect, wherein the viral infection is an influenza viral infection.

In a second embodiment of the fourth aspect, provided herein is the method of the first aspect, wherein the viral infection is a H1N1 or H3N2 infection.

In a third embodiment of the fourth aspect, provided herein is the method of the first aspect, wherein the compound is selected from the group consisting of:

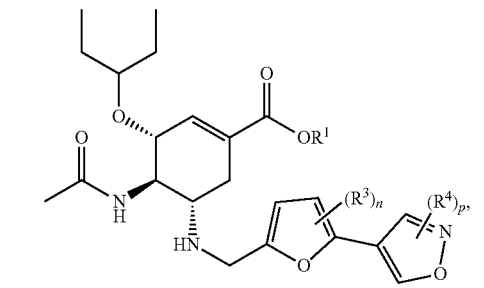

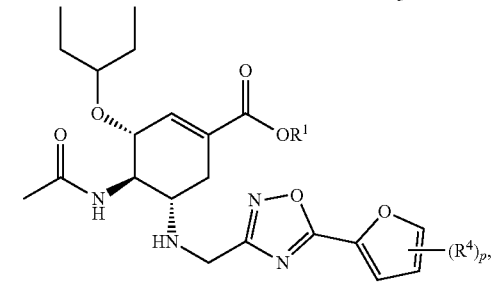

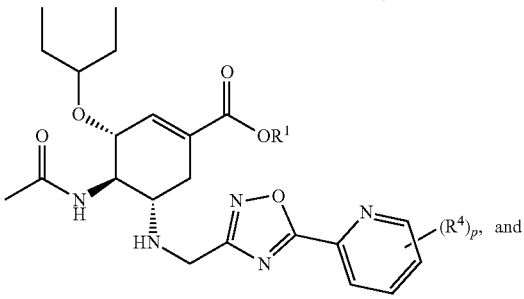

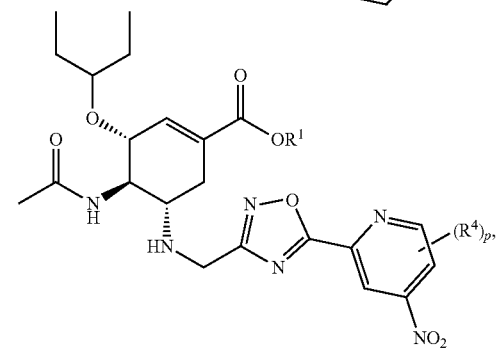

wherein n is 0, 1, or 2; p is 0, 1, or 2; and each of $R^3$ and $R^4$ for each occurrence is independently alkyl, alkenyl, alkynyl, cycloalkyl, heterocycloalkyl, aryl, aralkyl, heteroaryl, OR, SR, NR$_2$, —(C=O)R, —(C=O)OR, —O(C=O)R, —O(C=O)OR, —(C=O)NR$_2$, —(NR) (C=O)R, —(NR)(C=O)OR, —O(C=O)NR$_2$, —O(C=NR)NR$_2$, —(NR)(C=O)NR$_2$, —(C=NR) NR$_2$, —(NR)(C=NR)NR$_2$, (S=O)R, —S(O)$_2$R, —S(O)$_2$OR, —S(O)$_2$NR$_2$, —OS(O)$_2$R, —(NR)S(O)$_2$ R, —OS(O)$_2$OR, —OS(O)$_2$NR$_2$, —(NR)S(O)$_2$NR$_2$, —(NR)S(O)$_2$OR, —(P=O)(OR)$_2$, halide, nitrile, nitro, or —(CH$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —(NR)(C=O)NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P=O)(OR)$_2$.

In a fourth embodiment of the fourth aspect, provided herein is the method of the second embodiment of the first aspect, wherein the compound is selected from the group consisting of:

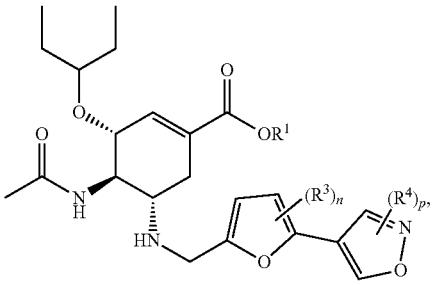

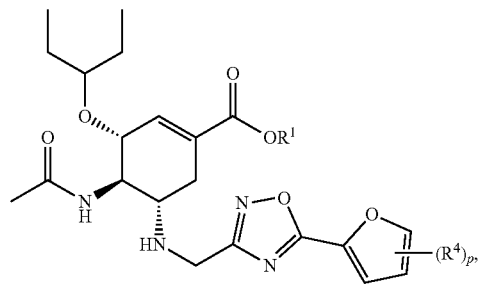

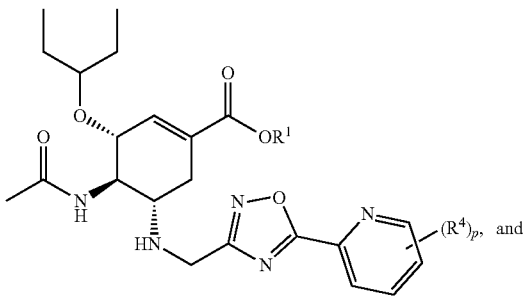

-continued

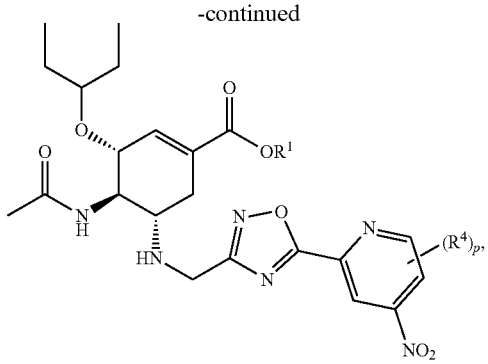

wherein n is 0, 1, or 2; p is 0, 1, or 2; and each of $R^3$ and $R^4$ for each occurrence is independently alkyl, alkenyl, alkynyl, cycloalkyl, heterocycloalkyl, aryl, aralkyl, heteroaryl, OR, SR, $NR_2$, —(C=O)R, —(C=O)OR, —O(C=O)R, —O(C=O)OR, —(C=O)$NR_2$, —(NR) (C=O)R, —(NR)(C=O)OR, —O(C=O)$NR_2$, —O(C=NR)$NR_2$, —(NR)(C=O)$NR_2$, —(C=NR) $NR_2$, —(NR)(C=NR)$NR_2$, —(S=O)R, —S(O)$_2$R, —S(O)$_2$OR, —S(O)$_2$$NR_2$, —OS(O)$_2$R, —(NR)S(O)$_2$ R, —OS(O)$_2$OR, —OS(O)$_2$$NR_2$, —(NR)S(O)$_2$$NR_2$, —(NR)S(O)$_2$OR, —(P=O)(OR)$_2$, halide, nitrile, nitro, or —(CH$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR) $NR_2$, —(NR)(C=O)$NR_2$, —(C=NR)$NR_2$, —(NR) (C=NR)$NR_2$, —(S=O)R, —S(O)$_2$R, —S(O)$_2$OR, —S(O)$_2$$NR_2$, —OS(O)$_2$R, —(NR)S(O)$_2$R, —OS(O)$_2$ OR, —OS(O)$_2$$NR_2$, —(NR)S(O)$_2$$NR_2$, —(NR)S(O)$_2$ OR, and —(P=O)(OR)$_2$.

These and other objects will be apparent from consideration of the present disclosure as a whole.

Those skilled in the art will appreciate that the disclosure described herein is susceptible to variations and modifications other than those specifically described.

Other aspects and advantages of the disclosure will be apparent to those skilled in the art from a review of the ensuing description.

BRIEF DESCRIPTION OF DRAWINGS

The above and other objects and features of the present disclosure will become apparent from the following description of the disclosure, when taken in conjunction with the accompanying drawings, in which.

DETAILED DESCRIPTION

Definitions

Figure 1:
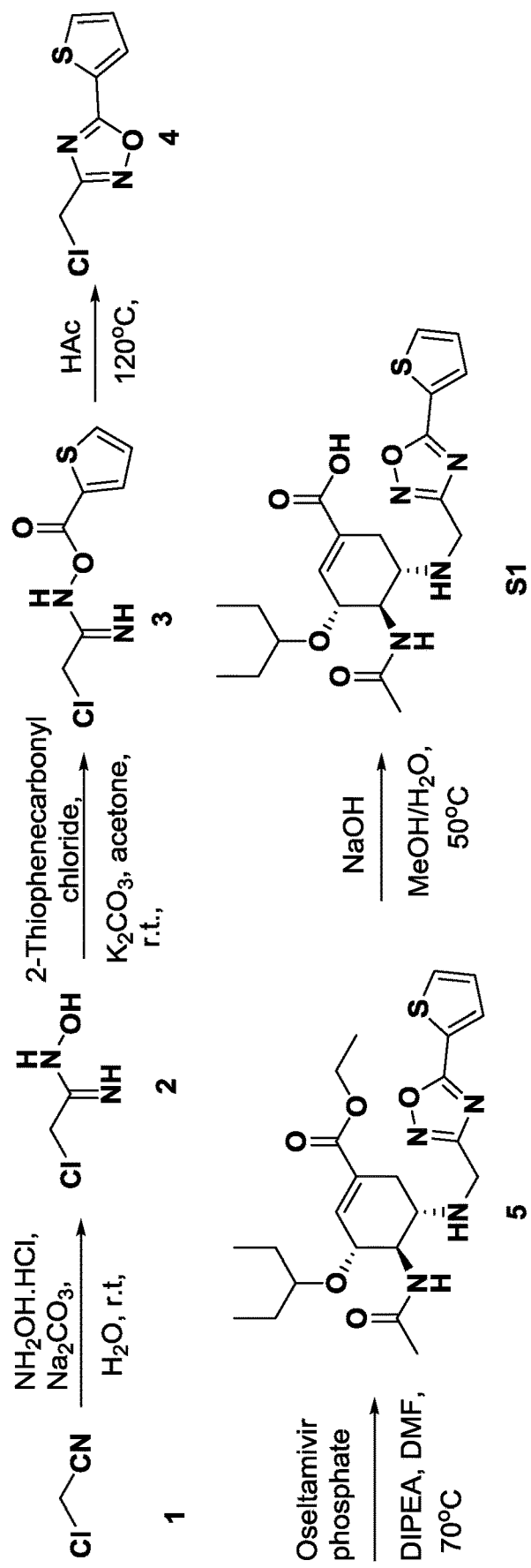
FIG. 1 depicts a schematic illustration of the preparation of the compound S1.

The following terms shall be used to describe the present invention. In the absence of a specific definition set forth herein, the terms used to describe the present invention shall be given their common meaning as understood by those of ordinary skill in the art.

As used herein, unless otherwise indicated, the term "treating" means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological, medicinal, or imaging response in a cell culture, tissue system, subject, animal, or human that is being sought by a researcher, veterinarian, clinician, or physician, which includes alleviation of the symptoms of the disease, condition, or disorder being treated and/or achieving the desired degree of magnetic resonance imaging contrast enhancement.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. L. Kibbe ed. (American Pharmaceutical Assoc. 2000), disclose various carriers used in formulating pharmaceutical compositions and known techniques for the preparation thereof.

As used herein, unless otherwise indicated, the term "halo" or "halide" includes fluoro, chloro, bromo or iodo. Preferred halo groups are fluoro, chloro and bromo.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

As used herein, unless otherwise indicated, the term "alkenyl", as used herein, unless otherwise indicated, includes alkyl groups as defined above having at least one carbon-carbon double bond at some point in the alkyl chain.

As used herein, unless otherwise indicated, the term "alkynyl", as used herein, unless otherwise indicated, includes alkyl groups as defined above having at least one carbon-carbon triple bond at some point in the alkyl chain.

The term "aralkyl" is art-recognized and refers to an alkyl group substituted with an aryl group (e.g., an aromatic or heteroaromatic group).

The term "aryl" as used herein include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. The aryl group can be optionally substituted. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be optionally substituted as described herein. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like. A "nitrogen containing heteroaryl" is a heteroaryl as defined herein with an aromatic ring system having at least one ring nitrogen (N).

The term "optionally substituted" refers to a chemical group, such as alkyl, cycloalkyl, aryl, heteroaryl, and the like, wherein one or more hydrogen may be replaced with a substituent as described herein, for example, halogen, azide, alkyl, aralkyl, alkenyl, alkynyl, cycloalkyl, hydroxyl, aryloxy, heteroaryloxy, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

The term "therapeutically effective amount" as used herein, means that amount of the compound or a pharmaceutical composition that elicits a biological or medicinal response in a cell culture, tissue system, animal, or human that is being sought by a researcher, veterinarian, clinician, or physician, which includes alleviation of the symptoms of the disease, condition, or disorder being treated.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein, the term "subject" refers to any animal (e.g., a mammal), including, but not limited to, humans, non-human primates, canines, felines, and rodents.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The present disclosure provides a compound of Formula I:

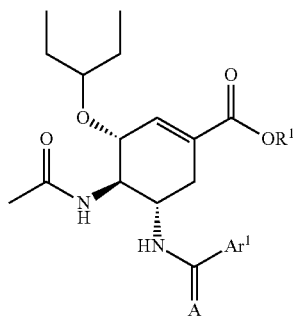

or a pharmaceutically acceptable salt thereof, wherein
A is O, S, or H$_2$;
Ar$^1$ is an optionally substituted five-membered heteroaryl containing 1, 2, or 3 ring heteroatoms selected from the group consisting of O, C, N, P, S, and Se; and
R$^1$ is hydrogen, alkyl, alkenyl, alkynyl, cycloalkyl, heterocycloalkyl, aryl, or heteroaryl.

In instances in which A is H$_2$, the compound of Formula I can have the structure:

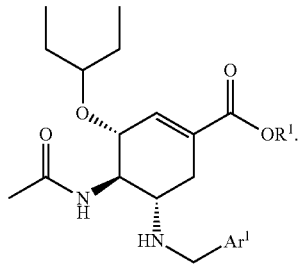

Exemplary five-membered heteroaryls include, but are not limited to furan, pyrrole, thiophene, selenophene, pyrazole, oxazole, isoxazole, thiazole, isothiazole, imidazole, 1,2,3-triazole, 1,2,4-triazole, 1,3-selenazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, and the like.

The five-membered heteroaryl may covalently bonded to —(C=A)- at any position of the heteroaryl permitted by valency. In certain embodiments, the five-membered heteroaryl is covalently bonded to —(C=A)- at the 1, 2, 3, 4, or 5 position of the five-membered heteroaryl.

The five-membered heteroaryl can be represented by the moiety:

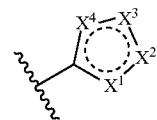

wherein ⁀ represents a covalent bond to —(C=A)-; each of X$^1$, X$^2$, X$^3$, and X$^4$ are independently selected from the group consisting of O, S, NR$^2$, and CR$^3$, wherein R$^2$ for each instance is independently a lone pair, hydrogen, alkyl, alkenyl, alkynyl, cycloalkyl, heterocycloalkyl, aryl, aralkyl, heteroaryl, —(C=O)R, —(C=O)OR, —(C=O)NR$_2$, —(C=NR)NR$_2$, —(S=O)R, —S(O)$_2$R, —S(O)$_2$OR, —S(O)$_2$NR$_2$, —(P=O)(OR)$_2$, or —(CR$_2$)$_m$Y; and R$^3$ for each instance is independently hydrogen, alkyl, alkenyl, alkynyl, cycloalkyl, heterocycloalkyl, aryl, aralkyl, heteroaryl, OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —(NR)(C=O)NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, —(P=O)(OR)$_2$, halide, nitrile, nitro, or —(CR$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —(NR)(C=O)NR$_2$, —(C=NR)NR$_2$, —(NR)(C=NR)NR$_2$, —(S=O)R, —S(O)$_2$R, —S(O)OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P=O)(OR)$_2$.

In instances in which any one of X$^1$, X$^2$, X$^3$, and X$^4$ is NR$^2$ having an sp$^2$ hybridized nitrogen, R$^2$ may be a lone pair. However, the present disclosure also contemplates embodiments, in which any one of X$^1$, X$^2$, X$^3$, and X$^4$ is NR$^2$ having an sp$^2$ hybridized nitrogen, and R$^2$ is not a lone pair, which results in a cationic species. Such species are well known in the art and can exist together with one or more counter ions, e.g., as a salt.

In certain embodiments, X$^2$ is CR$^3$ or NR$^2$, wherein R$^2$ is not a lone pair. In certain embodiments, X$^1$ is O or NR$^2$, wherein R is a long pair; and X$^2$ is CR$^3$. In certain embodiments, X$^1$ is NR$^2$, wherein R$^2$ is not a lone pair; and X$^2$ is NR$^2$, wherein R$^2$ is a lone pair.

In certain embodiments, R for each occurrence is independently selected from the group consisting of hydrogen, alkyl, alkenyl, alkynyl, cycloalkyl, heterocycloalkyl, aryl, and heteroaryl. In certain embodiments, R for each occurrence is independently selected from the group consisting of hydrogen, alkyl, cycloalkyl, heterocycloalkyl, aryl, heteroaryl. and In certain embodiments, R for each occurrence is independently selected from the group consisting of hydrogen, C$_1$-C$_8$ alkyl, C$_1$-C$_6$ alkyl, C$_3$-C$_8$ cycloalkyl, C$_4$-C$_6$cycloalkyl, C$_2$-C$_8$ heterocycloalkyl, C$_4$-C$_5$ heterocycloalkyl, C$_6$-C$_{10}$ aryl, and C$_6$-C$_{10}$ heteroaryl.

In certain embodiments, R$^1$ is hydrogen, C$_1$-C$_{10}$ alkyl, C$_1$-C$_8$ alkyl, C$_1$-C$_6$ alkyl, C$_1$-C$_4$ alkyl, or C$_1$-C$_2$ alkyl.

In certain embodiments, R$^2$ for each occurrence is independently selected from the group consisting of a lone pair, hydrogen, alkyl, cycloalkyl, heterocycloalkyl, aryl, aralkyl, and heteroaryl. In certain embodiments, R$^2$ for each occurrence is independently selected from the group consisting of a lone pair, hydrogen, heterocycloalkyl, aryl, aralkyl, and heteroaryl.

In certain embodiments, R$^3$ for each occurrence is independently selected from the group consisting of hydrogen, alkyl, cycloalkyl, heterocycloalkyl, aryl, aralkyl, heteroaryl, halide, nitrile, and nitro. In certain embodiments, R$^3$ for each occurrence is independently selected from the group consisting of hydrogen, aryl, aralkyl, and heteroaryl.

In certain embodiments, Ar$^1$ can be represented by a moiety selected from the group consisting of:

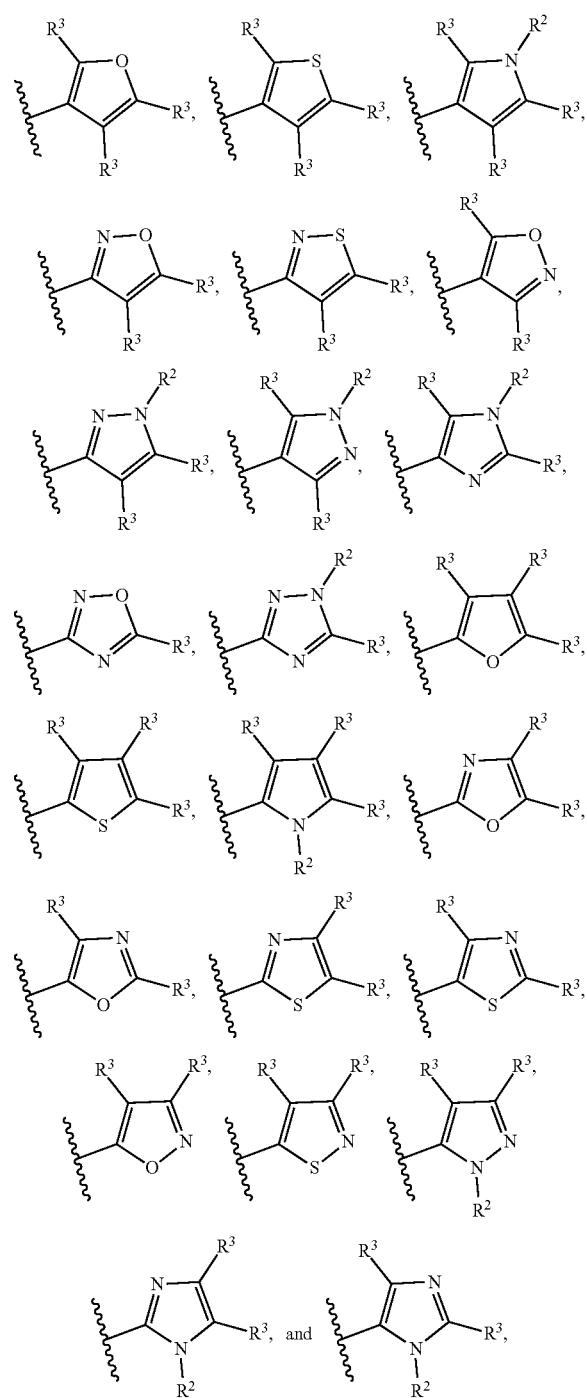

wherein R$^2$ and R$^3$ are as defined herein.

In certain embodiments, Ar$^1$ can be represented by a moiety selected from the group consisting of:

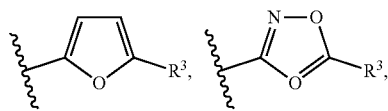

-continued

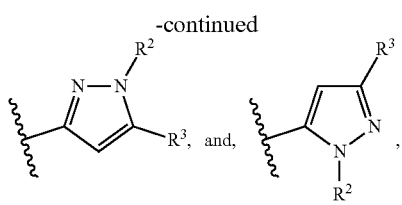

wherein R² and R³ are as defined herein.

In certain embodiments, the compound has the Formula III:

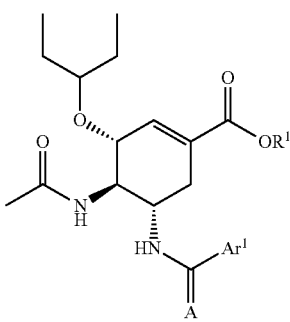

or a pharmaceutically acceptable salt thereof, wherein
A is O or H₂;
Ar¹ is selected from the group consisting of:

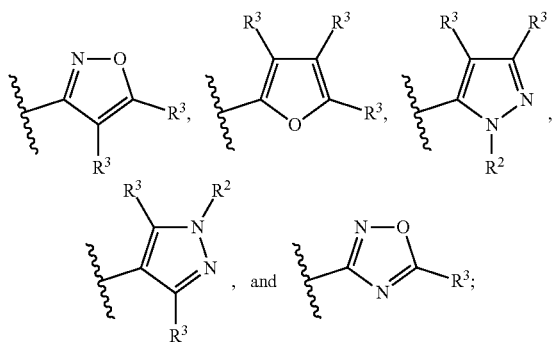

wherein R¹, R² and R³ are as defined herein.

In alternative embodiments, provided herein are compounds of Formula IA provided herein:

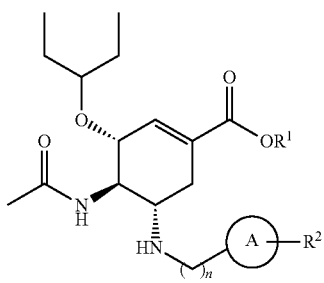

wherein
n is zero, one, two or three;

R¹ is hydrogen, (C₁-C₁₆)-alkyl, or (C₃-C₁₄)-cycloalkyl;

A is independently heterocycle, or heteroaryl, including but not restricted to furan, pyrrole, imidazole, pyrazole, triazole, pyridine, pyrimidine, pyridazine, pyrazine, thiophene, oxazole, thiazole, azepine, 1,4-diazepine, 1,2,4-oxidazole, isoxazole; and R² is independently (C₁-C₁₆)-alkyl, (C₃-C₁₄)-cycloalkyl, (C₅-C₁₄)-aryl or (C₅-C₁₄)-heteroaryl.

In certain embodiments, the compound has Formula IIA:

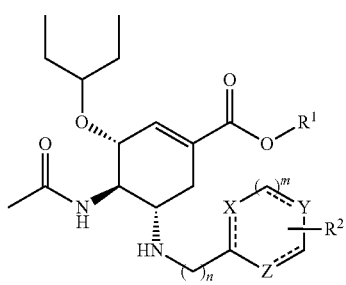

wherein
n is zero, one, two or three;
m is zero, one or two;
R¹ is hydrogen, (C₁-C₁₆)-alkyl, or (C₃-C₁₄)-cycloalkyl;
X is C, CH, N, NH, O or S;
Y is C, CH, N, NH, O or S;
Z is C, CH, N, NH, O or S; and
R² is (C₁-C₁₆)-alkyl, (C₃-C₁₄)-cycloalkyl, (C₅-C₁₄)-aryl or (C₅-C₁₄)-heteroaryl.

In certain embodiments, the compound is selected from the group consisting of a compound of Formula IIIA, IVA and IVA:

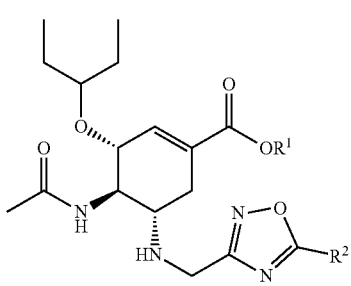

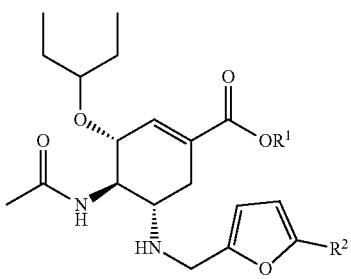

VA
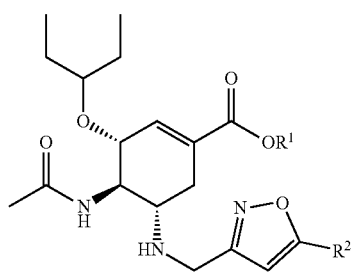
wherein
R[1] is or hydrogen, $(C_1-C_{16})$-alkyl, $(C_3-C_{14})$-cycloalkyl;
R[2] is $(C_1-C_{16})$-alkyl, $(C_3-C_{14})$-cycloalkyl, $(C_5-C_{14})$-aryl and $(C_5-C_{14})$-heteroaryl.
In certain embodiments, the compound is selected from:
S1
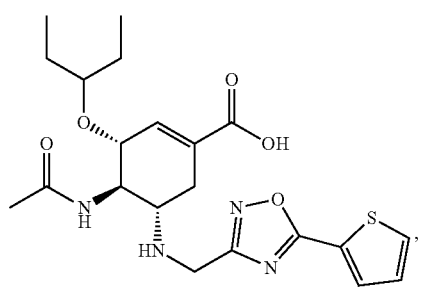
S2
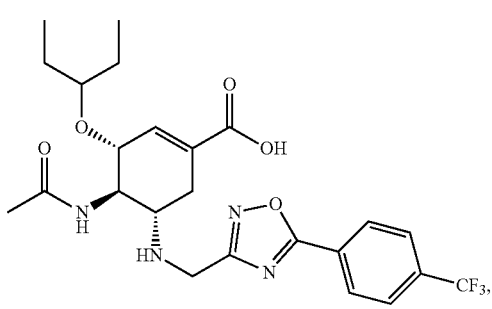
S3
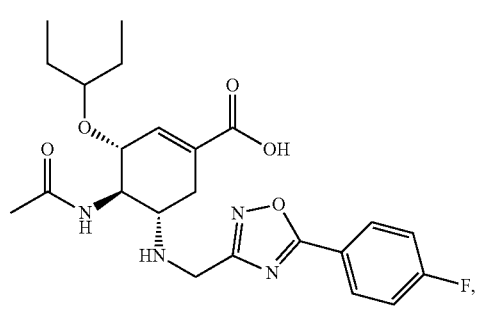
S4
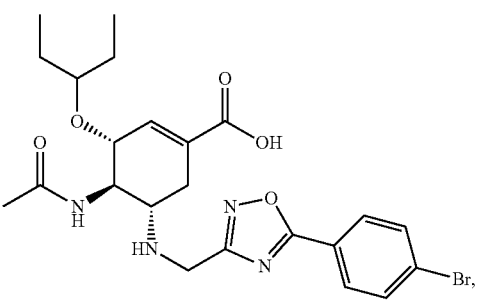
S5
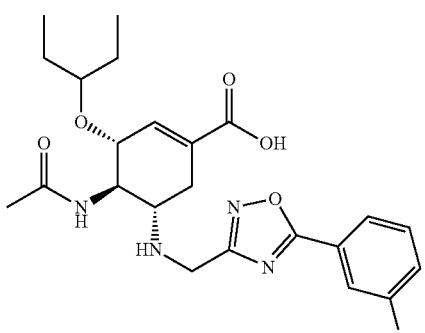
S6
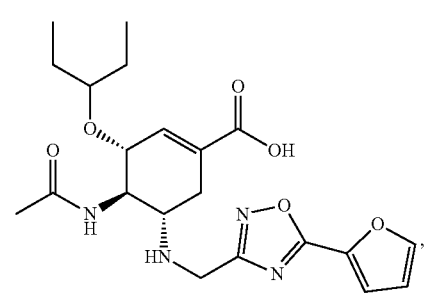
S7
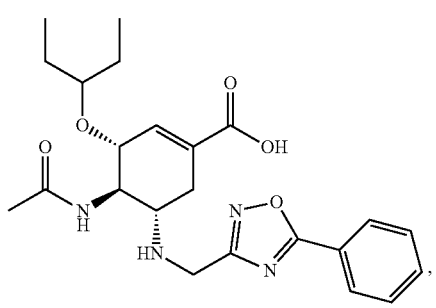
S8

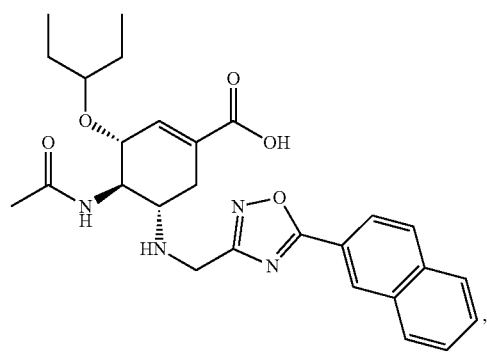

S19
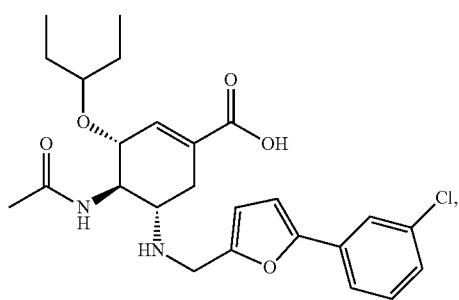
S20
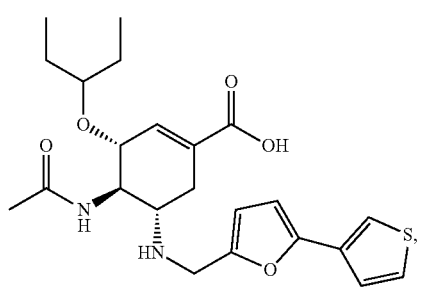
S21
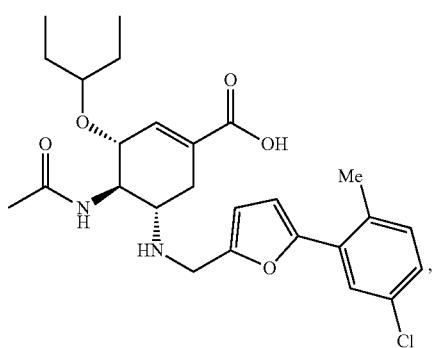
S22
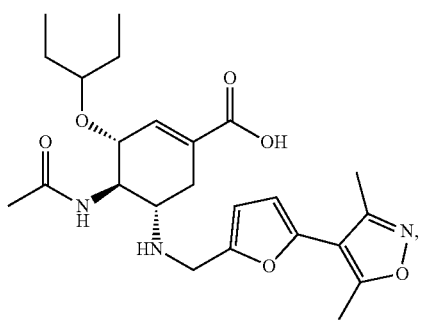
S23
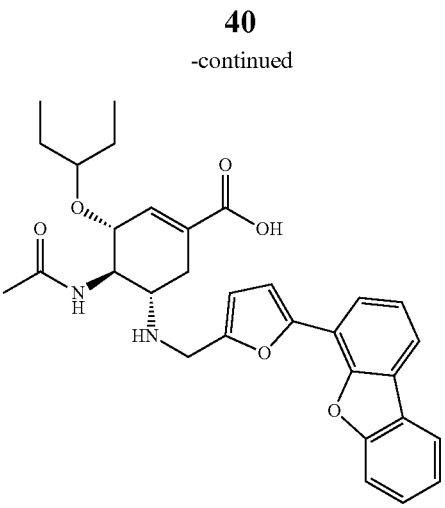
S24
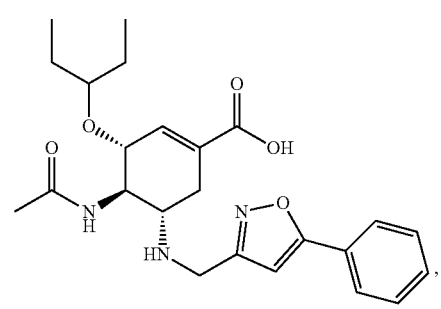
S25
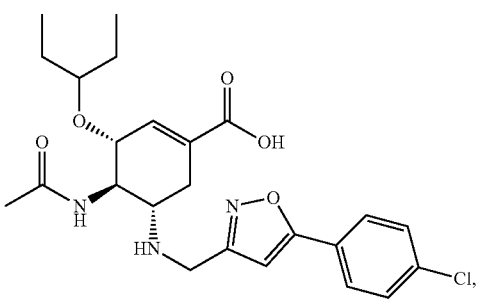
S26
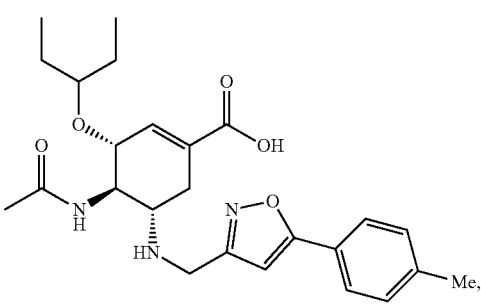
S27
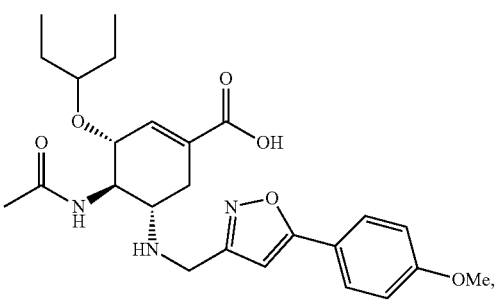

-continued
S28
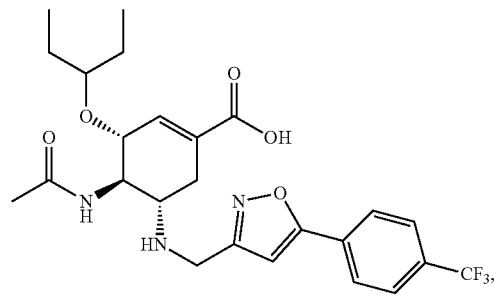
S29
S30
S31
OC-001
-continued
OC-002
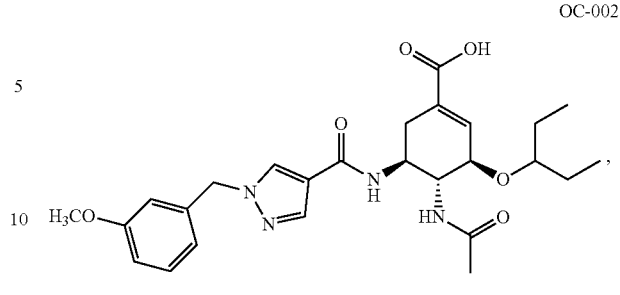
OC-003
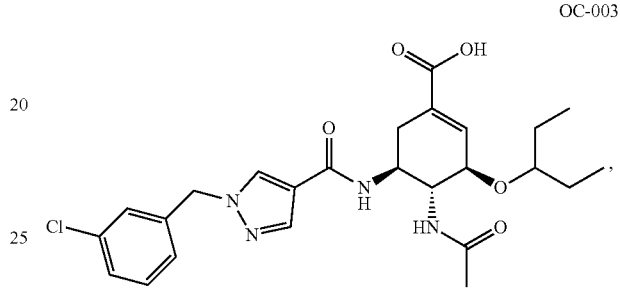
OC-004
OC-005
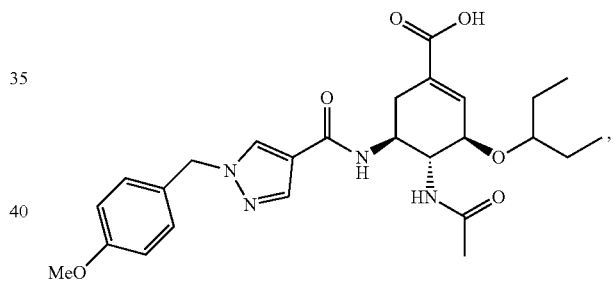
OC-006
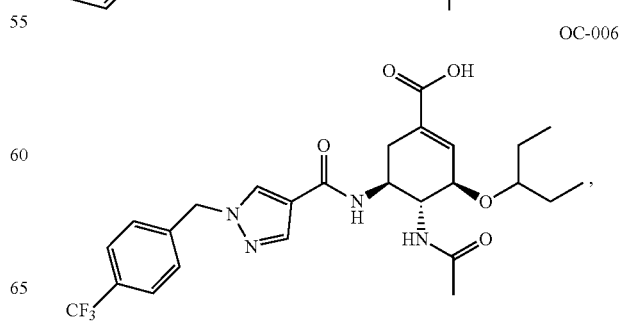

OC-007
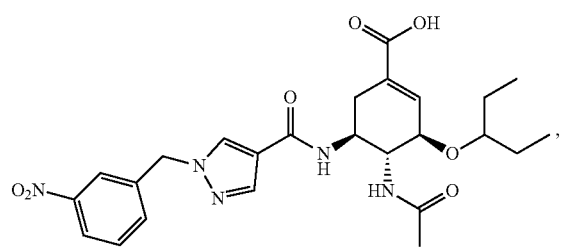
OC-008
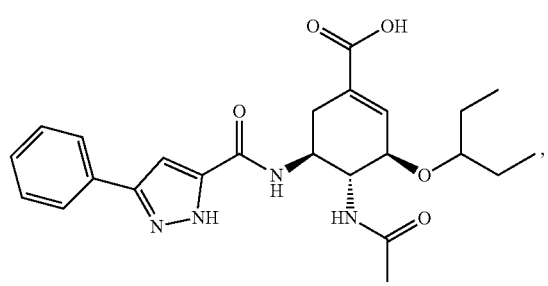
OC-009
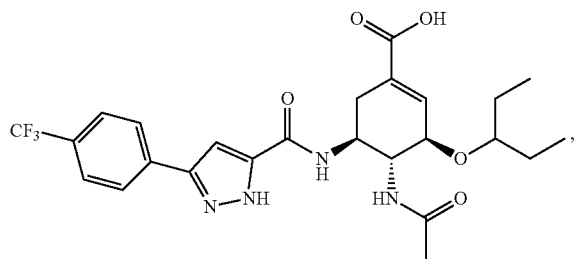
OC-010
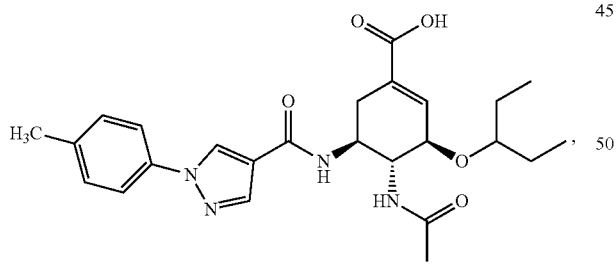
OC-011
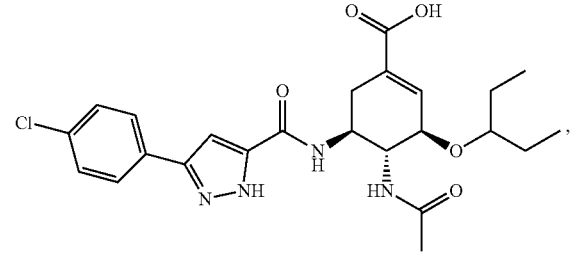
OC-012
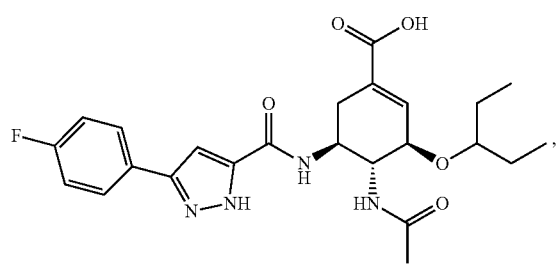
OC-013
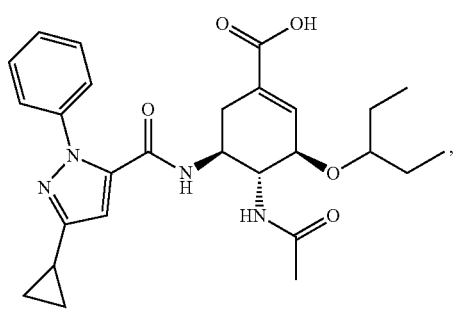
OC-014
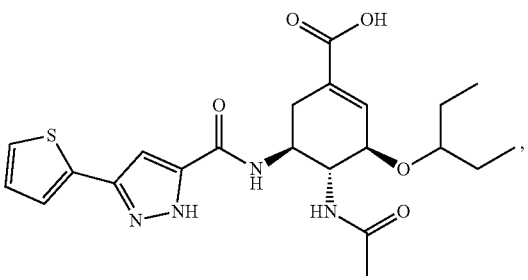
OC-015
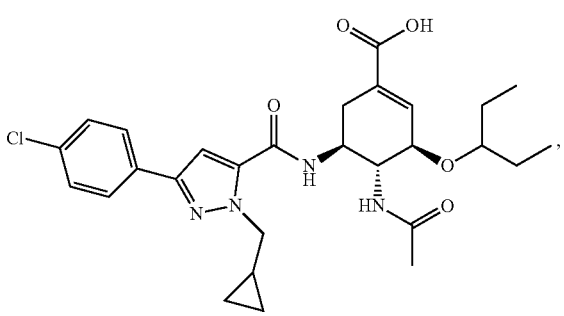
OC-016
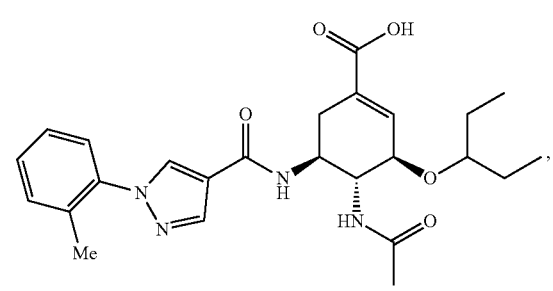

OC-017
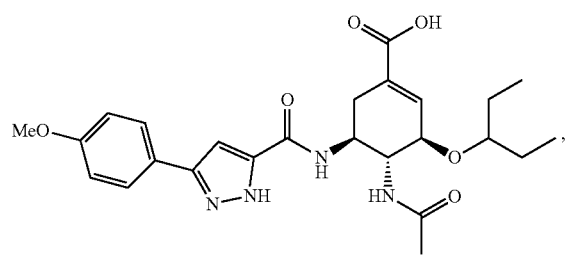
OC-018
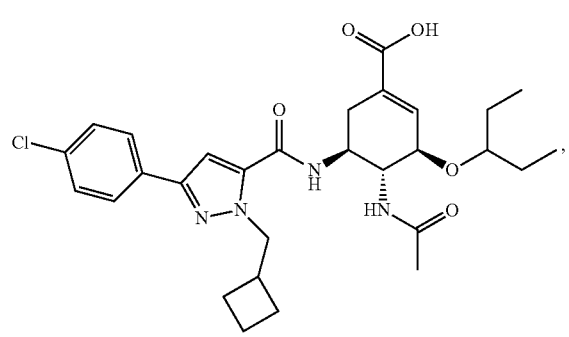
OC-0019
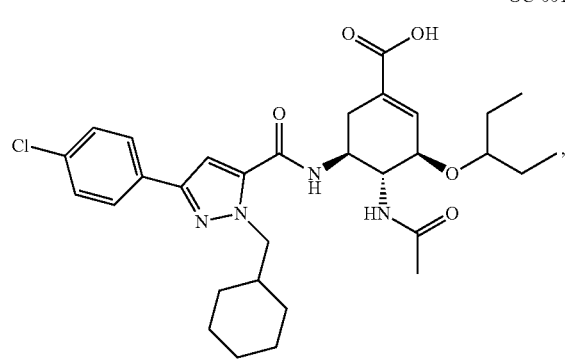
OC-0020
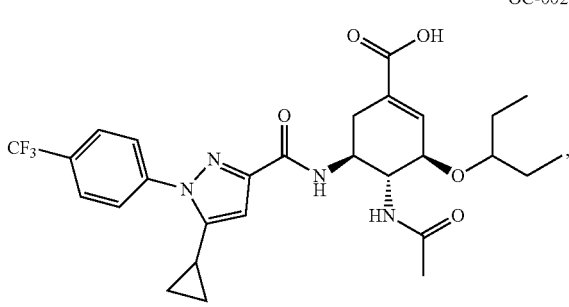
OC-0021
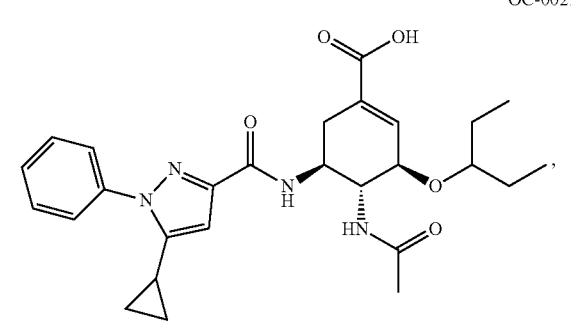
OC-022
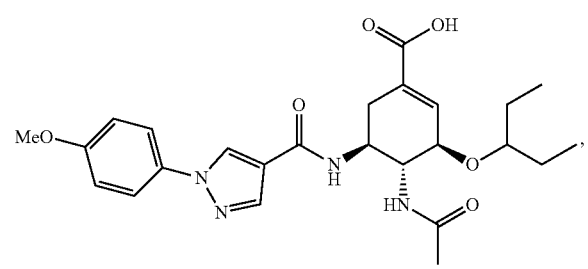
OC-023
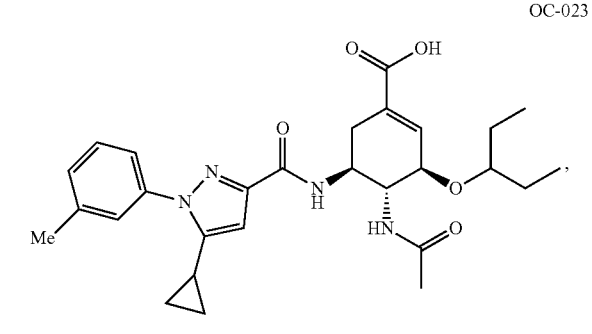
OC-024
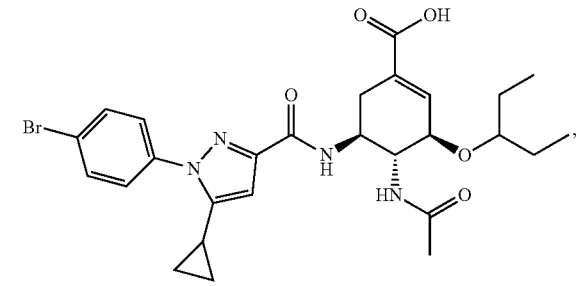
OC-025
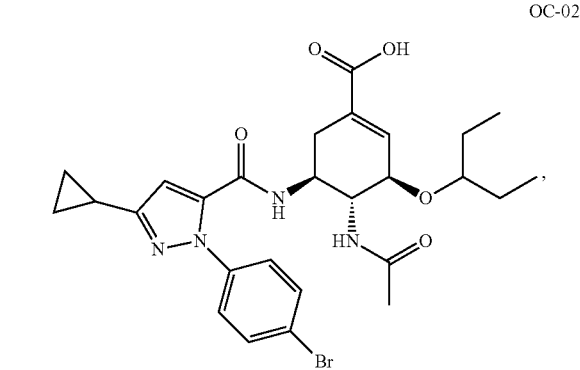
OC-026
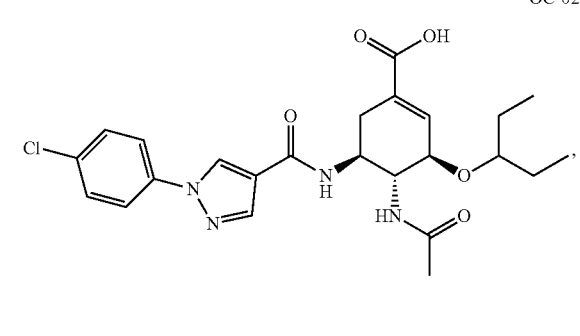

OC-027
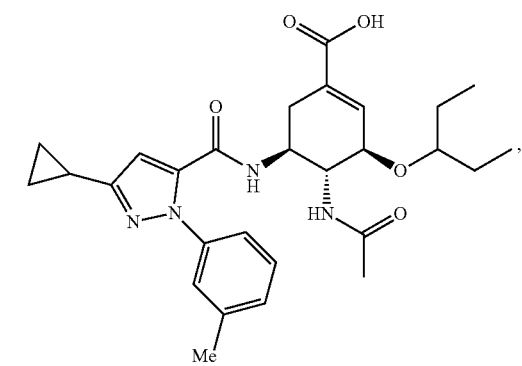
OC-028
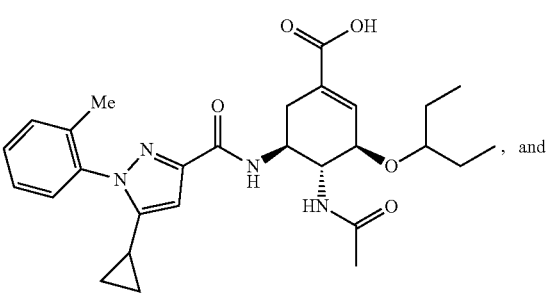, and
OC-029
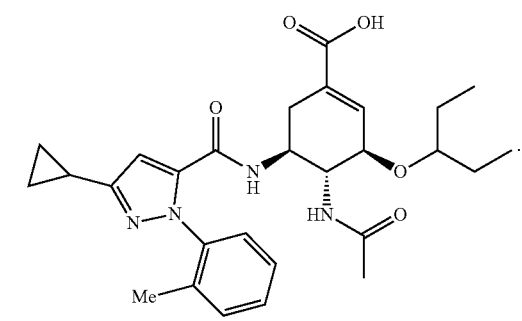
In certain embodiments, the compound is selected from:
S1
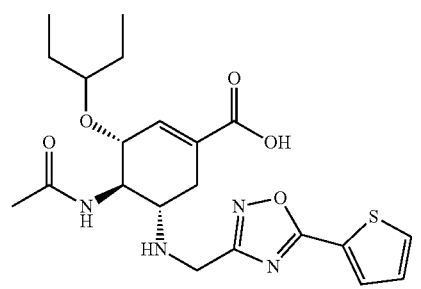
S2
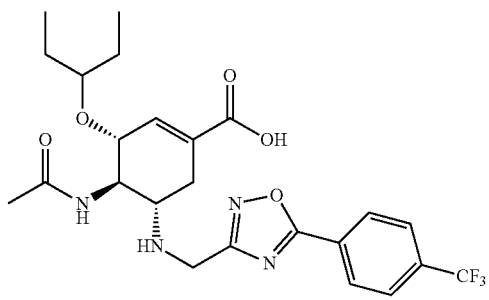
S3
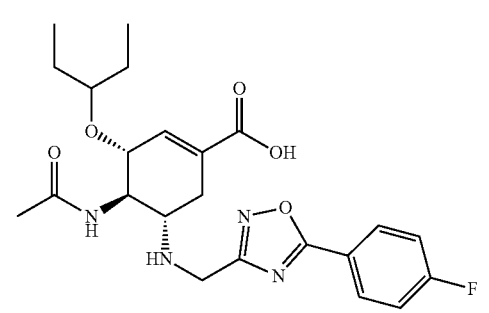
S4
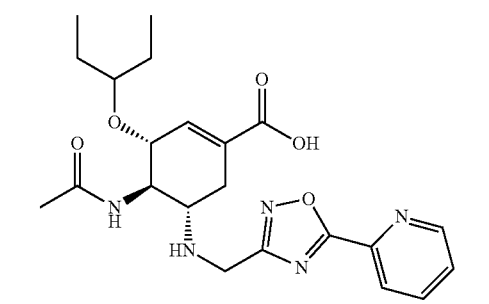
S5
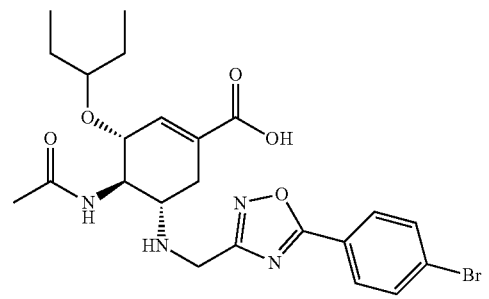
S6
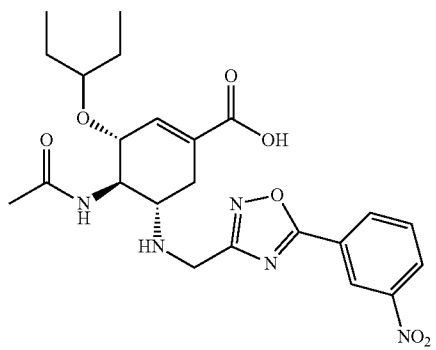

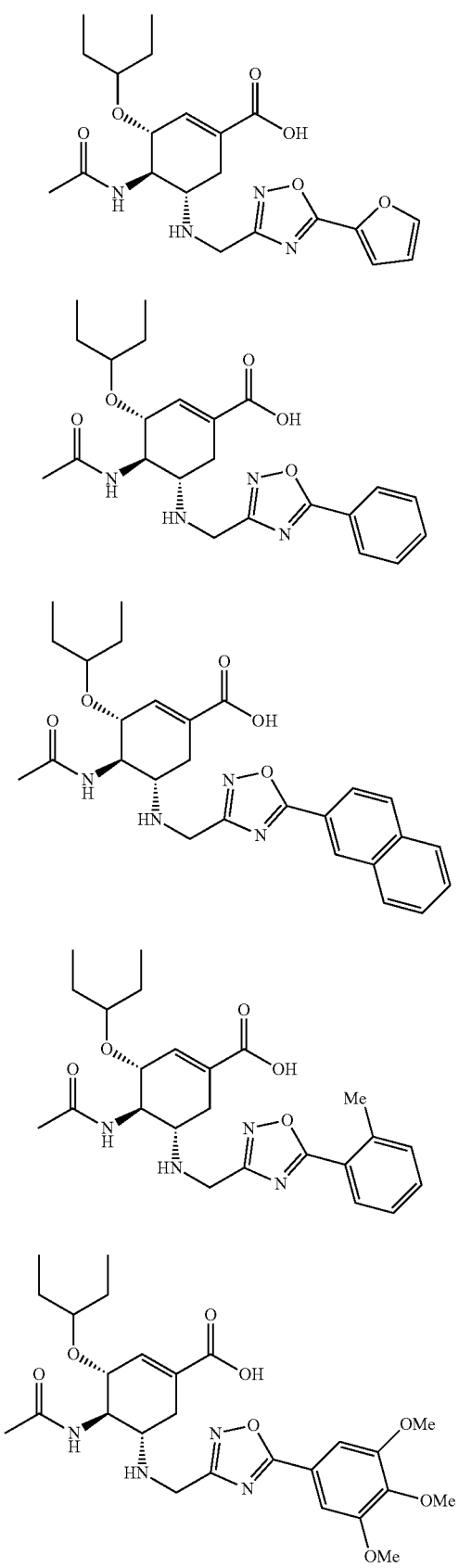
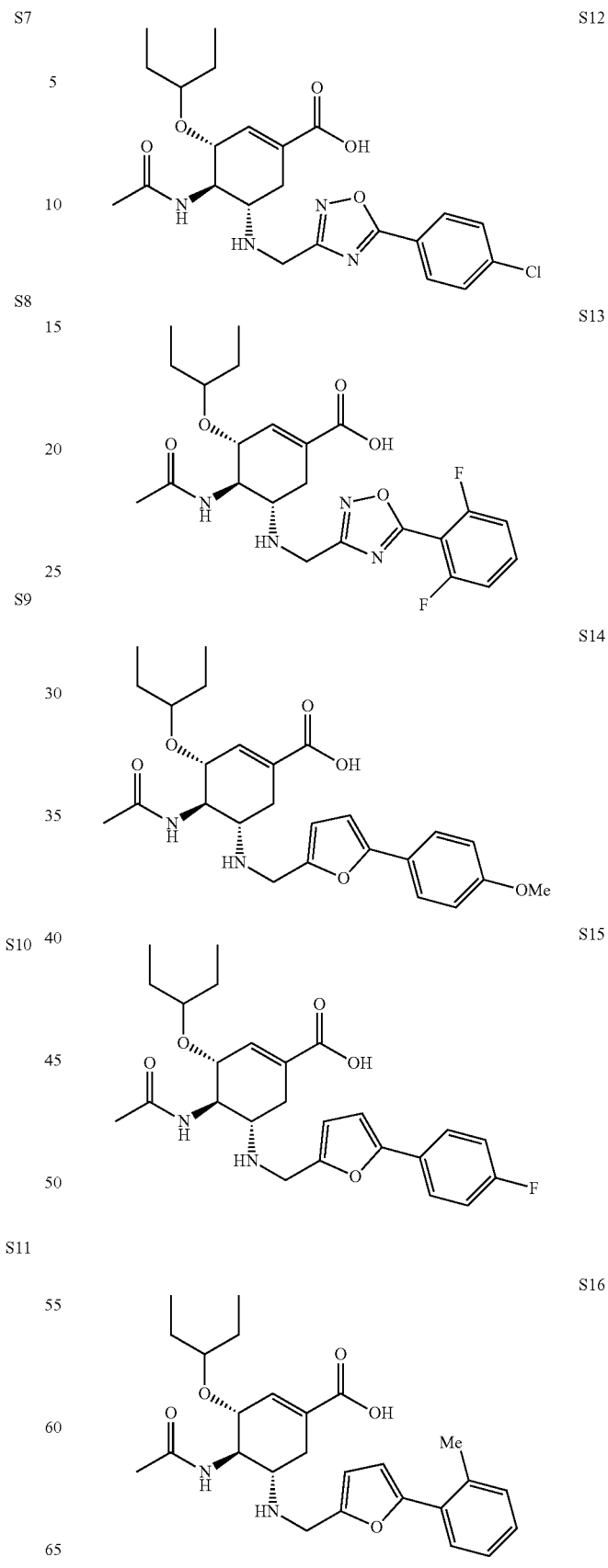

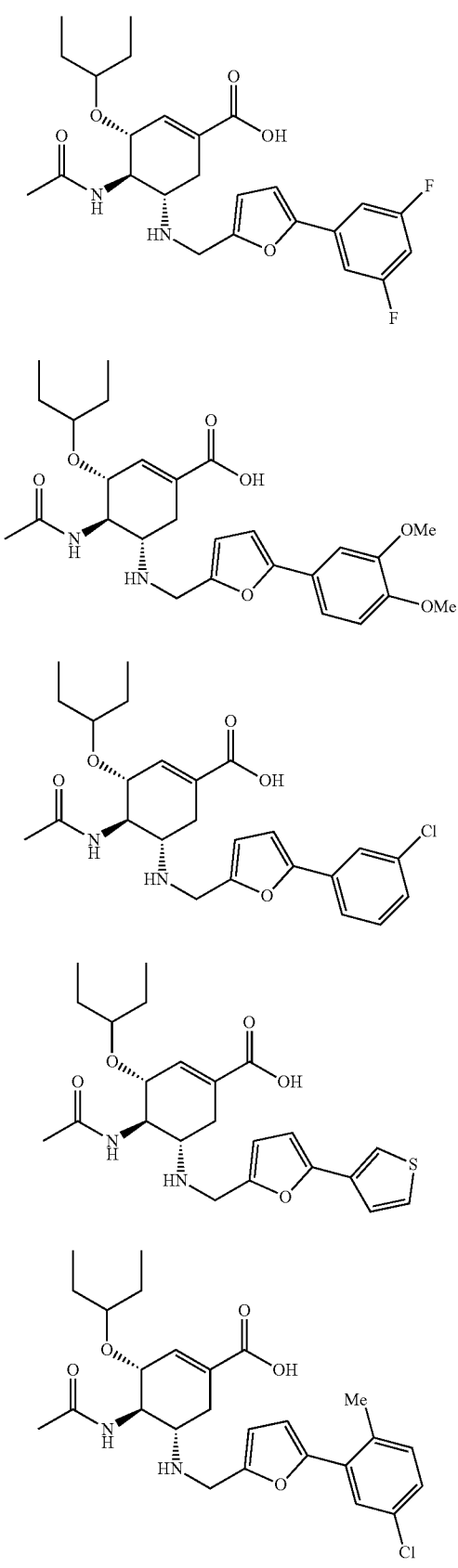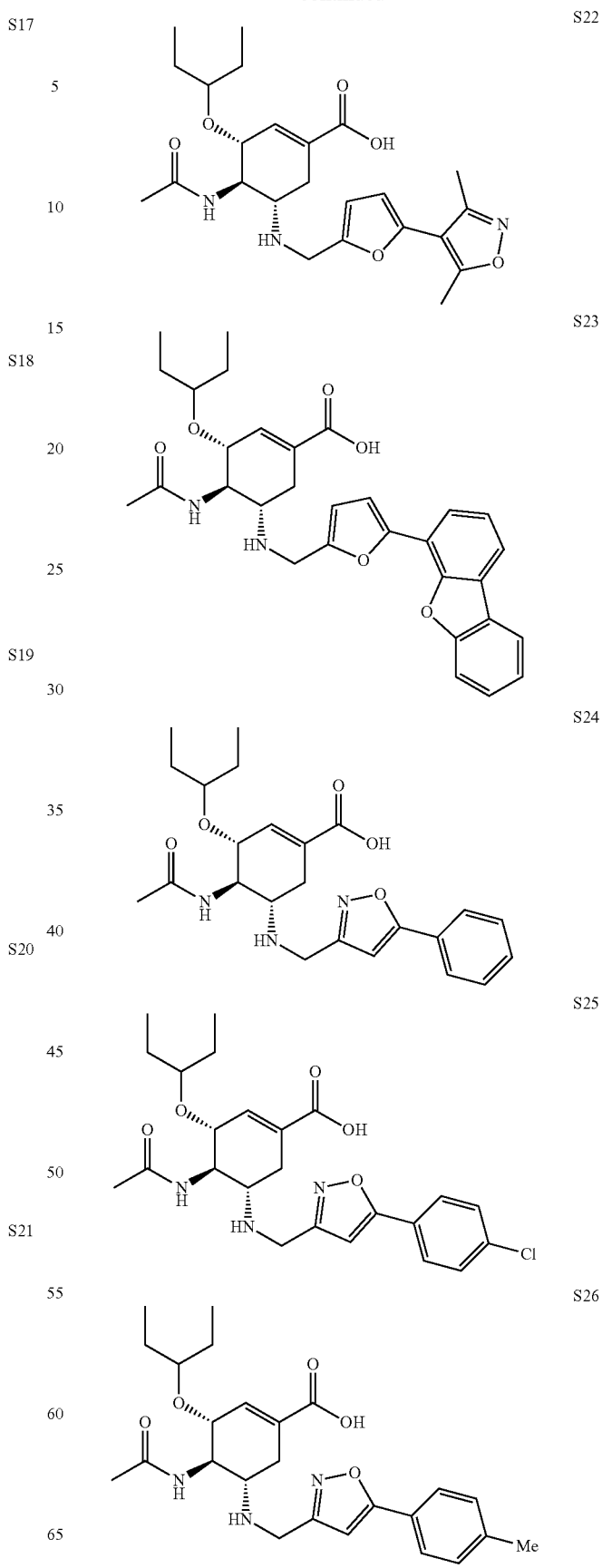

-continued

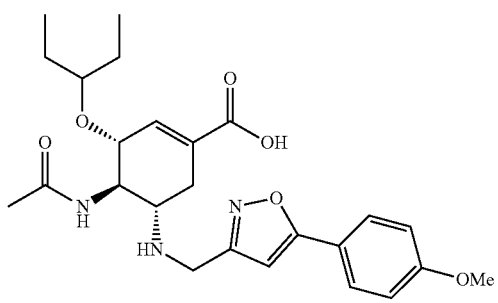
S27

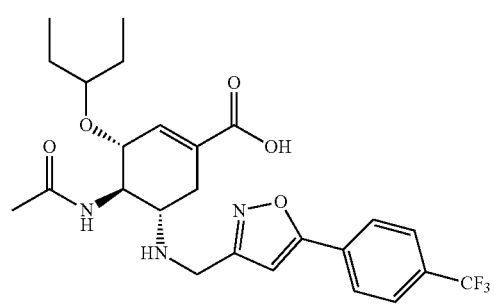
S28

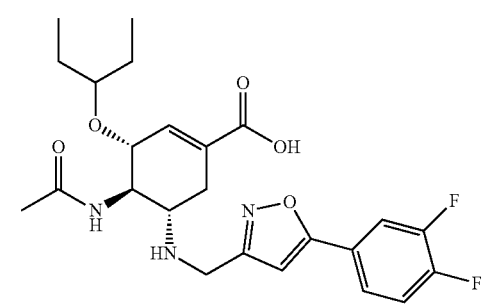
S29

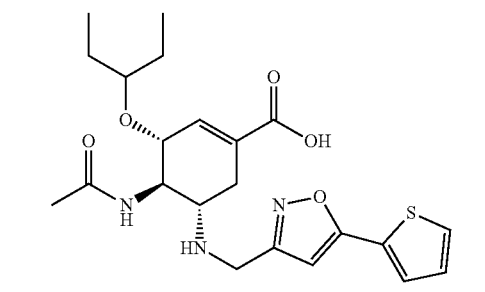
S30

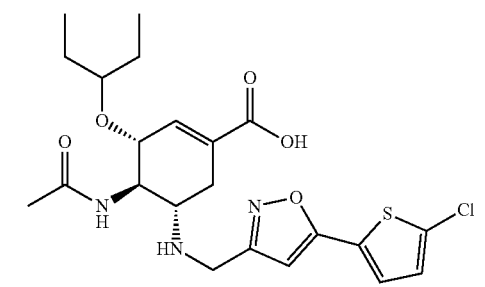
S31

The present disclosure also provides methods for preparing the compounds described herein. In certain embodiments, the method for preparing the compounds described herein comprises: contacting a compound of Formula IV:

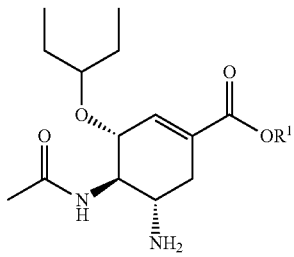
IV wherein $R^1$ is hydrogen, alkyl, alkenyl, alkynyl, cycloalkyl, heterocycloalkyl, aryl, or heteroaryl; with a compound Formula V:

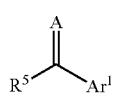
V wherein A is O, S, or $H_2$; $R^5$ is a leaving group; and $Ar^1$ is an optionally substituted 5 membered heteroaryl containing 1, 2, or 3 ring heteroatoms selected from the group consisting of O, C, N, P, S, and Se; or contacting the compound of Formula 3 with a compound Formula VI:

VI wherein $Ar^1$ is an optionally substituted 5 membered heteroaryl containing 1, 2, or 3 ring heteroatoms selected from the group consisting of O, C, N, P, S, and Se; and a reducing agent; thereby forming the compound described herein.

In instances in which A is O or S, the compound of Formula V can be prepared beforehand or in situ.

In instances in which the compound of formula V is prepared beforehand, the leaving group can be any leaving group known in the art, such as chloride, bromide, or iodide.

In instances in which the compound of Formula V is prepared in situ it can be prepared by the reaction of the corresponding carboxylic acid (wherein $R^5$ is OH) and a coupling agent optionally in the presence of a coupling additive. The coupling agent can be a carbodiimide, such as DCC, DIC, EDC, CIC, BMC, CPC, BDDC, PIC, PEC, and BEM, a uranium/aminium salt, such as HATU, HBTU, TATU, TBTU, HAPyU, TAPipU, HAPipU, HBPipU, HAMBU, HBMDU, HAMTU, 5,6-B(HATU), 4,5-B(HATU), HCTU, TCTU, and ACTU, phosphonium salts, such as AOP, BOP, PyAOP, PyBOP, PyOxm, PyNOP, PyFOP, NOP, and PyClock, immonium salts, such as BOMI, BDMP, BMMP, BPMP, and AOMP.

The coupling additive can be any coupling additive known in the art, such as HOBt, 6-NO2-HOBt, 6-Cl-HOBt, 6-CF3-HOBt, HOAt, HODhbt, HODhat, NHS, and Oxyma.

In instances in which A is $H_2$, $R^5$ can be any leaving group known in the art useful in primary amine alkylations. Such leaving groups are well known in the art. The selection of which is well within the skill of a person of ordinary skill in the art. Exemplary leaving groups for amine alkylations include, but are not limited to, chloride, bromide, iodide, mesylate, triflate, tosylate, nosylate, and the like.

Alternatively, in instances in which A is $H_2$, the compounds described herein can be prepared by reduction alkylation of the compound of Formula IV and an aldehyde (i.e., the compound of Formula V, wherein $R^5$ is H and A is O). In such instances, any reducing agent that is known to be useful as a reducing agent in reductive aminations can be used in the methods described herein. In certain embodiments, the reducing agent is NaCNBH3 or NABH4.

The step of contacting the compound of Formula IV with the compound of Formula V can take place in any solvent. The selection of the appropriate solvent can depend on the chemical structure of the starting materials and the nature of the chemical reaction required to prepare the compound described herein. The selection of the appropriate solvent is well within the skill of a person of ordinary skill in the art. The solvent can be an aprotic or protic organic solvent. In certain embodiments, the solvent is selected from the group consisting of alcohols, alkyl halides, ethers, esters, ketones, formamides, alkylnitriles, alkylsulfoxides, and aromatic solvents. Exemplary solvents include, but are not limited to, tetrahydrofuran, tetrahydropyran, dioxane, dichloromethane, dichloroethane, chloroform, dimethylformamide, dimethylsulfoxide, and mixtures thereof.

The step of contacting the compound of Formula IV with the compound of Formula V can be conducted in the presence of a base. The base can be an organic or inorganic Brønsted base. In certain embodiments, the base is an organic amine, metal hydroxide, metal carbonate, metal alkoxide, and mixtures thereof. Exemplary bases include, but are not limited to, Hunig's base, pyridine, pyrazine, trimethylamine, morpholine, N-methyl morpholine, piperdine, piperazine, pyrrolidine, DABCO, quinuclidine, TBD, DBU, DBN, DMAP, NaOH, CsOH, KOH, $Na_2CO_3$, $K_2CO_3$, $Cs_2CO_3$, and the like.

The methods described herein can comprise one or more additional synthetic steps before or after the steps described herein. Such synthetic steps may be necessary to prepare more complex compounds of Formula I. The one or more additional synthetic steps can include, but are not limited to, reductions, oxidations, substitution reactions, metal catalysed carbon-carbon forming reactions, alkylations, acylations, electrophilic aromatic substitution reactions, nucleophilic aromatic substitution reactions, hydrolysis reactions, condensation reactions, and the like.

In certain embodiments, the method of preparing the compound described herein are characterized as shown in Schemes 1-3.

Scheme 1

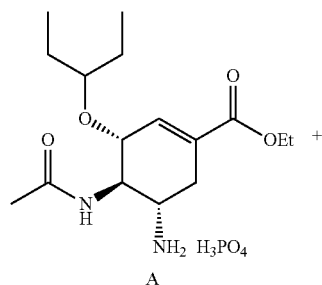

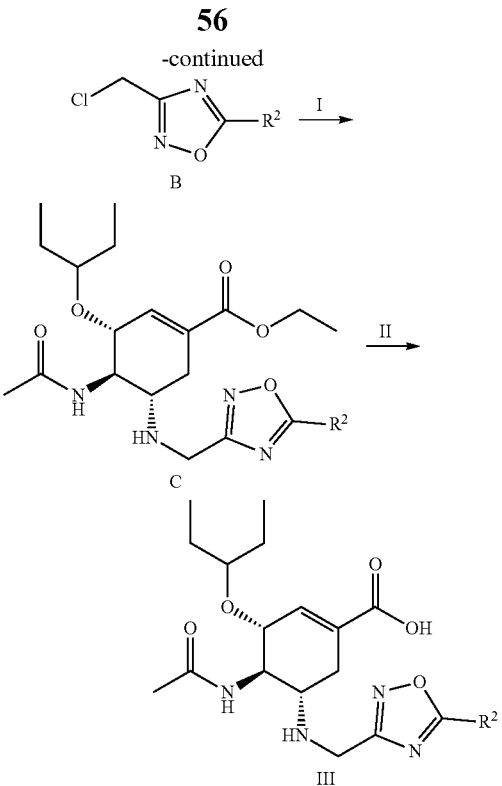

in which $R^2$ is as defined herein.

Oseltamivir phosphate (A) was reacted with oxadiazole methylene chloride (B in N, N-Dimethylformamide (DMF) with N, N-Diisopropylethylamine (DIPEA) to give C, followed by hydrolysis with sodium hydroxide (NaOH) to provide II.

Scheme 2

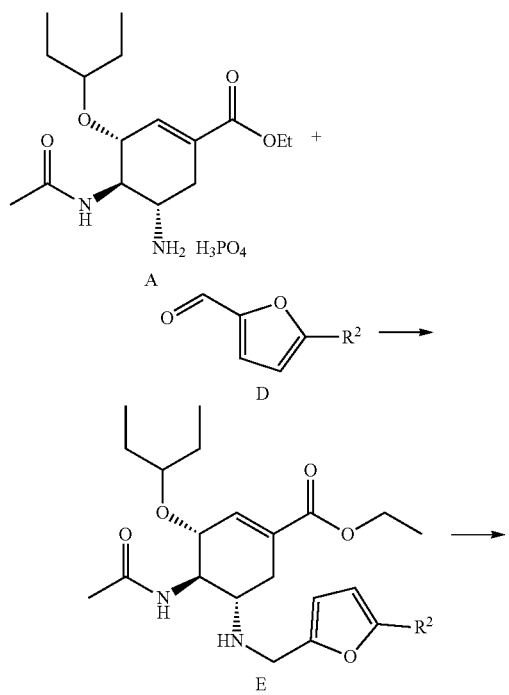

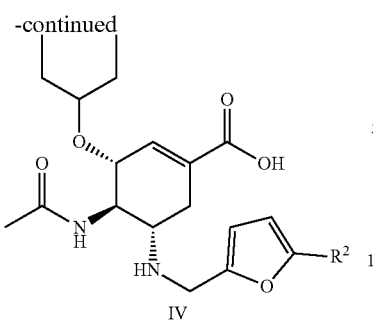

in which R² is defined above.

Oseltamivir phosphate (A) was reacted with the aldehyde (D) in the presence of Sodium triacetoborohydride to afford intermediate (E) which were hydrolyzed with NaOH to give compounds IV.

Scheme 3

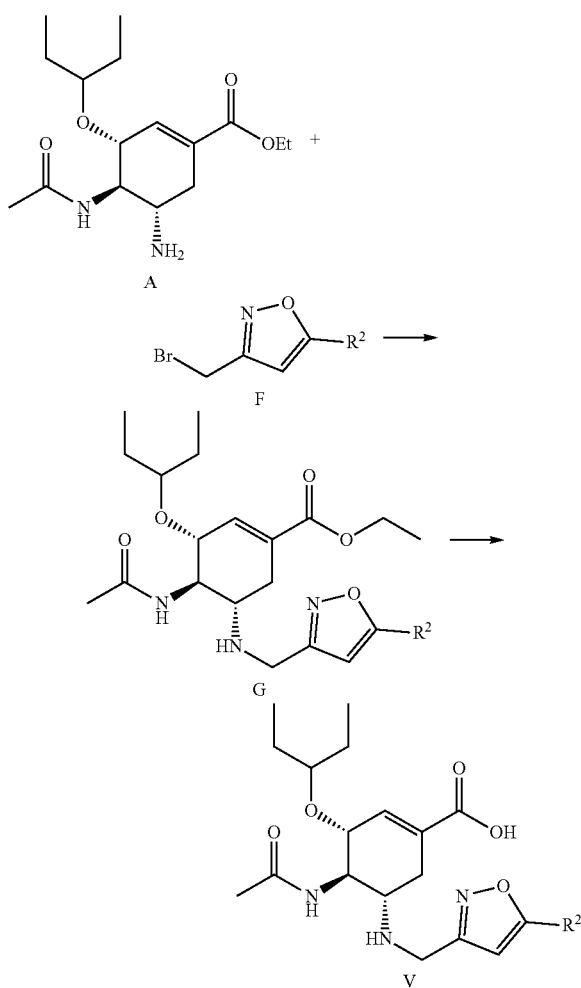

in which R² is defined above.

Oseltamivir phosphate (A) was reacted with F under 70° C. in DMF with DIPEA to provide G, which were hydrolyzed to give V.

The present disclosure also provides a pharmaceutical composition comprising one or more of the compounds described herein and at least one pharmaceutically acceptable excipient and/or pharmaceutically acceptable carrier.

The compounds described herein and their pharmaceutically acceptable salts can be administered to a subject either alone or in combination with pharmaceutically acceptable carriers or diluents in a pharmaceutical composition according to standard pharmaceutical practice. The compounds can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the compounds described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue.

As set out herein, certain embodiments of the compounds described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present disclosure. These salts can be prepared in situ in the administration vehicle or the dosage form manufacturing process, or by separately reacting a purified compounds of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the compounds include the step of bringing into association a compound described herein with the carrier and, optionally, one or more accessory ingredients. In general, the formulations are prepared by uniformly and intimately bringing into association a compounds described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more compounds described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The present disclosure therefore also relates to the compounds of the Formula I and/or their physiologically tolerable salts and/or their prodrugs for use as pharmaceuticals, to the use of the compounds of the Formula I and/or their physiologically tolerable salts and/or their prodrugs for the production of pharmaceuticals for the therapy and prophylaxis of the diseases.

The present disclosure furthermore relates to pharmaceutical compositions (or pharmaceutical preparations) which contain an efficacious dose of at least one compound of the Formula I and/or its physiologically tolerable salts and/or its prodrugs and a customary pharmaceutically acceptable carrier.

The compounds of the Formula I are inhibitors of neuraminidases. They have, for example, the ability to function as antiviral agents. The action of the compounds the Formula I can be demonstrated, for example, in an assay in which neuraminidases were used as the substrates. Details of such assay are given below.

Apart from use as antiviral agents, the compounds of the Formula I and their physiologically tolerable salts and their prodrugs can be used for example, as inhibitors of tumor growth and tumor metastasis, as anti-inflammatories, for the therapy bacterial infections, etc.

The present disclosure also provides methods for treating a viral infection. Treatment of the viral infection can occur in vitro. e.g., in a cell culture comprising the infected cells, or in vivo in a subject, such as a human. In certain embodiments, the method comprises administering a therapeutically effective amount of a compound described herein to the subject. In certain embodiments, the viral infection is an influenza viral infection.

The compounds, pharmaceutical compositions, and therapeutic methods described herein are useful for preventing, treating, or ameliorating infections caused by influenza viruses, including but not limited to: any of the subtypes of influenza A, influenza B, or influenza C.

In certain embodiments, the compounds, pharmaceutical compositions, and therapeutic methods disclosed herein are useful for preventing, treating, or ameliorating infections caused by influenza A viruses, including but not limited to, any of the strains of H1N1, H1N2, H1N3, H1N4, H1N5, H1N6, H1N7, H1N8, H1N9, H2N1, H2N2, H2N3, H2N4, H2N5, H2N6, H2N7, H2N8, H2N9, H3N1, H3N2, H3N3, H3N4, II3N5. H3N6, H3N7, H3N8, H3N9, H4N1, H5N2, H5N3, H5N4, H5N5, H5N6, H5N7, H5N8, H5N9, H6N1, II6N2, H6N3, H6N4, H6N5, H6N6, H6N7, H6N8, H6N9, H7N1, H7N2, H7N3, H7N4, H7N5, H7N6, H7N7, H7N8, H7N9, H8N1, H8N2, H8N3, H8N4, H8N5, H8N6, H8N7, H8N8, H8N9, H9N1, H9N2, H9N3, H9N4, H9N5. H9N6, H9N7, H9N8, H9N9, H10N1, H10N2, H10N3, H10N4, H10N5, H10N6, H10N7, H10N8, H10N9, H11N1, H11N2, H11N3, H11N4, H11N5, H11N6, H11N7, H11N8, H11N9, H12N1, H12N2, H12N3, H12N4, H12N5, H12N6, H12N7, H12N8, H12N9, H13N1, H13N2, H13N3, H13N4, H13N5, H13N6, H13N7, H13N8, H13N9, H14N1, H14N2, H14N3, H14N4, H14N5, H14N6, H14N7, H14N8, H14N9, H15N1, H15N2, H15N3, H15N4, H15N5, H15N6, H1N7, H15N8, and H15N9.

In certain embodiments, the compounds, pharmaceutical compositions, and therapeutic methods disclosed herein are useful for preventing, treating, or ameliorating infections caused by H1N1 and H3N2. In certain embodiments, the influenza virus is an oseltamivir-resistant influenza A virus.

In certain embodiments, the compounds described herein can be co-administered with one or more antivirals.

In certain embodiments, the compounds described herein can be co-administered with a second antiviral.

The compounds described herein can be administered according to therapeutic protocols well known in the art. It will be apparent to those skilled in the art that the administration of the compounds described herein and the second antiviral can be varied depending on the disease being treated and the known effects of the second antiviral on that disease. Also, in accordance with the knowledge of the skilled clinician, the therapeutic protocols (e.g., dosage amounts and times of administration) can be varied in view of the observed effects of the administered therapeutic agents (i.e., second antiviral) on the patient, and in view of the observed responses of the disease to the administered therapeutic agents.

Also, in general, compounds described herein and the second antiviral do not have to be administered in the same pharmaceutical composition, and may, because of different physical and chemical characteristics, have to be administered by different routes. For example, compounds described herein may be administered intravenously to generate and maintain good blood levels, while the second antiviral may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of second antiviral will depend upon the diagnosis of the attending physicians and their judgment of the condition of the patient and the appropriate treatment protocol.

A compound described and second antiviral may be administered concurrently (e.g., simultaneously, essentially simultaneously or within the same treatment protocol) or sequentially, depending upon the nature of the viral infection, the condition of the patient, and the actual choice of second antiviral to be administered in conjunction (i.e., within a single treatment protocol) with a compound described herein.

If a compound described herein and the second antiviral are not administered simultaneously or essentially simultaneously, then the optimum order of administration of the compound described herein and the second antiviral, may be different for different viral infections. Thus, in certain situations the compound described herein may be administered first followed by the administration of the second antiviral; and in other situations the second antiviral may be administered first followed by the administration of a compound described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the second antiviral.

may be administered first and then the treatment continued with the administration of a compound described herein followed, where determined advantageous, by the administration of the anti-viral, and so on until the treatment protocol is complete.

Thus, in accordance with experience and knowledge, the practicing physician can modify each protocol for the administration of a component (compound described herein and the second antiviral) of the treatment according to the individual patient's needs, as the treatment proceeds.

The disclosure is further illustrated by the following examples, which are not to be construed as limiting this disclosure in scope or spirit to the specific procedures herein described. It's to be understood that any embodiments listed in the examples section are embodiments of the oseltamivir derivatives, as such, are suitable for use in the methods and compositions described above.

Example 1

(3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1)

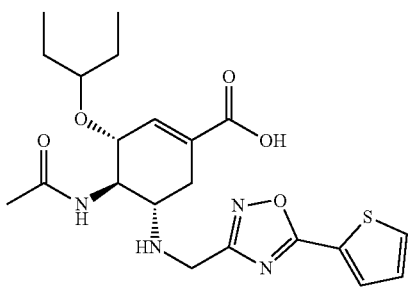

The preparation of S1 is illustrated in FIG. 1.

Synthesis of Intermediate 2

A round bottom flask was charged a magnetic stirring, chloroacetonitrile (132 mmol, 10 g), hydroxylamine (9.2 g, 132 mmol) and 100 ml water in ice bath. $Na_2CO_3$ was added portion wise to the mixture, then warm to room temperature. After 2 h, sodium chloride aqueous solution was added, extracted with $Et_2O$, combined organic phase, washed by NaCl solution and filtered, the filtration was evaporated, and the residue was dried in vacuum to provide the titled compound as white solid, 5 g, 35% yield.

Synthesis of Intermediate 3

To a solution of compound 2a (1 eq.) in acetone was added 2-thiophenecarbonyl chloride dropwise at 0° C. Subsequently, the mixture was warmed to room temperature. After 4 h, the volatiles were removed in vacuum and the residue was partitioned between water and EA, the organic phase was washed with brine and dried with anhydrous $Na_2SO_4$. The mixture was filtered, and the filtration was evaporated to afford crude product as pale-yellow solid.

Synthesis of Intermediate 4

Compound 3 and acetic acid were added to a round bottom flask and heated to reflux. When TLC indicated that the reaction was completed, it was cooled to r.t. and the solvents was removed in vacuum. $NaHCO_3$ aqueous solution was added to the residue, extracted by EA. The organic phase was combined and washed with brine and dried by anhydrous $Na_2SO_4$ and the crude mixture was evaporated and purified by column chromatography to provide the titled compound.

Synthesis of Intermediate 5

To a round-bottom flask were added Oseltamivir phosphate (1 eq), compound (4) (1.2 eq.) and DMF. DIPEA (3 eq.) was added at r.t, and then heated to 70° C. After 12 h, water was added to the reaction mixture followed by extracting with EA. The combined organic phase was washed with NaCl solution, dried by Na$_2$SO$_4$ and evaporated to provide the titled compounds.

Synthesis of S1

Compound (5) (1 eq.) was dissolved in methanol and water (v:v=5:1), NaOH (5 eq.) was added. The reaction mixture was heated to 50° C. overnight. Methanol was removed in vacuum and a small amount of water was added to the reaction mixture. The aqueous phase was washed by CH$_2$Cl$_2$ twice, then acidified to precipitate S1.

White solid. $^1$H NMR (400 MHz, DMSO) δ 8.08 (d, J=4.8 Hz, 1H), 8.01 (d, J=3.5 Hz, 1H), 7.75 (d, J=9.0 Hz, 1H), 7.42-7.25 (m, 1H), 6.60 (s, 1H), 3.99 (d, J=7.9 Hz, 1H), 3.87 (dd, J=31.2, 15.1 Hz, 2H), 3.64 (dd, J=18.7, 9.1 Hz, 1H), 3.35-3.30 (m, 2H), 2.79-2.65 (m, 2H), 1.85-2.06 (m, 1H), 1.84 (s, 3H), 1.35-1.45 (m, 4H), 0.83 (t, J=7.3 Hz, 3H), 0.78 (t, J=7.4 Hz, 3H). $^{13}$C NMR (101 MHz, DMSO) δ 171.07, 170.19, 170.14, 168.10, 137.64, 134.25, 132.95, 129.82, 129.66, 125.25, 81.29, 75.73, 54.80, 54.63, 41.38, 30.94, 26.10, 25.60, 23.48, 9.92, 9.38. HRMS (ESI, m/z) calcd for C$_{21}$H$_{27}$N$_4$O$_5$S, 447.1708 [M−H$^-$]; found, 447.1699.

Example 2

(3R,4R,5S)-4-acetamido-3-(pentan-3-yloxy)-5-(((5-(4-(trifluoromethyl)phenyl)-1,2,4-oxadiazol-3-yl)methyl)amino)cyclohex-1-ene-1-carboxylic acid (S2)

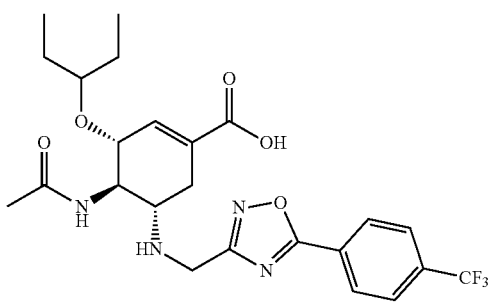

The same experimental procedure detailed in the preparation of (3R,4R,5S)-4-acetamido-3-(pentan-3-yloxy)-5-((5-(thiophen-2-yl)-1,2,4-oxadiazol-3-yl)methyl)amino)cyclohex-1-ene-1-carboxylic acid (S1) (Example 1) was used. 4-(Trifluoromethyl)benzoyl chloride was used to instead of 2-Thiophenecarbonyl chloride.

White solid. $^1$H NMR (400 MHz, DMSO) δ 8.33 (d, J=8.1 Hz, 2H), 8.02 (d. J=8.2 Hz, 2H), 7.72 (d, J=8.9 Hz, 1H), 6.38 (s, 1H), 3.93 (dd, J=34.1, 15.3 Hz, 3H), 3.62 (d, J=9.1 Hz, 2H), 3.30 (s, 1H), 2.72 (d, J=18.2 Hz, 2H), 2.02-1.89 (m, 1H), 1.48-1.30 (m, 4H), 0.83 (t, J=7.3 Hz, 3H), 0.77 (t, J=7.3 Hz, 4H). $^{13}$C NMR (101 MHz, DMSO) δ 174.2, 170.6, 170.2, 133.2, 132.9, 129.2, 127.7, 127.0 (q, J=3.6 Hz), 125.4, 122.7, 81.1, 76.2, 55.0, 41.4, 39.7, 39.5, 39.3, 31.6, 26.2, 25.6, 23.5, 9.9, 9.4. HRMS (ESI, m/z) calcd for C$_{24}$H$_{28}$F$_3$N$_4$O$_5$, 509.2017 [M−H$^-$]; found, 509.2009.

Example 3

(3R,4R,5S)-4-acetamido-5-(((5-(4-fluorophenyl)-1,2,4-oxadiazol-3-yl)methyl)amino)-3-(pentan-3-yloxy)cyclohex-1-ene-1-carboxylic acid (S3)

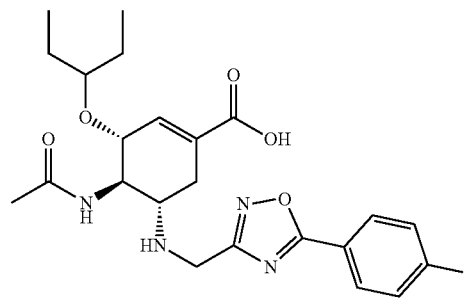

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 4-Fluorobenzoyl chloride was used to instead of 2-Thiophenecarbonyl chloride.

White solid. $^1$H NMR (400 MHz, DMSO) δ 8.18 (dd, J=8.5, 5.4 Hz, 2H), 7.76 (d, J=9.0 Hz, 1H), 7.49 (t, J=8.8 Hz, 2H), 6.60 (s, 1H), 3.99 (d, J=7.7 Hz, 1H), 3.90 (dd, J=29.6, 15.2 Hz, 2H), 3.65 (dd, J=18.2, 9.0 Hz, 1H), 2.81-2.65 (m, 2H), 2.01 (dd, J=16.3, 8.7 Hz, 1H), 1.40 (dd, J=11.6, 5.5 Hz, 4H), 0.83 (t, J=7.3 Hz, 3H), 0.78 (t, J=7.3 Hz, 3H). $^{13}$C NMR (101 MHz, DMSO) δ 174.54, 170.39, 170.13, 168.01, 166.57, 164.07, 137.69, 131.19, 131.10, 129.77, 120.76, 117.43, 117.21, 81.29, 75.71, 54.74, 54.66, 41.47, 30.90, 26.09, 25.60, 23.47, 9.91, 9.37. HRMS (ESI, m/z) calcd for C$_{23}$H$_{28}$FN$_4$O$_5$, 459.2049 [M−H$^-$]; found, 459.2035.

Example 4

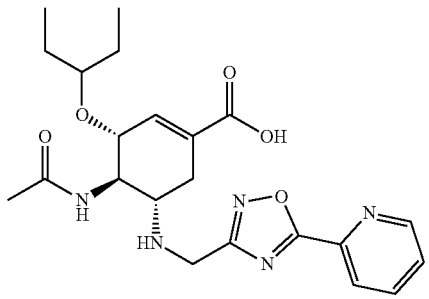

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. Picolinoyl chloride was used to instead of 2-Thiophenecarbonyl chloride.

White solid. $^1$H NMR (400 MHz, DMSO) δ 8.83 (d, J=4.5 Hz, 1H), 8.26 (d, J=7.8 Hz, 1H), 8.11 (td, J=7.8, 1.5 Hz, 1H), 7.71 (dd, J=7.1, 5.0 Hz, 1H), 7.66 (d, J=16.5 Hz, 1H), 7.01

(s, 1H), 6.28 (s, 1H), 3.83-4.05 (m, 3H), 3.64-3.57 (m, 1H), 3.25-3.33 (m, 1H), 2.78-2.60 (m, 2H), 1.92 (dd, J=17.5, 8.9 Hz, 1H), 1.82 (s, 3H), 1.44-1.33 (m, 4H), 0.83 (t, J=7.3 Hz, 3H), 0.77 (t, J=7.4 Hz, 3H). $^{13}$C NMR (101 MHz, DMSO) δ 174.4, 170.5, 170.1, 151.0, 143.5, 143.4, 138.6, 130.9, 127.8, 124.8, 80.9, 76.7, 55.3, 55.2, 41.5, 32.3, 26.2, 25.6, 23.5, 9.9, 9.4. HRMS (ESI, m/z) calcd for $C_{22}H_{28}N_5O_5$, 442.2096 [M−H$^-$]; found, 442.2090.

Example 5

(3R,4R,5S)-4-acetamido-5-(((5-(4-bromophenyl)-1,2,4-oxadiazol-3-yl)methyl)amino)-3-(pentan-3-yloxy)cyclohex-1-ene-1-carboxylic acid (S5)

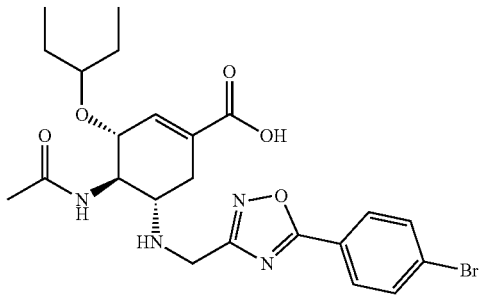

S5

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 4-Bromobenzoyl chloride was used to instead of 2-Thiophenecarbonyl chloride.

White solid. $^1$H NMR (400 MHz, DMSO) δ 12.57 (s, 1H), 8.05 (d, J=8.4 Hz, 2H), 7.87 (d, J=8.4 Hz, 2H), 7.80 (d, J=6.9 Hz, 1H), 6.62 (s, 1H), 4.02 (s, 3H), 3.69 (s, 1H), 2.93-2.65 (m, 2H), 2.09 (s, 1H), 1.84 (s, 3H), 1.50-1.31 (m, 4H), 0.84 (t, J=7.3 Hz, 3H), 0.78 (t, J=7.3 Hz, 3H). 13C NMR. HRMS (ESI, m/z) calcd for $C_{23}H_{28}BrN_4O_5$, 519.1249 [M−H$^-$]; found, 519.1234.

Example 6

(3R,4R,5S)-4-acetamido-5-(((5-(3-nitrophenyl)-1,2,4-oxadiazol-3-yl)methyl)amino)-3-(pentan-3-yloxy)cyclohex-1-ene-1-carboxylic acid (S6)

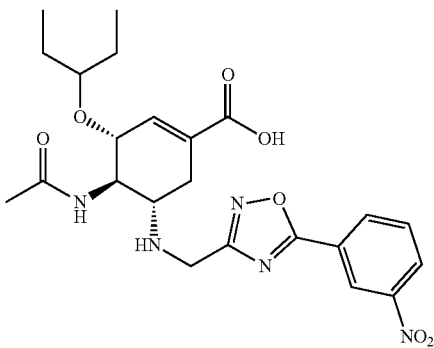

S6

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 3-Nitrobenzoyl chloride was used to instead of 2-Thiophenecarbonyl chloride.

White solid. $^1$H NMR (400 MHz, DMSO) δ 8.80 (s, 1H), 8.61-8.47 (m, 2H), 7.97 (t, J=7.9 Hz, 2H), 6.64 (s, 1H), 4.15 (d, J=46.0 Hz, 3H), 3.80 (s, 1H), 3.28-2.91 (m, 2H), 2.81 (d, J=15.5 Hz, 1H), 2.27 (s, 1H), 1.87 (s, 3H), 1.33-1.52 (m, 4H), 0.81 (dt, J=20.5, 7.2 Hz, 6H). $^{13}$C NMR (101 MHz, DMSO) δ 174.0, 170.6, 167.7, 148.8, 137.9, 134.3, 132.1, 128.8, 128.2, 125.1, 122.9, 81.4, 75.2, 55.0, 53.3, 26.1, 25.6, 23.6, 9.9, 9.4. HRMS (ESI, m/z) calcd for $C_{23}H_{28}N_5O_7$, 486.1994 [M−H$^-$]; found, 486.1985.

Example 7

(3R,4R,5S)-4-acetamido-5-(((5-(furan-2-yl)-1,2,4-oxadiazol-3-yl)methyl)amino)-3-(pentan-3-yloxy)cyclohex-1-ene-1-carboxylic acid (S7)

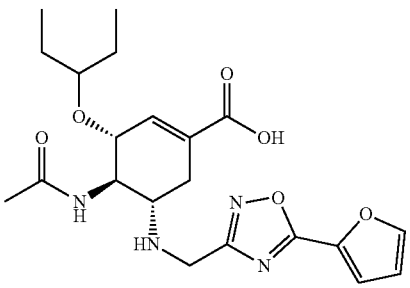

S7

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. Furan-2-carbonyl chloride was used to instead of 2-Thiophenecarbonyl chloride.

White solid, $^1$H NMR (400 MHz, DMSO) δ 8.13 (s, 1H), 7.76 (d, J=8.9 Hz, 1H), 7.55 (d, J=3.0 Hz, 1H), 7.04 (s, 1H), 6.84 (s, 1H), 6.43 (s, 1H), 3.93 (s, 1H), 3.92-3.79 (m, 2H), 3.61 (d, J=9.0 Hz, 1H), 3.30 (d, J=4.8 Hz, 1H), 2.77-2.62 (m, 2H), 2.02-1.90 (m, 1H), 1.82 (s, 3H), 1.38 (s, 5H), 0.83 (d, J=6.9 Hz, 3H), 0.76 (t, J=7.1 Hz, 3H). $^{13}$C NMR (101 MHz, DMSO) δ 170.2, 170.0, 169.7, 167.3, 148.6, 139.7, 133.9, 133.2, 117.7, 113.5, 81.1, 76.2, 55.1, 55.0, 41.3, 31.8, 26.2, 25.6, 23.4, 9.9, 9.4. HRMS (ESI, m/z) calcd for $C_{21}H_{27}N_4O_6$, 431.1936 [M−H$^-$]; found, 431.1930.

Example 8

(3R,4R,5S)-4-acetamido-3-(pentan-3-yloxy)-5-(((5-phenyl-1,2,4-oxadiazol-3-yl)methyl)amino)cyclohex-1-ene-1-carboxylic acid (S8)

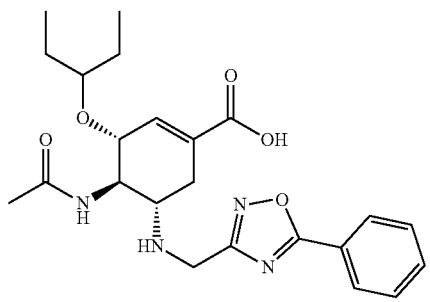

S8

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. Benzoyl chloride was used to instead of 2-Thiophenecarbonyl chloride.

White solid. $^1$H NMR (400 MHz, DMSO) δ 8.12 (d, J=7.3 Hz, 2H), 7.76 (d, J=9.1 Hz, 1H), 7.71 (d, J=7.3 Hz, 1H), 7.64 (t, J=7.5 Hz, 2H), 7.04 (s, 1H), 6.54 (s, 1H), 3.91 (dd, J=32.1, 15.1 Hz, 3H), 3.64 (d, J=9.3 Hz, 1H), 3.33-3.30 (m, 1H), 2.73 (dd, J=17.6, 7.4 Hz, 2H), 2.00 (dd, J=18.4, 10.7 Hz, 1H), 1.83 (s, 3H), 1.47-1.28 (m, 4H), 0.82 (dd, J=14.4, 7.0 Hz, 3H), 0.77 (d, J=7.4 Hz, 3H). $^{13}$C NMR (101 MHz, DMSO) δ 175.4, 170.4, 170.1, 168.7, 136.3, 133.6, 131.1, 130.0, 128.2, 124.0, 81.2, 75.9, 54.9, 54.8, 41.5, 31.2, 26.1, 25.6, 23.5, 9.9, 9.4. HRMS (ESI, m/z) calcd for $C_{23}H_{29}N_4O_5$, 441.2143 [M−H$^-$]; found, 441.2136.

Example 9

(3R,4R,5S)-4-acetamido-5-(((5-(naphthalen-2-yl)-1,2,4-oxadiazol-3-yl)methyl)amino)-3-(pentan-3-yloxy)cyclohex-1-ene-1-carboxylic acid (S9)

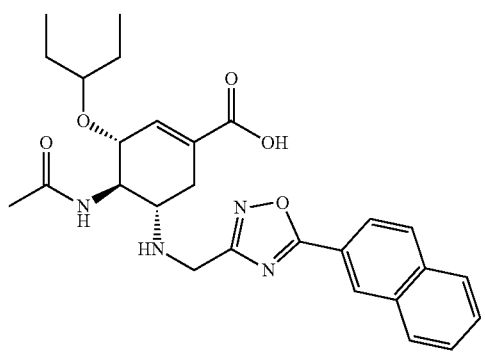

S9

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 2-naphthoyl chloride was used to instead of 2-Thiophenecarbonyl chloride.

White solid. $^1$H NMR (400 MHz, DMSO) δ 8.81 (s, 1H), 8.17 (dt, J=15.3, 8.2 Hz, 3H), 8.06 (d, J=7.9 Hz, 1H), 7.78 (d, J=9.0 Hz, 1H), 7.75-7.64 (m, 2H), 6.62 (s, 1H), 4.00 (s, 1H), 3.95 (q, J=13.6 Hz, 2H), 3.67 (dd, J=18.3, 9.2 Hz, 1H), 2.85-2.70 (m, 2H), 2.04 (ddd, J=11.7, 8.1, 5.8 Hz, 1H), 1.84 (s, 3H), 1.48-1.30 (m, 4H), 0.83 (t, J=7.3 Hz, 3H), 0.78 (t, J=7.3 Hz, 3H). $^{13}$C NMR (101 MHz, DMSO) δ 175.5, 170.5, 170.2, 168.0, 137.9, 135.2, 132.8, 129.8, 129.7, 129.6, 129.4, 129.3, 128.4, 127.93, 124.0, 121.3, 81.3, 75.7, 54.8, 54.7, 41.6, 30.9, 26.1, 25.6, 23.5, 9.9, 9.4. HRMS (ESI, m/z) calcd for $C_{27}H_{31}N_4O_5$, 491.23 [M−H$^-$]; found, 491.2288.

Example 10

(3R,4R,5S)-4-acetamido-3-(pentan-3-yloxy)-5-(((5-(o-tolyl)-1,2,4-oxadiazol-3-yl)methyl)amino)cyclohex-1-ene-1-carboxylic acid (S10)

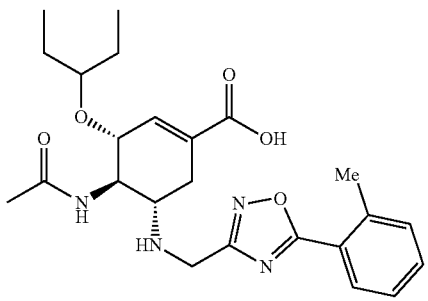

S10

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 2-Methylbenzoyl chloride was used to instead of 2-Thiophenecarbonyl chloride.

White solid. $^1$H NMR (400 MHz, DMSO) δ 8.04 (d, J=7.7 Hz, 1H), 7.78 (d, J=9.1 Hz, 1H), 7.57 (t, J=7.2 Hz, 1H), 7.48 (d, J=7.6 Hz, 1H), 7.44 (t, J=7.7 Hz, 1H), 6.59 (s, 1H), 4.01 (s, 1H), 3.99-3.90 (m, 2H), 3.66 (d, J=9.4 Hz, 1H), 3.33 (s, 1H), 2.83-2.69 (m, 2H), 2.65 (s, 3H), 2.02 (dd, J=17.0, 9.3 Hz, 1H), 1.83 (s, 3H), 1.50-1.32 (m, 4H), 0.83 (t, J=7.4 Hz, 3H), 0.78 (t, J=7.4 Hz, 3H). $^{13}$C NMR (101 MHz, DMSO) δ 175.89, 170.10, 169.91, 168.17, 138.91, 137.39, 133.03, 132.45, 130.25, 130.05, 127.09, 123.25, 81.27, 75.75, 54.76, 54.72, 41.50, 30.93, 26.10, 25.59, 23.42, 21.80, 9.92, 9.37. HRMS (ESI, m/z) calcd for $C_{24}H_{31}N_4O_5$, 455.23 [M−H$^-$]; found, 455.2312.

Example 11

(3R,4R,5S)-4-acetamido-3-(pentan-3-yloxy)-5-(((5-(3,4,5-trimethoxyphenyl)-1,2,4-oxadiazol-3-yl)methyl)amino)cyclohex-1-ene-1-carboxylic acid (S11)

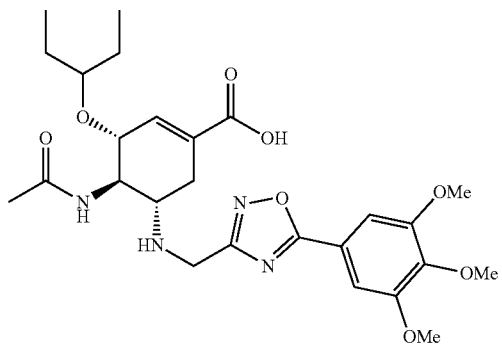

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 3,4,5-Trimethoxybenzoyl chloride was used to instead of 2-Thiophenecarbonyl chloride.

White solid. $^1$H NMR (400 MHz, DMSO) δ 7.77 (d, J=9.0 Hz, 1H), 7.38 (s, 2H), 6.59 (s, 1H), 3.99 (d, J=8.0 Hz, 1H), 3.93 (d, J=15.3 Hz, 2H), 3.89 (s, 6H), 3.77 (s, 3H), 3.66 (dd, J=18.8, 9.0 Hz, 1H), 3.36-3.29 (m, 1H), 2.78-2.66 (m, 2H), 2.02 (dd, J=17.4, 9.3 Hz, 1H), 1.85 (s, 3H), 1.33-1.50 (m, 4H), 0.83 (t, J=7.3 Hz, 3H), 0.78 (t, J=7.4 Hz, 3H). $^{13}$C NMR (101 MHz, DMSO) δ 175.23, 170.40, 170.11, 168.12, 153.90, 141.99, 137.46, 129.98, 119.08, 105.60, 81.28, 75.73, 60.75, 56.67, 54.94, 54.63, 41.60, 30.95, 26.10, 25.60, 23.48, 9.92, 9.38. HRMS (ESI, m/z) calcd for $C_{26}H_{35}N_4O_8$, 531.246 [M–H$^-$]; found, 531.2468.

Example 12

(3R,4R,5S)-4-Acetamido-5-(((5-(4-chlorophenyl)-1,2,4-oxadiazol-3-yl)methyl)amino)-3-(pentan-3-yloxy)cyclohex-1-ene-1-carboxylic acid (S12)

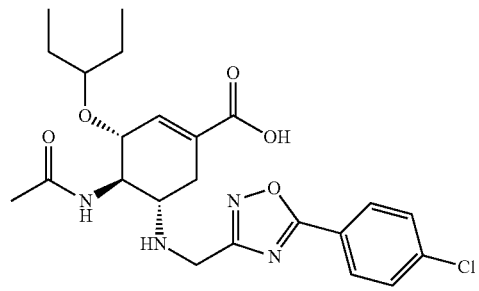

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 4-Chlorobenzoyl chloride was used to instead of 2-Thiophenecarbonyl chloride.

White solid. $^1$H NMR (400 MHz, DMSO) δ 8.13 (d, J=6.7 Hz, 2H), 7.84 (s, 1H), 7.74 (d, J=6.6 Hz, 2H), 6.63 (s, 1H), 4.04 (s, 3H), 3.73 (s, 1H), 2.92 (s, 1H), 2.76 (d, J=17.1 Hz, 1H), 2.15 (s, 1H), 1.84 (s, 3H), 1.41 (s, 4H), 0.90-0.69 (m, 6H). $^{13}$C NMR (101 MHz, DMSO) δ 174.72, 170.39, 167.79, 138.66, 137.96, 136.03, 131.61, 130.28, 130.13, 129.21, 124.40, 122.71, 81.38, 75.46, 54.90, 54.02, 29.48, 26.07, 25.57, 23.56, 9.89, 9.37. HRMS (ESI, m/z) calcd for $C_{23}H_{28}ClN_4O_5$, 475.1754 [M–H$^-$]; found, 475.1762.

Example 13

(3R,4R,5S)-4-acetamido-5-(((5-(2,6-difluorophenyl)-1,2,4-oxadiazol-3-yl)methyl)amino)-3-(pentan-3-yloxy)cyclohex-1-ene-1-carboxylic acid (S13)

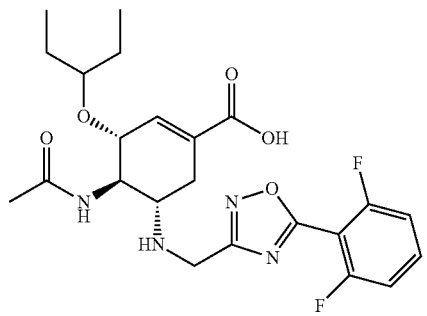

The same experimental procedure detailed in the preparation of (3R,4R,5S)-4-acetamido-3-(pentan-3-yloxy)-5-(((5-(thiophen-2-yl)-1,2,4-oxadiazol-3-yl)methyl)amino)cyclohex-1-ene-1-carboxylic acid (S1) (Example 1) was used. 2,6-Difluorobenzoyl chloride was used to instead of 2-Thiophenecarbonyl chloride.

White solid. $^1$H NMR (400 MHz, DMSO) δ 7.89-7.77 (m, 2H), 7.43 (t, J=9.0 Hz, 2H), 6.62 (s, 1H), 4.11-3.93 (m, 3H), 3.69 (dd, J=18.7, 9.1 Hz, 1H), 3.37-3.31 (m, 1H), 2.85 (s, 1H)), 2.73 (dd, J=17.4, 4.2 Hz, 1H), 2.08 (t, J=12.2 Hz, 1H), 1.83 (s, 3H), 1.49-1.35 (m, 4H), 0.83 (t, J=7.3 Hz, 3H), 0.78 (t, J=7.4 Hz, 3H). $^{13}$C NMR (101 MHz, DMSO) δ 170.21, 169.93, 168.24, 167.90, 160.5 (d, J=259.2 Hz), 160.3 (d, J=259.4 Hz), 137.99, 136.31 (d, J=11.1 Hz), 129.45, 113.6 (d, J=21.2 Hz), 113.5 (d, J=21.2 Hz), 103.0 (d, J=16.3 Hz), 81.33, 75.65, 54.84, 54.45, 41.30, 30.53, 26.07, 25.57, 23.41, 9.91, 9.36. HRMS (ESI, m/z) calcd for $C_{23}H_{27}F_2N_4O_5$, 477.1955 [M–H$^-$]; found, 477.1965.

Example 14

(3R,4R,5S)-4-Acetamido-5-(((5-(4-methoxyphenyl)furan-2-yl)methyl)amino)-3-(pentan-3-yloxy)cyclohex-1-ene-1-carboxylic acid (S14)

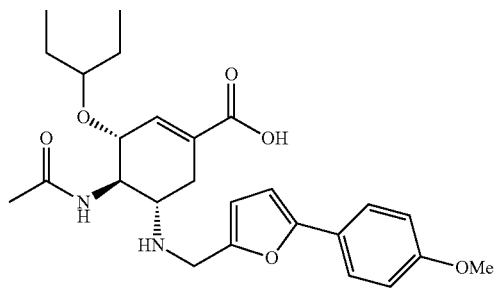

Figure 2:
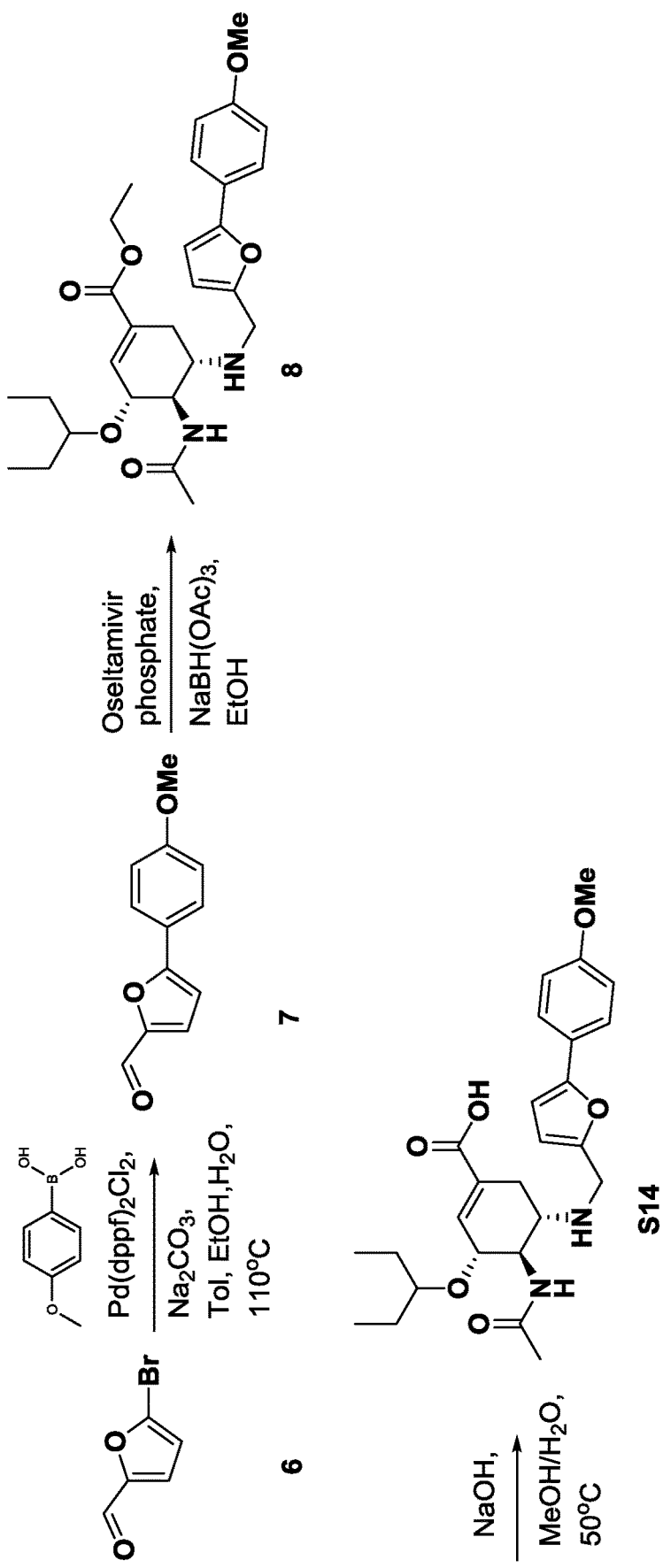
FIG. 2 depicts a schematic illustration of the preparation of the compound S2.

Preparation of S14 is illustrated in FIG. 2.

Synthesis of Intermediate 7

5-Bromofuran-2-carbaldehyde (175 mg, 1 mmol), (4-Methoxyphenyl)boronic acid (1 mmol, 1 equiv), Pd(dppf)$_2$Cl$_2$·DCM (16 mg, 2% equiv), Na$_2$CO$_3$ (318 mg, 3 mmol, 3 equiv) were added to a Shrenk flask with 6 ml of Toluene, 1.5 ml H$_2$O and 1.5 ml EtOH. The reaction mixture was charged with N$_2$ and heated at 110° C. overnight. The solution was extracted with EtOAc and the combined extracts were dried over Na$_2$SO$_4$. Chromatographic purification gave the titled compounds.

Synthesis of Intermediate 8

To a solution of oseltamvir phosphate (123 mg, 0.3 mmol) and 5-(4-methoxyphenyl)furan-2-carbaldehyde (0.36 mmol, 1.2 equiv) in 10 ml ethanol, NaBH(OAc)$_3$ (318 mg, 1.5 mmol) was slowly added. The mixture was stirred at room temperature overnight and then concentrated. To the residue, 20 ml saturated NaHCO$_3$ solution was added, and the mixture was extracted with EtOAc. The combined extracts were dried over anhydrous Na$_2$SO$_4$ and purified by chromatograph to give the products.

Synthesis of S14

Compound 8 (1 eq.) was dissolved in methanol and water (v:v=5:1), NaOH (5 eq.) was added. The reaction mixture was heated to 50° C. overnight. Methanol was removed in vacuum and a small amount of water was added to the reaction mixture. The aqueous phase was washed by CH$_2$Cl$_2$ twice, then acidified to precipitate the target compounds.

White solid. $^1$H NMR (400 MHz, DMSO) δ 7.81 (d, J=9.0 Hz, 1H), 7.59 (d, J 8.7 Hz, 2H), 6.97 (d, J=8.7 Hz, 2H), 6.68 (d, J=3.1 Hz, 1H), 6.61 (s, 1H), 6.29 (d, J=3.1 Hz, 1H), 4.00 (d, J=7.8 Hz, 1H), 3.80 (d, J=18.1 Hz, 4H), 3.74-3.63 (m, 2H), 3.34 (dt, J=10.7, 5.3 Hz, 1H), 2.84-2.65 (m, 2H), 2.02 (dd, J=16.9, 9.2 Hz, 1H), 1.85 (s, 3H), 1.33-1.52 (m, 4H), 0.73-0.89 (m, 6H). $^{13}$C NMR (101 MHz, DMSO) δ 170.08, 168.13, 158.96, 154.01, 152.50, 137.76, 129.85, 125.11, 123.98, 114.72, 109.10, 105.01, 81.28, 75.78, 55.63, 54.72, 54.71, 43.17, 30.93, 26.10, 25.61, 23.47, 9.92, 9.39. HRMS (ESI, m/z) calcd for C$_{26}$H$_{33}$N$_2$O$_6$, 469.2344 [M−H]$^-$; found, 469.235.

Example 15

(3R,4R,5S)-4-Acetamido-5-(((5-(4-fluorophenyl)furan-2-yl)methyl)amino)-3-(pentan-3-yloxy)cyclohex-1-ene-1-carboxylic acid (S15)

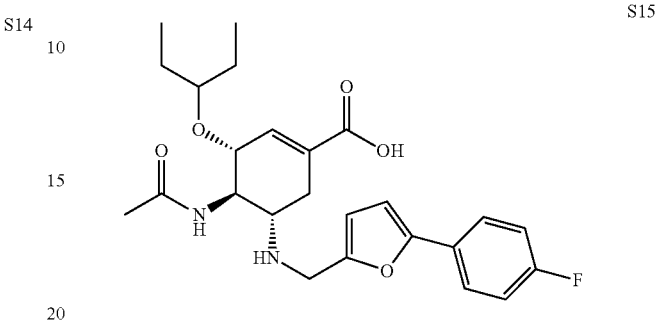

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. (4-Fluorophenyl)boronic acid was used to instead of (4-Methoxyphenyl)boronic acid.

White solid. 1H NMR (400 MHz, DMSO) δ 7.81 (d, J=8.9 Hz, 1H), 7.75-7.52 (m, 2H), 7.25 (t, J=8.5 Hz, 2H), 6.83 (s, 1H), 6.60 (s, 1H), 6.33 (s, 1H), 3.99 (s, 1H), 3.77 (dd, J=36.1, 15.0 Hz, 2H), 3.67 (d, J=9.2 Hz, 1H), 3.34 (s, 1H), 2.73 (dd, J=23.4, 11.8 Hz, 2H), 2.01 (dd, J=16.1, 9.2 Hz, 1H), 1.85 (s, 3H), 1.40 (dd, J=11.0, 5.5 Hz, 4H), 0.90-0.66 (m, 6H). $^{13}$C NMR (101 MHz, DMSO) δ 170.07, 164.9 (d, J=245.1 Hz), 154.99, 151.50, 137.63, 129.96, 127.7 (d, J=2.9 Hz), 125.6 (d, J=8.1 Hz), 116.2 (d, J=22.0 Hz), 109.26, 106.70, 81.26, 75.78, 54.73, 43.15, 40.62, 40.41, 40.20, 40.00, 39.79, 39.58, 39.37, 30.97, 26.11, 25.61, 23.47, 9.92, 9.39. HRMS (ESI, m/z) calcd for C$_{25}$H$_{30}$FN$_2$O$_5$, 457.2144 [M−H]$^-$; found, 457.2152.

Example 16

(3R,4R,5S)-4-Acetamido-3-(pentan-3-yloxy)-5-(((5-(o-tolyl)furan-2-yl)methyl)amino)cyclohex-1-ene-1-carboxylic acid (S16)

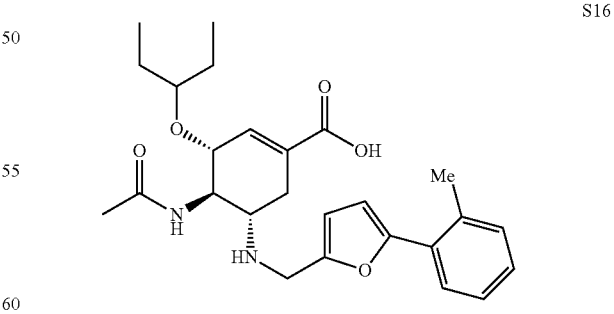

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. o-Tolylboronic acid was used to instead of (4-Methoxyphenyl)boronic acid.

White solid. $^1$H NMR (400 MHz, DMSO) δ 7.80 (d, J=9.0 Hz, 1H), 7.64 (d, J=7.4 Hz, 1H), 7.31-7.18 (m, 3H), 6.66-6.58 (m, 2H), 6.37 (d, J=3.0 Hz, 1H), 4.01 (d, J=7.8 Hz, 1H), 3.79 (dd, J=39.2, 14.8 Hz, 2H), 3.68 (dd, J=18.7, 9.3 Hz, 1H), 3.38-3.30 (m, 1H), 2.65-2.85 (m, 2H), 2.44 (s, 3H), 2.02 (dd, J=17.2, 9.1 Hz, 1H), 1.85 (s, 3H), 1.33-1.50 (m, 4H), 0.84 (t, J=7.5 Hz, 3H), 0.79 (t, J=7.4 Hz, 3H). $^{13}$C NMR (101 MHz, DMSO) δ 170.05, 168.15, 154.51, 151.89, 137.69, 134.07, 131.66, 130.17, 129.90, 127.66, 126.65, 126.51, 110.07, 108.99, 81.27, 75.79, 54.76, 54.67, 43.09, 30.93, 26.10, 25.60, 23.45, 22.06, 9.92, 9.39. HRMS (ESI, m/z) calcd for $C_{26}H_{33}N_2O_5$, 453.2395 [M−H$^-$]; found, 453.2404.

Example 17

(3R,4R,5S)-4-Acetamido-5-(((5-(3,5-difluorophenyl)furan-2-yl)methyl)amino)-3-(pentan-3-yloxy)cyclohex-1-ene-1-carboxylic acid (S17)

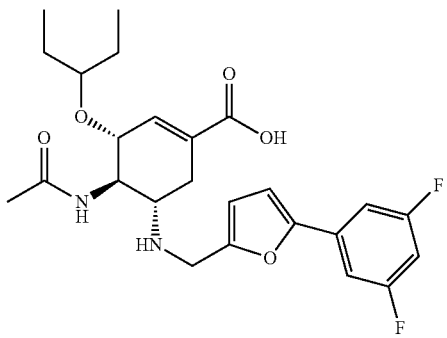

S17

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. (3,5-Difluorophenyl)boronic acid was used to instead of (4-Methoxyphenyl)boronic acid.

White solid. $^1$H NMR (400 MHz, DMSO) δ 7.79 (d, J=9.0 Hz, 1H), 7.37 (d, J=6.9 Hz, 2H), 7.10 (dd, J=18.8, 6.2 Hz, 2H), 6.61 (s, 1H), 6.39 (d, J=2.9 Hz, 1H), 4.01 (d, J=7.6 Hz, 1H), 3.79 (dd, J=35.1, 15.0 Hz, 2H), 3.67 (dd, J=18.3, 9.1 Hz, 1H), 3.30-3.40 (m, 1H), 2.83-2.62 (m, 2H), 2.02 (dd, J=16.8, 9.1 Hz, 1H), 1.86 (s, 3H), 1.33-1.50 (m, 4H), 0.90-0.74 (m, 6H). $^{13}$C NMR (101 MHz, DMSO) δ 170.0, 168.1, 163.4 (d, J=245.9 Hz), 163.3 (d, J=246.4 Hz), 156.2, 150.1, 137.8, 134.2, 134.1, 134.0, 129.7, 109.7 (d, J=8.3 Hz), 106.5 (d, J=27.5 Hz), 102.6 (d, J=26.2 Hz), 81.3, 75.7, 54.7, 54.6, 43.0, 30.8, 26.1, 25.6, 23.4, 9.9, 9.4. HRMS (ESI, m/z) calcd for $C_{25}H_{29}F_2N_2O_5$, 475.205 [M−H$^-$]; found, 475.2060.

Example 18

(3R,4R,5S)-4-Acetamido-5-(((5-(3,4-dimethoxyphenyl)furan-2-yl)methyl)amino)-3-(pentan-3-yloxy)cyclohex-1-ene-1-carboxylic acid (S18)

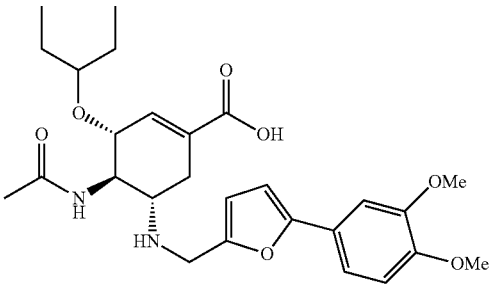

S18

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. (3,4-Dimethoxyphenyl)boronic acid was used to instead of (4-Methoxyphenyl)boronic acid.

White solid. $^1$H NMR (400 MHz, DMSO) δ 7.98 (d, J=6.6 Hz, 1H), 7.25 (s, 2H), 7.04-6.93 (m, 1H), 6.80 (d, J=2.7 Hz, 1H), 6.65 (s, 1H), 6.51 (s, 1H), 3.95-4.22 (m, 3H), 3.86 (d, J=13.3 Hz, 1H), 3.82 (s, 3H), 3.78 (s, 3H), 3.33-3.42 (m, 1H), 3.10 (s, 1H), 2.88 (d, J=16.5 Hz, 1H), 2.35 (s, 1H), 1.89 (s, 3H), 1.48-1.36 (m, 4H), 0.77-0.89 (m, 6H). $^{13}$C NMR (101 MHz, DMSO) δ 170.64, 167.60, 153.69, 149.55, 149.08, 137.96, 128.86, 123.84, 116.70, 112.67, 112.00, 108.02, 105.56, 81.47, 75.30, 56.14, 56.10, 54.54, 52.99, 41.32, 28.47, 26.08, 25.58, 23.68, 9.83, 9.34. HRMS (ESI, m/z) calcd for $C_{27}H_{35}N_2O_7$, 499.245 [M−H$^-$]; found, 499.2459.

Example 19

(3R,4R,5S)-4-Acetamido-5-(((5-(3-chloropentyl)furan-2-yl)methyl)amino)-3-(pentan-3-yloxy)cyclohex-1-ene-1-carboxylic acid (S19)

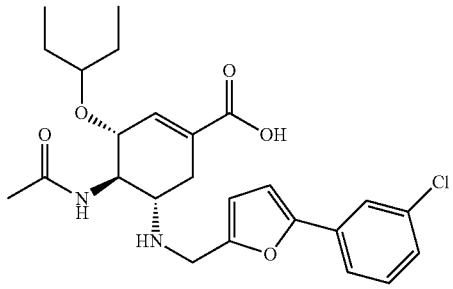

S19

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. (3-Chlorophenyl)boronic acid was used to instead of (4-Methoxyphenyl)boronic acid.

White solid. $^1$H NMR (400 MHz, DMSO) δ 7.75 (d, J=8.8 Hz, 1H), 7.70 (s, 1H), 7.62 (d, J=7.5 Hz, 1H), 7.43 (t, J=7.8 Hz, 1H), 7.30 (d, J=7.5 Hz, 1H), 6.99 (d, J=2.0 Hz, 1H), 6.34 (d, J=9.8 Hz, 2H), 3.92 (d, J=6.4 Hz, 1H), 3.77 (dd, J=47.8, 14.8 Hz, 2H), 3.63 (dd, J=17.6, 8.8 Hz, 1H), 3.31 (s, 1H), 2.70 (t, J=11.6 Hz, 2H), 1.99-1.89 (m, 1H), 1.85 (s, 3H), 1.33-1.45 (m, 4H), 0.87-0.72 (m, 6H). $^{13}$C NMR (101 MHz, DMSO) δ 169.97, 155.87, 150.73, 135.92, 134.17, 132.94, 131.22, 127.16, 123.07, 122.09, 109.36, 108.43, 80.86, 76.62, 55.33, 55.32, 43.19, 32.25, 26.25, 25.67, 23.47, 9.95, 9.46. HRMS (ESI, m/z) calcd for $C_{25}H_{30}ClN_2O_5$, 473.1849 [M–H$^-$]; found, 473.1861.

Example 20

(3R,4R,5S)-4-Acetamido-3-(pentan-3-yloxy)-5-(((5-(thiophen-3-yl)furan-2-yl)methyl)amino)cyclohex-1-ene-1-carboxylic acid (20)

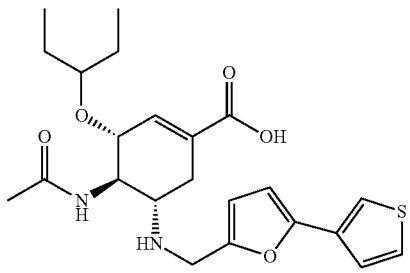

S20

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. Thiophen-3-ylboronic acid was used to instead of (4-Methoxyphenyl)boronic acid.

White solid. $^1$H NMR (400 MHz, DMSO) δ 7.80 (d, J=9.0 Hz, 1H), 7.62 (s, 2H), 7.40 (dd, J=4.0, 1.9 Hz, 1H), 6.64 (d, J=2.9 Hz, 1H), 6.61 (s, 1H), 6.29 (d, J=2.8 Hz, 1H), 4.01 (d, J=7.7 Hz, 1H), 3.76 (dd, J=32.9, 11.8 Hz, 2H), 3.70-3.63 (m, 1H), 3.36-3.33 (m, 1H), 2.74 (ddd, J=26.1, 15.8, 4.7 Hz, 2H), 2.02 (dd, J=16.8, 9.4 Hz, 1H), 1.85 (s, 3H), 1.33-1.50 (m, 4H), 0.87-0.75 (m, 6H). $^{13}$C NMR (101 MHz, DMSO) δ 170.10, 168.10, 154.07, 149.84, 137.80, 132.75, 129.80, 127.67, 125.08, 118.98, 108.83, 106.41, 81.28, 75.76, 54.70, 43.13, 30.92, 26.10, 25.61, 23.47, 9.92, 9.39. HRMS (ESI, m/z) calcd for C23H29N2O5S, 445.1803 [M–H$^-$]; found, 445.1815.

Example 21

(3R,4R,5S)-4-acetamido-5-(((5-(5-chloro-2-methylphenyl)furan-2-yl)methyl)amino)-3-(pentan-3-yloxy)cyclohex-1-ene-1-carboxylic acid (S21)

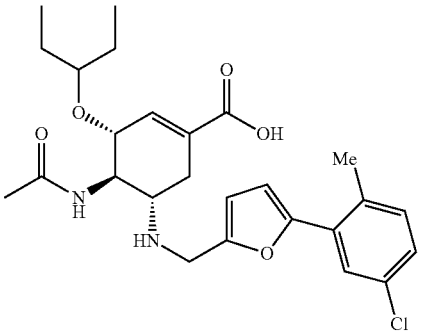

S21

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. (5-Chloro-2-methylphenyl)boronic acid was used to instead of (4-Methoxyphenyl)boronic acid.

White solid. $^1$H NMR (400 MHz, DMSO) δ 8.02 (s, 1H), 7.76 (s, 1H), 7.39-7.26 (m, 2H), 6.83 (d, J=2.6 Hz, 1H), 6.65 (s, 2H), 4.16 (s, 3H), 3.87 (s, 1H), 3.38 (d, J=5.5 Hz, 1H), 2.87 (d, J=16.2 Hz, 1H), 2.50 (s, 3H), 2.44 (s, 3H), 1.90 (s, 3H), 1.50-1.35 (m, 4H), 0.84 (t, J=7.3 Hz, 3H), 0.79 (t, J=7.4 Hz, 3H). $^{13}$C NMR (101 MHz, DMSO) δ 174.9, 170.8, 167.5, 151.6, 138.0, 133.6, 133.2, 131.4, 131.2, 128.6, 127.6, 126.1, 111.6, 81.5, 75.1, 54.4, 52.4, 29.5, 26.0, 25.5, 23.7, 21.5, 9.9, 9.3. HRMS (ESI, m/z) calcd for $C_{26}H_{32}ClN_2O_5$, 487.2005 [M–H$^-$]; found, 487.1988.

Example 22

(3R,4R,5S)-4-acetamido-5-(((5-(3,5-dimethylisoxazol-4-yl)furan-2-yl)methyl)amino)-3-(pentan-3-yloxy)cyclohex-1-ene-1-carboxylic acid (S22)

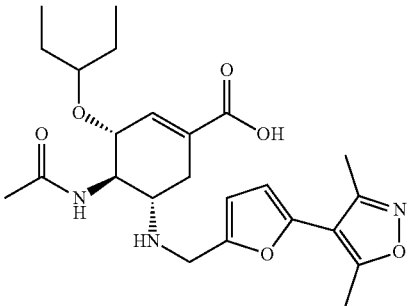

S22

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. (3,5-dimethylisoxazol-4-yl)boronic acid was used to instead of (4-Methoxyphenyl)boronic acid.

White solid. $^1$H NMR (400 MHz, DMSO) δ 7.86 (d, J=8.7 Hz, 1H), 6.62 (s, 1H), 6.55 (d, J=3.0 Hz, 1H), 6.45 (s, 1H), 4.04 (d, J=7.2 Hz, 1H), 3.90 (d, J=11.4 Hz, 2H), 3.72 (dd, J=18.1, 9.0 Hz, 1H), 3.34 (d, J=5.5 Hz, 1H), 2.88 (s, 1H), 2.82-2.71 (m, 1H), 2.50 (s, 3H), 2.34 (s, 3H), 2.21-2.04 (m, 1H), 1.85 (s, 3H), 1.47-1.34 (m, 4H), 0.83 (t, J=7.4 Hz, 3H), 0.79 (t, J=7.4 Hz, 3H). $^{13}$C NMR (101 MHz, DMSO) δ 170.3, 167.9, 165.5, 157.6, 144.3, 138.0, 129.2, 109.8, 108.3, 108.2, 81.3, 75.6, 54.4, 54.0, 42.0, 31.2, 26.1, 25.6, 23.5, 12.5, 11.6, 9.9, 9.8, 9.4. HRMS (ESI, m/z) calcd for $C_{24}H_{32}N_3O_6$, 458.2297 [M−H$^-$]; found, 458.2286.

Example 23

(3R,4R,5S)-4-acetamido-5-(((5-(dibenzo[b,d]furan-4-yl)furan-2-yl)methyl)amino)-3-(pentan-3-yloxy)cyclohex-1-ene-1-carboxylic acid (23)

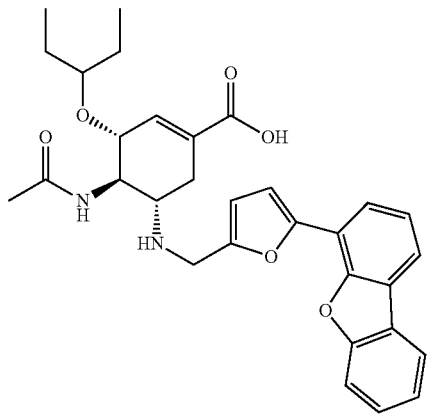

S23

The same experimental procedure detailed in the preparation of ((3R,4R,5S)-4-Acetamido-5-(((5-(4-methoxyphenyl)furan-2-yl)methyl)amino)-3-(pentan-3-yloxy)cyclohex-1-ene-1-carboxylic acid (S14) (Example 14) was used. Dibenzo[b,d]furan-4-ylboronic acid was used to instead of (4-Methoxyphenyl)boronic acid.

White solid. $^1$H NMR (400 MHz, DMSO) δ 8.20 (d, J=7.6 Hz, 1H), 8.09 (d, J=7.5 Hz, 1H), 7.97-7.76 (m, 3H), 7.58 (t, J=7.6 Hz, 1H), 7.47 (dt, J=12.5, 7.6 Hz, 2H), 7.27 (d, J=2.8 Hz, 1H), 6.64 (s, 1H), 6.61 (s, 1H), 4.15-3.70 (m, 4H), 3.30-3.40 (m, 1H), 2.97 (s, 1H), 2.82 (d, J=15.4 Hz, 1H), 2.31-2.10 (m, 1H), 1.89 (s, 3H), 1.41 (dt, J=18.7, 6.8 Hz, 4H), 0.84 (t, J=7.6 Hz, 3H), 0.79 (t, J=7.5 Hz, 3H). $^{13}$C NMR (101 MHz, DMSO) δ 170.3, 167.9, 156.0, 151.0, 147.9, 138.0, 129.4, 128.4, 124.8, 123.9, 123.7, 122.4, 121.8, 120.3, 115.8, 112.4, 111.4, 81.4, 75.6, 54.7, 54.2, 42.5, 30.2, 26.1, 25.6, 23.6, 9.9, 9.4. HRMS (ESI, m/z) calcd for $C_{31}H_{33}N_2O_6$, 529.2344 [M−H$^-$]; found, 529.2328.

Example 24

(3R,4R,5S)-4-acetamido-3-(pentan-3-yloxy)-5-(((3-phenylisoxazol-5-yl)methyl)amino)cyclohex-1-ene-1-carboxylic acid (S24)

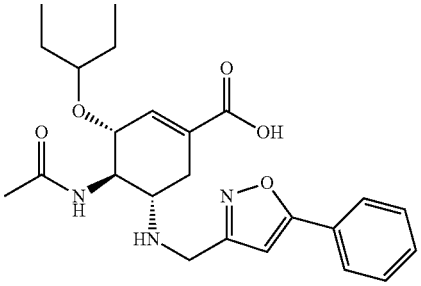

S24

Figure 3:
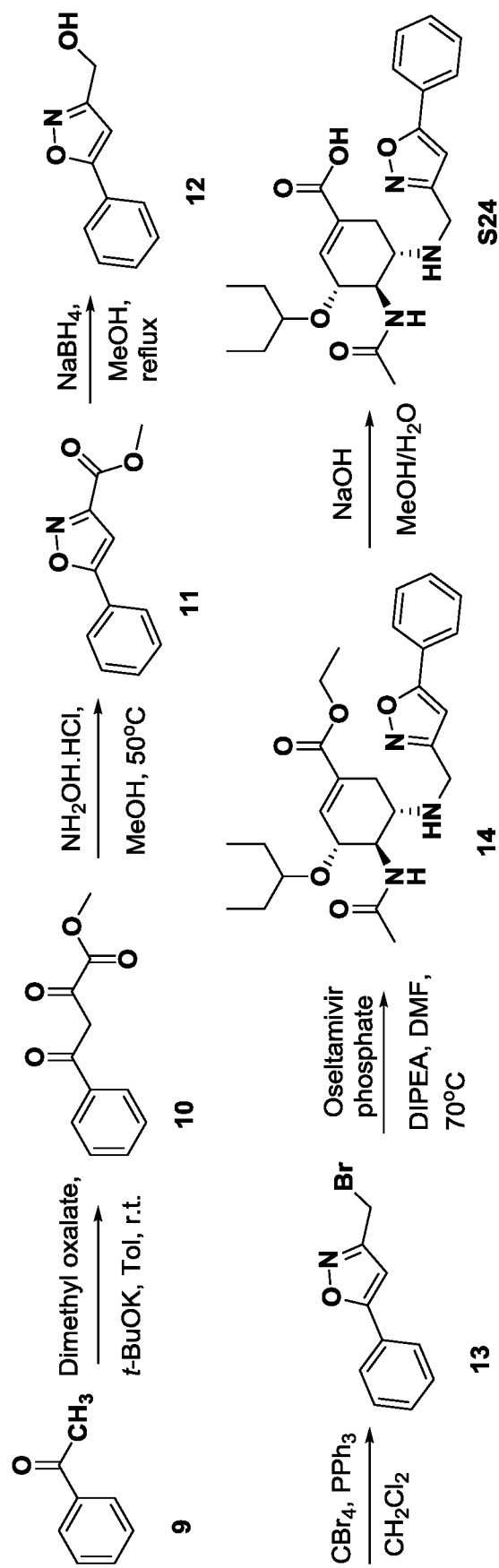
FIG. 3 depicts a schematic illustration of the preparation of the compound S3.

Preparation of S24 is illustrated in FIG. 3.

Synthesis of Intermediate 11

To a stirred solution of dimethyl oxalate (1.1 eq.) and Acetophenone (1 eq.) in toluene was added a solution of potassium tert-butoxide (1.2 eq.) in THF. The resulting solution was stirred at room temperature overnight. The reaction was quenched with 1 N HCl and extracted with ethyl acetate. The combined organic layers were dried over $Na_2SO_4$, filtered and concentrated under reduced pressure. The crude product (10) was dissolved in methanol and hydroxylamine hydrochloride was added. The solution was heated to 50° C. for 6 hrs. the solvents was removed under reduced pressure and the resulting isoxazole ester was purified by flash column chromatography to provide the target compounds.

Synthesis of Intermediate 12

Ester (1 equiv) was dissolved in methanol and cooled down to 0° C. NaBH$_4$ (4 eq.) was added in small portions to the solution over 10 min. The mixture was warmed slowly to 50° C. and stirred for five hours. NH$_4$Cl aqueous solution was added and the organic solvent was removed under reduced pressure. The resulting aqueous layer was extracted with ethyl acetate (3×), and the organic layers were combined and dried over $Na_2SO_4$, and the solvents was removed under reduced pressure. This hydroxyl intermediate was used for the next step without further purification.

Synthesis of Intermediate 13

Hydroxyl intermediate (1 equiv) was dissolved in DCM, and the resulting solution was cooled down to 0° C. CBr$_4$ (1.5 equiv) and PPh$_3$ (1.5 equiv) were added sequentially. The solution was stirred at 0° C. for 30 min and gradually warmed up to room temperature. The solvent was removed to provide the intermediates (13).

Synthesis of Intermediate 14

To a round-bottom flask were added Oseltamivir phosphate (1 equiv), compound (13) (1.2 equiv) and DMF. DIPEA (3 eq.) was added at r.t. and heated to 70° C. After 12 h, water was added to the reaction mixture followed by extracting with EA. The combined organic phase was washed with NaCl solution, dried by $Na_2SO_4$ and evaporated to provide the titled compounds.

Synthesis of S24

Compound (14) (1 equiv) was dissolved in methanol and water (v:v=5:1), NaOH (5 equiv) was added. The reaction mixture was heated to 50° C. overnight. Methanol was removed in vacuum and a small amount of water was added to the reaction mixture. The aqueous phase was washed by $CH_2Cl_2$ twice, then acidified to precipitate the target compounds.

White solid. $^1$H NMR (400 MHz, DMSO) δ 7.85 (d, J=7.4 Hz, 2H), 7.79 (d, J=9.0 Hz, 1H), 7.59-7.45 (m, 3H), 6.95 (s, 1H), 6.61 (s, 1H), 4.01 (d, J=7.9 Hz, 1H), 3.84 (dd, J=30.1, 14.6 Hz, 2H), 3.68 (dd, J=18.4, 9.1 Hz, 1H), 3.34 (s, 1H), 2.71 (t, J=14.0 Hz, 2H), 2.08-1.95 (m, 1H), 1.86 (s, 3H), 1.53-1.30 (m, 4H), 0.83 (t, J=7.5 Hz, 3H), 0.79 (t, J=7.5 Hz, 3H). $^{13}$C NMR (101 MHz, DMSO) δ 170.16, 169.06, 167.97, 164.59, 138.03, 130.74, 129.72, 129.52, 127.51, 125.97, 100.49, 81.32, 75.76, 54.68, 41.44, 30.75, 26.08, 25.59, 23.55, 9.91, 9.38. HRMS (ESI, m/z) calcd for $C_{24}H_{30}N_3O_5$, 440.2191 [M−H$^−$]; found, 440.2173.

Example 25

(3R,4R,5S)-4-Acetamido-5-(((3-(4-chlorophenyl) isoxazol-5-yl)methyl)amino)-3-(pentan-3-yloxy) cyclohex-1-ene-1-carboxylic acid (S25)

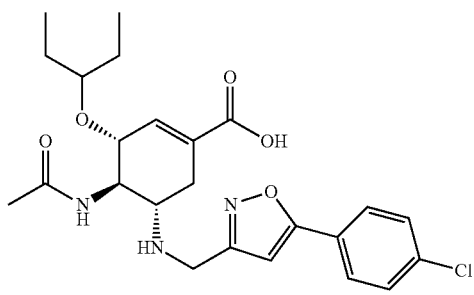

S25

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(4-Chlorophenyl)ethan-1-one was used to instead of acetophenone.

White solid. $^1$H NMR (400 MHz, DMSO) δ 7.87 (d, J=8.3 Hz, 2H), 7.80 (d, J=9.0 Hz, 1H), 7.61 (d, J=8.3 Hz, 2H), 7.00 (s, 1H), 6.60 (s, 1H), 4.00 (d, J=7.3 Hz, 1H), 3.87-3.77 (m, 2H), 3.67 (d, J=9.0 Hz, 1H), 3.33 (d, J=5.1 Hz, 1H), 2.80-2.60 (m, 2H), 2.06-1.94 (m, 1H), 1.86 (s, 3H), 1.50-1.29 (m, 4H), 0.84 (t, J=7.5 Hz, 3H), 0.79 (t, J=7.5 Hz, 3H). $^{13}$C NMR (101 MHz, DMSO) δ 170.15, 168.10, 167.89, 164.92, 137.75, 135.32, 129.83, 127.78, 126.35, 101.07, 81.30, 75.82, 54.76, 54.70, 41.47, 30.93, 26.09, 25.59, 23.54, 9.91, 9.38. HRMS (ESI, m/z) calcd for $C_{24}H_{29}ClN_3O_5$, 474.1801 [M−H$^−$]; found, 474.1785.

Example 26

(3R,4R,5S)-4-Acetamido-3-(pentan-3-yloxy)-5-(((3-(p-tolyl)isoxazol-5-yl)methyl)amino)cyclohex-1-ene-1-carboxylic acid (S26)

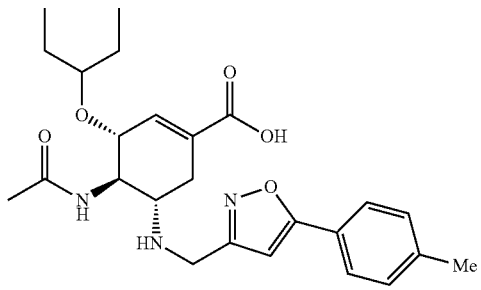

S26

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(p-tolyl)ethan-1-one was used to instead of acetophenone.

White solid. $^1$H NMR (400 MHz, DMSO) δ 7.87 (d, J=8.9 Hz, 1H), 7.73 (d, J=7.9 Hz, 2H), 7.34 (d, J=7.9 Hz, 2H), 6.88 (s, 1H), 6.58 (s, 1H), 4.01 (d, J=7.8 Hz, 1H), 3.80 (dd, J=30.6, 14.7 Hz, 2H), 3.67 (d, J=9.2 Hz, 1H), 3.35-3.32 (m, 1H), 2.76-2.60 (m, 2H), 2.36 (s, 3H), 1.99 (dd, J=16.4, 8.8 Hz, 1H), 1.86 (s, 3H), 1.47-1.29 (m, 4H), 0.83 (t, J=7.5 Hz, 3H), 0.79 (t, J=7.4 Hz, 3H). $^{13}$C NMR (101 MHz, DMSO) δ 170.16, 169.17, 168.25, 164.68, 140.54, 137.49, 130.23, 130.08, 125.92, 124.89, 99.83, 81.28, 75.88, 54.80, 54.74, 41.50, 31.00, 26.10, 25.60, 23.53, 21.46, 9.91, 9.39. HRMS (ESI, m/z) calcd for $C_{25}H_{32}N_3O_5$, 454.2347 [M−H$^−$]; found, 454.2332.

Example 27

(3R,4R,5S)-4-acetamido-5-(((3-(4-methoxyphenyl) isoxazol-5-yl)methyl)amino)-3-(pentan-3-yloxy) cyclohex-1-ene-1-carboxylic acid (S27)

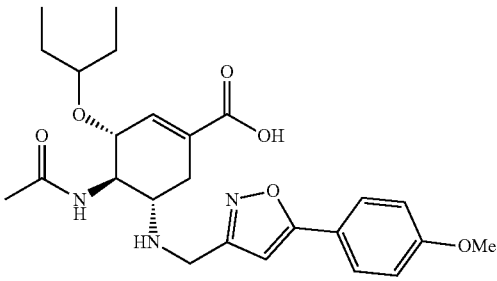

S27

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(4-methoxyphenyl)ethan-1-one was used to instead of acetophenone.

White solid. $^{1}$H NMR (400 MHz, DMSO) δ 7.78 (d, J=8.6 Hz, 3H), 7.08 (d, J=8.7 Hz, 2H), 6.79 (s, 1H), 6.59 (s, 1H), 3.99 (d, J=7.8 Hz, 1H), 3.87-3.72 (m, 5H), 3.66 (dd, J=18.8, 9.2 Hz, 1H), 3.30-3.36 (m, 1H), 2.75-2.63 (m, 2H), 1.99 (dd, J=16.5, 8.7 Hz, 1H), 1.86 (s, 3H), 1.33-1.46 (m, 4H), 0.83 (t, J=7.4 Hz, 3H), 0.79 (t, J=7.4 Hz, 3H). $^{13}$C NMR (101 MHz, DMSO) δ 170.11, 169.07, 168.16, 164.63, 161.15, 129.84, 127.66, 120.26, 115.11, 98.93, 81.29, 75.83, 55.84, 54.76, 54.72, 41.53, 30.95, 26.09, 25.59, 23.54, 9.92, 9.39. HRMS (ESI, m/z) calcd for $C_{25}H_{32}N_3O_6$, 470.2297 [M−H$^-$]; found, 470.2279.
n

Example 28

(3R,4R,5S)-4-Acetamido-3-(pentan-3-yloxy)-5-(((3-(4-(trifluoromethyl)phenyl)isoxazol-5-yl)methyl)amino)cyclohex-1-ene-1-carboxylic acid (S28)

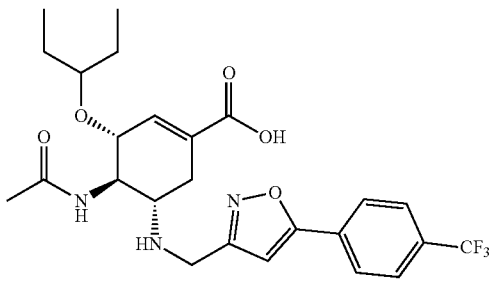

S28

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(4-(Trifluoromethyl)phenyl)ethan-1-one was used to instead of acetophenone.

White solid. $^{1}$H NMR (400 MHz, DMSO) δ 8.08 (d, J=8.0 Hz, 2H), 7.91 (d, J=8.2 Hz, 2H), 7.83 (d, J=9.1 Hz, 1H), 7.16 (s, 1H), 6.59 (s, 1H), 4.01 (d, J=7.7 Hz, 1H), 3.85 (dd, J=28.3, 14.7 Hz, 2H), 3.67 (dd, J=18.3, 9.1 Hz, 1H), 3.35-3.32 (m, 1H), 2.63-2.78 (m, 2H), 2.01 (dd, J=16.4, 9.0 Hz, 1H), 1.86 (s, 3H), 1.32-1.44 (m, 4H), 0.83 (t, J=7.5 Hz, 3H), 0.79 (t, J=7.5 Hz, 3H). $^{13}$C NMR (101 MHz, DMSO) δ 170.2, 168.2, 167.4, 165.1, 137.5, 131.1, 130.6, 130.3, 130.0, 128.5, 126.8, 126.7, 126.7, 126.6, 124.4 (q, J=272.7 Hz), 102.4, 81.3, 75.9, 54.8, 41.5, 31.0, 26.1, 25.6, 23.5, 9.9, 9.4. HRMS (ESI, m/z) calcd for $C_{25}H_{29}F_3N_3O_5$, 508.2065 [M−H$^-$]; found, 508.2049.

Example 29

(3R,4R,5S)-4-acetamido-5-(((3-(3,4-difluorophenyl)isoxazol-5-yl)methyl)amino)-3-(pentan-3-yloxy)cyclohex-1-ene-1-carboxylic acid (S29)

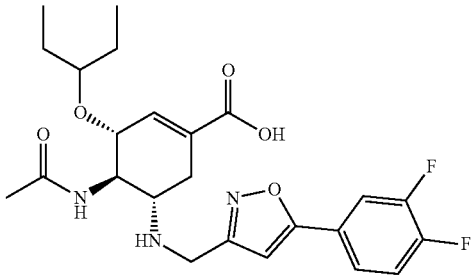

S29

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(3,4-difluorophenyl)ethan-1-one was used to instead of acetophenone.

White solid. $^{1}$H NMR (400 MHz, DMSO) δ 8.05-7.92 (m, 1H), 7.81 (d, J=8.3 Hz, 1H), 7.73 (s, 1H), 7.63 (dd, J=18.8, 8.6 Hz, 1H), 7.03 (s, 1H), 6.59 (s, 1H), 3.99 (d, J=8.0 Hz, 1H), 3.82 (q, J=14.7 Hz, 2H), 3.67 (dd, J=18.5, 9.2 Hz, 1H), 3.35-3.32 (m, 1H), 2.78-2.62 (m, 2H), 2.06-1.94 (m, 1H), 1.86 (s, 3H), 1.41 (qt, J=13.7, 6.7 Hz, 4H), 0.81 (dt, J=17.7, 7.3 Hz, 6H). HRMS (ESI, m/z) calcd for $C_{24}H_{28}F_2N_3O_5$, 476.2003 [M−H$^-$]; found, 476.1994.

Example 30

(3R,4R,5S)-4-acetamido-3-(pentan-3-yloxy)-5-(((3-(thiophen-2-yl)isoxazol-5-yl)methyl)amino)cyclohex-1-ene-1-carboxylic acid (S30)

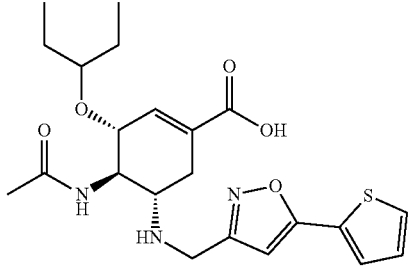

S30

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(Thiophen-2-yl)ethan-1-one was used to instead of acetophenone.

White solid. $^{1}$H NMR (400 MHz, DMSO) δ 7.99 (d, J=4.6 Hz, 1H), 7.84 (d, J=4.8 Hz, 1H), 7.71 (d, J=3.2 Hz, 1H), 7.31-7.19 (m, 1H), 6.93 (s, 1H), 6.63 (s, 1H), 4.11 (s, 3H), 3.81 (d, J=8.2 Hz, 1H), 3.39-3.35 (m, 1H), 3.10 (s, 1H), 2.80 (d, J=15.5 Hz, 1H), 2.30 (s, 1H), 1.88 (s, 3H), 1.42 (qt, J=13.7, 6.8 Hz, 4H), 0.83 (t, J=7.3 Hz, 3H), 0.79 (t, J=7.4

Hz, 3H). $^{13}$C NMR (101 MHz, DMSO) δ 170.7, 167.6, 164.8, 138.1, 130.1, 129.2, 128.7, 128.6, 128.4, 100.4, 81.5, 75.2, 54.7, 53.0, 28.5, 26.0, 25.5, 23.8, 9.9, 9.4. HRMS (ESI, m/z) calcd for $C_{22}H_{28}N_3O_5S$, 446.1755 [M–H$^-$]; found, 446.1743.

Example 31

(3R,4R,5S)-4-Acetamido-5-(((3-(5-chloro-2-methylphenyl)isoxazol-5-yl)methy)amino)-3-(pentan-3-yloxy)cyclohex-1-ene-1-carboxylic acid (S31)

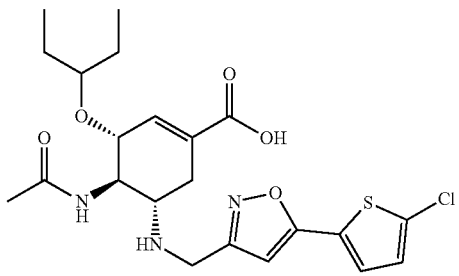

S31

The same experimental procedure detailed in the preparation of (3R,4R,5S)-4-acetamido-3-(pentan-3-yloxy)-5-(((3-phenylisoxazol-5-yl)methyl)amino)cyclohex-1-ene-1-carboxylic acid (S24) (Example 24) was used. 1-(5-Chlorothiophen-2-yl)ethan-1-one was used to instead of acetophenone.

White solid. $^1$H NMR (400 MHz, DMSO) δ 7.76 (d, J=9.1 Hz, 1H), 7.58 (d, J=4.0 Hz, 1H), 7.30 (d, J=4.0 Hz, 1H), 6.83 (s, 1H), 6.56 (s, 1H), 3.98 (d, J=7.9 Hz, 1H), 3.79 (dd, J=28.5, 14.7 Hz, 2H), 3.65 (dd, J=18.6, 9.2 Hz, 1H), 3.37-3.29 (m, 1H), 2.72-2.62 (m, 2H), 2.04-1.93 (m, 1H), 1.85 (s, 3H), 1.51-1.31 (m, 4H), 0.83 (t, J=7.4 Hz, 3H), 0.79 (t, J=7.4 Hz, 3H). $^{13}$C NMR (101 MHz, DMSO) δ 170.1, 165.0, 163.0 137.1, 131.6, 129.0, 127.9, 127.9, 100.4, 81.2, 75.9, 54.8, 41.4, 31.1, 26.1, 25.6, 23.5, 9.9, 9.4. HRMS (ESI, m/z) calcd for $C_{22}H_{27}ClN_3O_5S$, 480.1365 [M–H$^-$]; found, 480.1355.

Example 32

Inhibition Rate of Compounds S1-S22 (1 nM) Against NA from A/H3N2

Newly synthesized compounds S1-S22 were preliminarily screened for NA-inhibitory activity using MUNANA (4-(methylumbelliferyl)-N-acetylneuraminic acid) as the substrate. For NA inhibition screening, the endemic human strains seasonal A/H3N2 was chosen and oseltamivir carboxylate (OSC) was employed as the reference. Table 1 showed the tested inhibition potencies of the designed compounds. It was obviously that OSC showed the greatest inhibitory activity toward A/H3N2 NA.

The NA inhibition assay was performed using the commercially available NA-Fluor™ Influenza Neuraminidase Assay Kit. The substrate, MUNANA (4-(methylumbelliferyl)-N-acetylneuraminic acid) was cleaved by NA to yield a quantifiable fluorescent product. The tested compounds were dissolved in DMSO and diluted by the 1× assay buffer (66.6 mM 2-(N-morpholino)ethanesulfonic acid (MES) buffer, 8 mM $CaCl_2$, pH 6.5) to 4× the desired concentrations. In a 96-well plate, 25 µL. of the 4× compounds solution, 25 µL of the diluted virus sample were added and incubated for 20 to 30 min at 37° C. 50 µL of diluted 200 µM NA-Fluro™ Substrate working solution was added to each well and incubated for 60 min at 37° C. Finally, the reaction was terminated by adding 100 µL of NA-Fluor™ Stop Solution (0.2 M $Na_2CO_3$) and the fluorescence was read at an excitation wavelength of 350 nm and an emission of 460 nm.

TABLE 1

| Inhibition rate of designed compounds (1 nM) against NA from A/H3N2. | | | | | | |
|---|---|---|---|---|---|---|
| Derivatives | Compd. | R | % Inhibition (1 nM) | Compd. | R | % Inhibition (1 nM) |
| [structure] | OSC | \ | 66.8 ± 0.4 | S7 | [furan] | 28.1 ± 1.7 |
| | S1 | [thiophene] | 0.0 ± 2.2 | S8 | [phenyl] | 0.0 ± 2.0 |
| | S2 | [4-CF3-phenyl] | 8.0 ± 1.7 | S9 | [naphthyl] | 1.5 ± 1.2 |

TABLE 1-continued

Inhibition rate of designed compounds (1 nM) against NA from A/H3N2.

| Derivatives | Compd. | R | % Inhibition (1 nM) | Compd. | R | % Inhibition (1 nM) |
|---|---|---|---|---|---|---|
| (core structure shown at left) | S3 | 4-F-phenyl | 0.0 ± 3.5 | S10 | 2-Me-phenyl | 0.5 ± 2.0 |
| | S4 | pyridin-2-yl | 17.1 ± 2.0 | S11 | 3,4,5-trimethoxyphenyl | 3.5 ± 3.1 |
| | S5 | 4-Br-phenyl | 1.7 ± 2.1 | S12 | 4-Cl-phenyl | 4.01 ± 5.9 |
| | S6 | 3-NO$_2$-phenyl | 18.4 ± 3.6 | S13 | 2,3-diF-phenyl | 0.0 ± 2.6 |
| | S14 | 4-MeO-phenyl | 14.7 ± 4.4 | S19 | 3-Cl-phenyl | 5.5 ± 2.4 |
| | S15 | 4-F-phenyl | 3.2 ± 3.7 | S20 | thiophen-3-yl | 12.5 ± 2.3 |
| | S16 | 2-Me-phenyl | 8.4 ± 1.8 | S21 | 2-Me-5-Cl-phenyl | 4.8 ± 1.1 |
| | S17 | 3,5-diF-phenyl | 3.7 ± 3.8 | S22 | 3,5-dimethylisoxazol-4-yl | 30.2 ± 1.5 |
| | S18 | 3,4-diMeO-phenyl | 12.9 ± 1.2 | S23 | dibenzofuran-4-yl | 10.9 ± 0.7 |

TABLE 1-continued

Inhibition rate of designed compounds (1 nM) against NA from A/H3N2.

| Derivatives | Compd. | R | % Inhibition (1 nM) | Compd. | R | % Inhibition (1 nM) |
|---|---|---|---|---|---|---|
| (oseltamivir-isoxazole scaffold) | S24 | phenyl | 1.6 ± 0.4 | S28 | 4-CF₃-phenyl | 8.1 ± 2.3 |
| | S25 | 4-Cl-phenyl | 5.2 ± 0.9 | S29 | 3,4-difluorophenyl | 0.4 ± 1.6 |
| | S26 | 4-Me-phenyl | 3.9 ± 3.6 | S30 | thiophen-2-yl | 3.0 ± 0.7 |
| | S27 | 4-MeO-phenyl | 5.4 ± 3.8 | S31 | 5-Cl-thiophen-2-yl | 0.3 ± 2.0 |

TABLE 2

| Compound | S7 | S22 |
|---|---|---|
| IC$_{50}$ (nM) | 1.92 ± 0.24 | 1.63 ± 0.16 |

Example 33

Inhibition Rate of Designed Compounds (1 nM) Against 12v3261, 12v28393, and 12v3280

Materials and Method
Virus Strains:

Three influenza B viruses (IVB) 12v3261, 12v28393, and 12v3280 together with two oseltamivir-resistant influenza A viruses (IVA) H1N1 pandemic viruses, 09v71923 and 11v17178 were isolated from nasopharyngeal aspirates collected from patients admitted to Prince of Wales Hospital. The viruses were propagated in Madin-Darby Canine Kidney (MDCK) cells for no more than 6 passages. Seasonal H1N1 influenza A virus (A/Oklahoma/447/2008), a gift of Prof Gillian Air, University of Oklahoma Health Sciences Center, was used as the comparator virus in this study.

Cell Line and Virus Propagation:

MDCK cells were cultured in minimal essential medium (MEM) supplemented with 10% fetal bovine serum (FBS) and 1% penicillin and streptomycin at 37° C. MDCK cells were seeded in a T175 flask and grew until 80% confluence before viral propagation. MDCK cells were washed with PBS to remove FBS before inoculation of the virus at a multiplicity of infection (MOI) of 0.001. After one hour of virus adsorption at 37° C., cells were washed with PBS and replenished with MEM containing 1 μg/ml TPCK-treated trypsin (Sigma T1426) without FBS. The culture supernatant was harvested on day 3 post-infection, with 50-70% of the cells showing cytopathic effect, by centrifugation at 4000 rpm, 4° C. for 10 minutes. The supernatant was harvested and stored in aliquots at −80° C. Viral titer was then determined by plaque assay.

Plaque Assay for Virus Titration, Compound Effectiveness Quantification, and Plaque Measurements MDCK cells were seeded on a 6-well plate at a density of 1.2×10⁶ per well one day prior to infection. Before the plaque assay, cells were washed with PBS. Influenza virus stocks harvested with unknown titer were diluted 10 fold serially with MEM with PS. 1 ml of the diluted virus was added to each of the 6 wells, and the plate was rocked gently every 15 min for 1 hour in a 37° C. incubator with 5% CO₂. After the virus adsorption, the inoculum was discarded and the cells were washed with PBS. 2 ml agarose overlay reconstituted from MEM containing 1 μg/ml TPCK-treated trypsin, 0.8% SeaKem® LE Agarose (Lonza 50002) was added to each well.

To examine the effectiveness of S7 and S22 in inhibiting influenza virus replication, we included 0.1 nM and 0.2 nM oseltamivir as the positive control. In previous studies, the half maximal inhibitory concentration (IC$_{50}$) of oseltamivir, S7 and S22 were 0.1 nM, 1.9 nM and 1.6 nM respectively, as determined by a neuraminidase activity assay (Ye et al., 2019). Therefore, 1.9 nM and 3.8 nM of S7; and 1.6 nM and 3.2 nM of S22 were reconstituted using 4 nM DMSO in PBS. Briefly, each well of the MDCK cells was inoculated with 60 Plaque formation units (pfu) of the virus in 1 ml inoculum at 37° C. for one hour. After the virus adsorption, cells were extensively washed with PBS for three times and then overlaid with 2 ml agarose containing the respective concentrations of antiviral compounds, or equal amount of PBS and 4 nM DMSO in PBS were used as the untreated and vehicle control, respectively. Technical duplicates were included in each experiment, and the experiment was carried out for at least three times.

Upon the solidification of the agarose, the assay plates were incubated upside-down in a 37° C. incubator with 5% $CO_2$ for 3 days. On day 3, 10% formalin was added onto the agarose for the cell fixation. The agarose was removed from the well and the MDCK cell was subsequently stained by 1% crystal violet (Ig crystal violet dissolved in 10 ml 95% ethanol and 90 ml MilliQ water) for 1 hour. The stained monolayer was then washed and air-dried.

Figure 4:
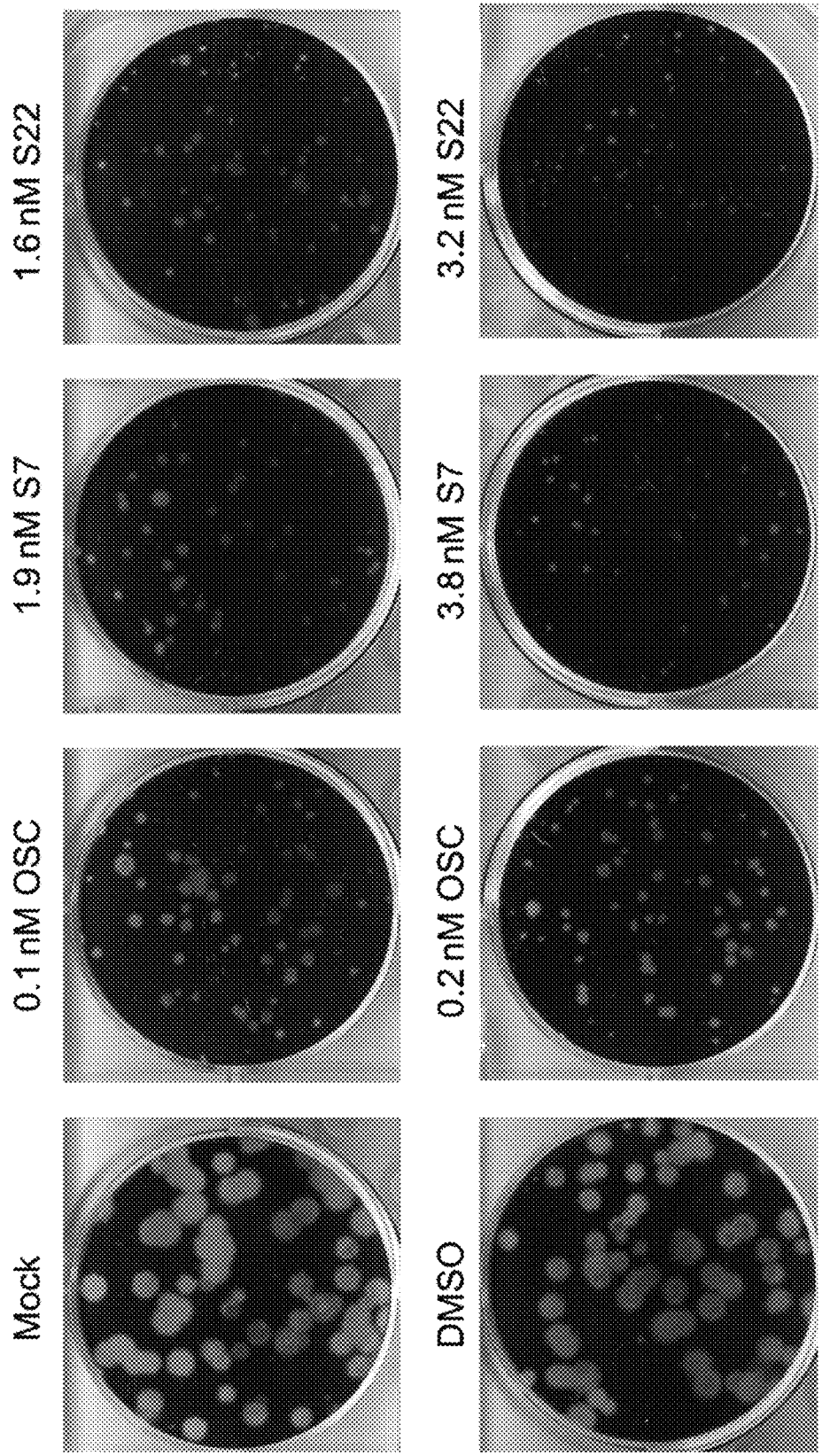
FIG. 4 depicts representative scans of plaque assay result using seasonal H1N1 virus (A/OK/447/2008) on day 3 post infection. MDCK cells were treated with the corresponding novel compounds at two concentrations for 72 hours after infected with 70 PFU virus. Upon the treatment of oseltamivir, S7 and S22, a reduction in plaque size of A/OK/447/2008 (H1N1) but not plaque count was seen.
Figure 5:
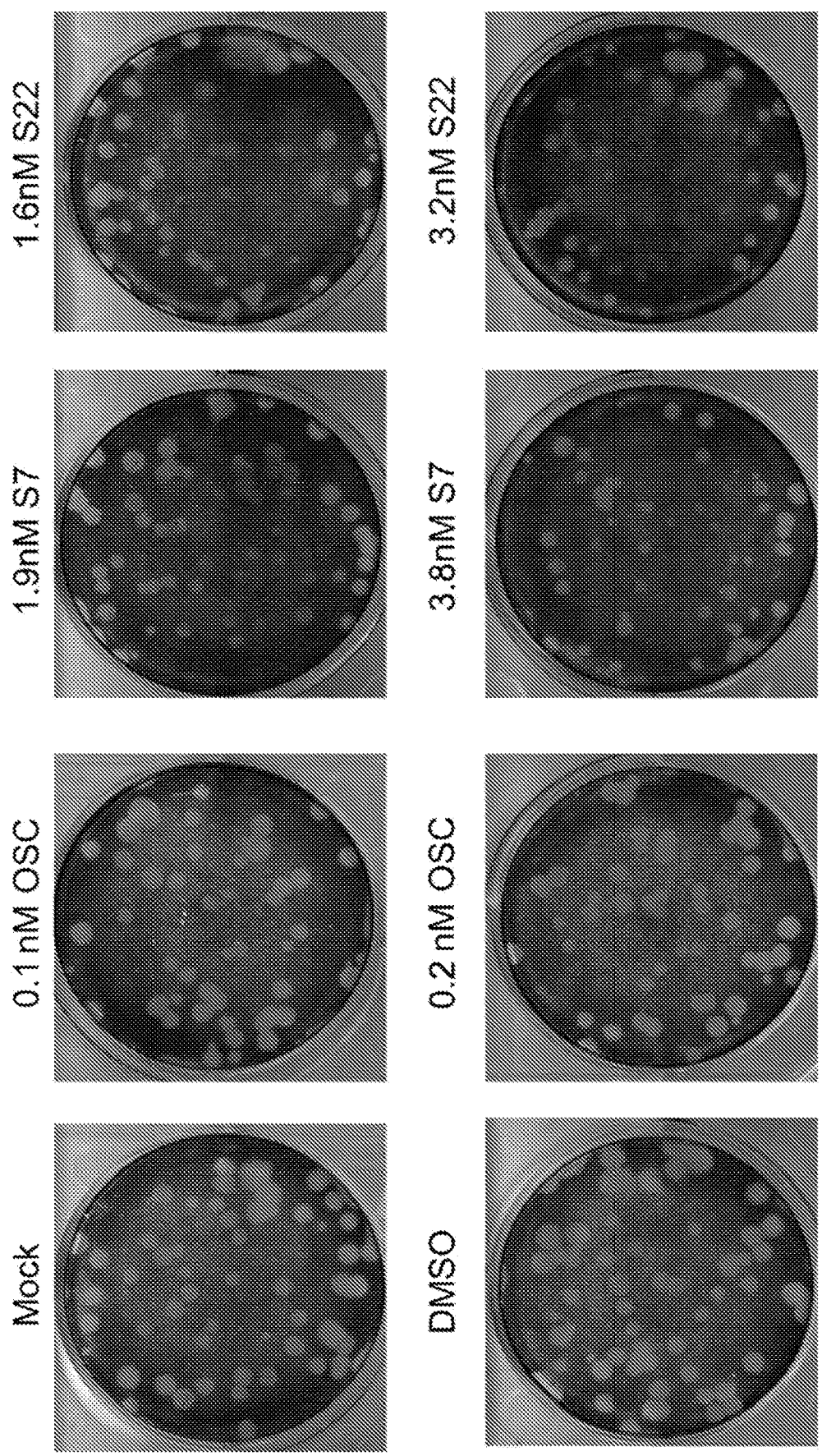
FIG. 5 depicts representative scans of plaque assay result using seasonal H1N1 virus resistant strain 09v71923 on day 3 post infection. MDCK cells were treated with the corresponding novel compounds at two concentrations for 72 hours after infected with 70 PFU virus. Upon the treatment of oseltamivir, S7 and S22, a reduction in plaque size of A/OK/447/2008 (H1N1) but not plaque count was seen.
Figure 6:
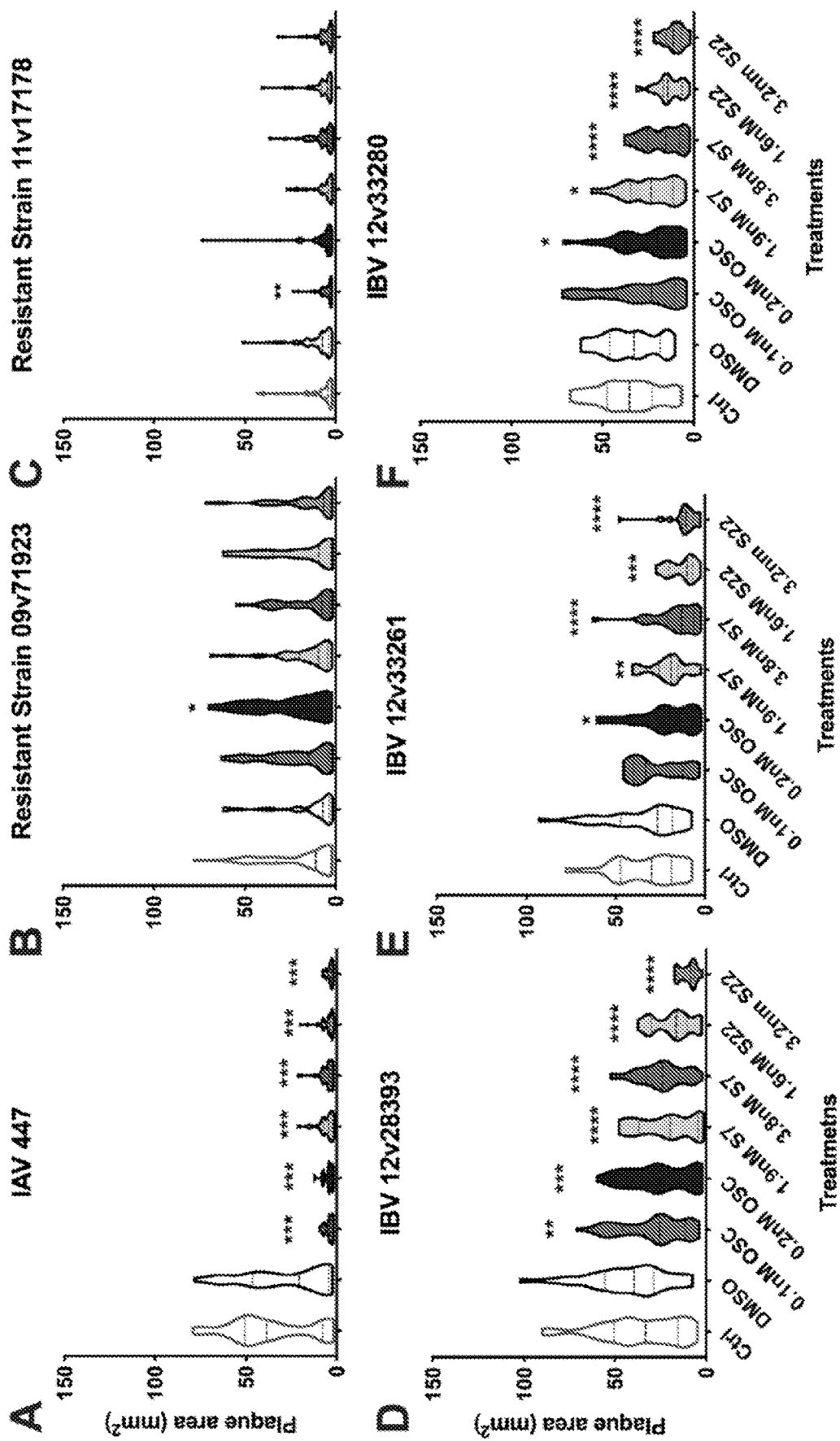
FIG. 6 depicts A) influenza A virus A/OK/447/08 (H1N1), B) oseltamivir-resistant strain 09v71923, C) oseltamivir-resistant strain 11v17178, D) influenza B virus (IBV) 12v28393, E) IBV 12v33261 and F) IBV 12v33280. Plaque size differences in each treatment was tested using one-way ANOVA compared to DMSO vehicle control followed by Tukey's multiple comparison tests. Dotted line in the middle shows the median and the thinner lines show interquartile range and the whiskers show 95% confidence interval. Key: * $p<0.05$, : $p<0.01$, *: $p<0.005$, ****: $p<0.001$.
Figure 7:
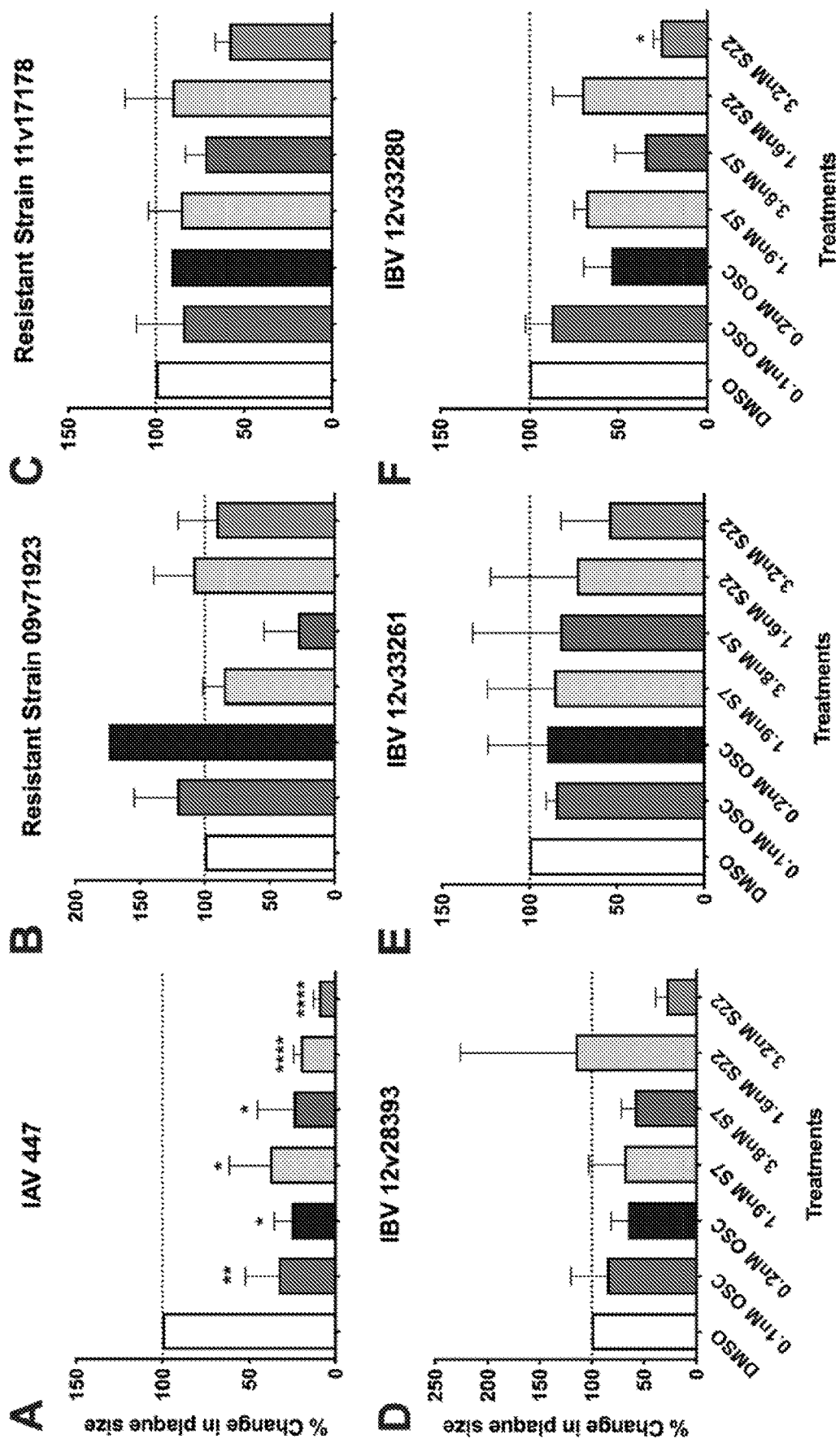
FIG. 7 depicts Bar-chart representing the percentage change of plaque count recorded in each treatments when compared to DMSO vehicle control. A) influenza A virus A/OK/447/08 (H1N1), B) oseltamivir-resistant strain 09v71923, C) oseltamivir-resistant strain 11v17178, D) influenza B virus (IBV) 12v28393, E) IBV 12v33261 and F) IBV 12v33280. Plaque size differences in each treatment was tested using one-way ANOVA compared to DMSO vehicle control followed by Tukey's multiple comparison tests. (n=3 for IVAs, and n=2 for IVBs)

For virus titration, the number of plaques in each virus dilution was used to calculate the concentration of the virus stock expressed in pfu. For the compound effectiveness quantification, the total number of plaques in each well and the area of individual plaque were analysed using OpenCFU software. Plaques with a radius of 5 pixels (0.8 mm in diameter) were excluded from further analysis. Representative scan images of the plaque assay plates are presented in FIGS. 4 and 5.

Statistical Analysis

The plaque number yielded from each treatment was expressed as the percentage of plaque number of the DMSO vehicle control of the same set of experiment. The plaque size measured was expressed in $mm^2$. (OR The individual plaque area in each treatment was expressed in the percentage of the average plaque area of the PBS control in that set of experiment.) The plaque number and plaque size changes among treatments were compared with the vehicle control using one-way ANOVA analysis, followed by Tukey's multiple comparisons test. Results were deemed significant when $p < 0.05$.

Result

At both concentrations, S7 and S22 could significantly reduce the plaque size of influenza A virus A/OK/447/08 (H1N1) (FIG. 1A) and the three strains of influenza B viruses (FIG. 1D-F). No inhibition effect of these compounds towards the two oseltamivir-resistant strains (FIGS. 1B and 1C). In addition, oseltamivir could not reduce the plaque size of resistant strain 09v71923, and even with a larger plaque size with the addition of 0.2 nM oseltamivir was observed (FIG. 1B), while a significant reduction by 0.1 nM oseltamivir was observed in the oseltamivir-resistant 11v17178.

To understand if there is a better inhibitory effect of S7 and S22 towards oseltamivir, we further compared the plaque size between those treated with 0.2 nM oseltamivir with effective reduction in plaque size to both compounds at both concentrations. Both compounds did equally well in inhibiting influenza A virus A/OK/337/08 (H1N1) while S22 always provided extra inhibitory effect than oseltamivir in inhibiting influenza B viruses, including a better inhibition effect by 3.2 nM S22 to 0.2 nM oseltamivir in in IBV 12v28393 ($p < 0.01$), IBV 12v33261 ($p < 0.05$), and IBV 12v33280 ($p < 0.01$). 1.6 nM S22 also provided extra benefit than 0.2 nM oseltamivir in reducing the plaque size of IBV 12v33280 ($p < 0.05$). S22 at 1.6 nM S22 ($p < 0.05$) and 3.2 nM S22 ($p < 0.01$) inhibited the IBV 12v33280 better than 1.9 nM S7. Though 3.8 nM S7 could provide extra benefit to inhibit 12v28393 ($p < 0.05$) than 3.2 nM S22.

Example 34

Inhibition Rate of Compounds OC-001-OC-029 (1 µM and 10 µM) Against NA from A/H3N2

Newly synthesized compounds OC-001-OC-029 were preliminarily screened for NA-inhibitory activity using MUNANA (4-(methylumbelliferyl)-N-acetylneuraminic acid) as the substrate. For NA inhibition screening, the endemic human strains seasonal A/H3N2 was chosen and oseltamivir carboxylate (OSC) was employed as the reference. Table 2 showed the tested inhibition potencies of the designed compounds. It was obviously that OSC showed the greatest inhibitory activity toward A/H3N2 NA.

The NA inhibition assay was performed using the commercially available NA-Fluor™ Influenza Neuraminidase Assay Kit. The substrate, MUNANA (4-(methylumbelliferyl)-N-acetylneuraminic acid) was cleaved by NA to yield a quantifiable fluorescent product. The tested compounds were dissolved in DMSO and diluted by the 1× assay buffer (66.6 mM 2-(N-morpholino)ethanesulfonic acid (MES) buffer, 8 mM $CaCl_2$, pH 6.5) to 4× the desired concentrations. In a 96-well plate, 25 µL of the 4× compounds solution, 25 µL of the diluted virus sample were added and incubated for 20 to 30 min at 37° C. 50 µL of diluted 200 µM NA-Fluor™ Substrate working solution was added to each well and incubated for 60 min at 37° C. Finally, the reaction was terminated by adding 100 µL of NA-Fluor™ Stop Solution (0.2 M $Na_2CO_3$) and the fluorescence was read at an excitation wavelength of 350 nm and an emission of 460 nm.

TABLE 3

Inhibition rate of designed compounds (1 µM and 10 µM) against NA from A/H3N2.

| | OC-001 | OC-002 | OC-003 | OC-004 | OC-005 | OC-006 | OC-007 | OC-008 | OC-009 | OC-010 |
|---|---|---|---|---|---|---|---|---|---|---|
| 10 µM | 32.02% | 23.37% | 23.88% | 26.79% | 18.88% | 21.72% | 12.26% | 42.81% | 46.76% | 52.31% |
| 1 µM | 7.71% | 6.12% | 5.74% | −0.21% | −1.46% | −2.25% | −5.33% | 5.84% | 3.44% | 8.96% |
| | OC-011 | OC-012 | OC-013 | OC-014 | OC-015 | OC-016 | OC-017 | OC-018 | OC-019 | OC-020 |
| 10 µM | 50.43% | 56.45% | 30.41% | 40.02% | 31.50% | 38.37% | 42.02% | 39.81% | 48.50% | 44.47% |
| 1 µM | 14.65% | 33.62% | 19.92% | 21.57% | 16.52% | 12.74% | 14.83% | 11.12% | 11.62% | 8.26% |
| | OC-021 | OC-022 | OC-023 | OC-024 | OC-025 | OC-026 | OC-027 | OC-028 | OC-029 | |

TABLE 3-continued

Inhibition rate of designed compounds (1 μM and 10 μM) against NA from A/H3N2.

| 10 μM | 30.57% | 34.15% | 34.75% | 42.68% | 37.17% | 25.67% | 31.53% | 60.91% | 72.80% |
|---|---|---|---|---|---|---|---|---|---|
| 1 μM | 7.13% | 6.31% | 6.24% | 5.84% | 2.19% | −0.26% | 0.70% | 8.06% | 23.28% |

To examine the effectiveness of OC-010, OC-012, OC-028, and OC-029 in inhibiting influenza virus replication, experiments were conducted to determine the half maximal inhibitory concentration ($IC_{50}$) of OC-010, OC-012, OC-028, and OC-029, which were observed to be 43.9 μM, 11.6 μM, 22.7 μM, and 16.9 μM respectively, as determined by a neuraminidase activity assay (Ye et al., 2019) and shown in Table 3.

TABLE 4

| Compound | OC-010 | OC-012 | OC-028 | OC-029 |
|---|---|---|---|---|
| $IC_{50}$ (μM) | 43.9 ± 1.77 | 11.6 ± 0.52 | 22.7 ± 1.47 | 16.9 ± 1.07 |

What is claimed:

1. A compound of Formula I:

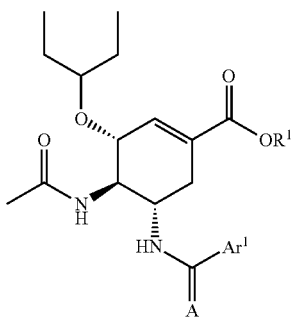

I or a pharmaceutically acceptable salt thereof, wherein A is O; or —(C=A)- is —(CH$_2$)—;

$Ar^1$ is selected from the group consisting of:

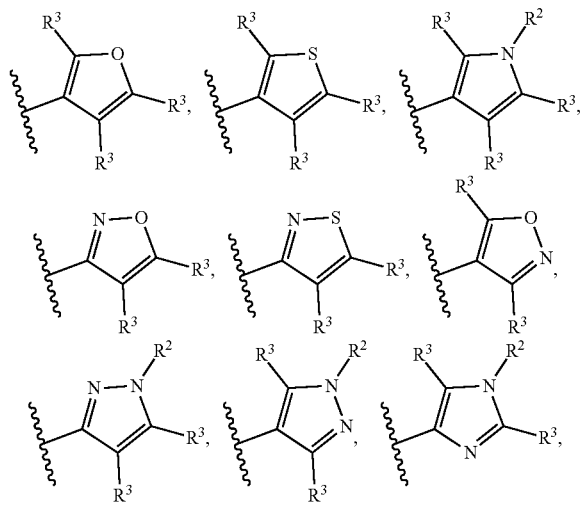

wherein $R^2$ is hydrogen, alkyl, alkenyl, alkynyl, cycloalkyl, heterocycloalkyl, aryl, aralkyl, heteroaryl, —(C=O)R, —(C=O)OR, —(C=O)NR$_2$, —(C=NR)NR$_2$, —(S=O)R, —S(O)$_2$R, —S(O)$_2$OR, —S(O)$_2$NR$_2$, —(P=O)(OR)$_2$, or —(CR$_2$)$_m$Y; and $R^3$ for each instance is independently hydrogen, alkyl, alkenyl, alkynyl, cycloalkyl, heterocycloalkyl, aryl, aralkyl, heteroaryl, OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —NR)(C=O) NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O) NR$_2$, —(NR)S(O)$_2$NR$_2$, —(NR)S(O)$_2$OR, —(P=O) (OR)$_2$, halide, nitrile, nitro, or —(CR$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —(NR)(C=O)

NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P=O)(OR)$_2$; and R$^1$ is hydrogen, alkyl, alkenyl, alkynyl, cycloalkyl, heterocycloalkyl, aryl, or heteroaryl.

2. The compound of claim 1, wherein the compound has the Formula III:

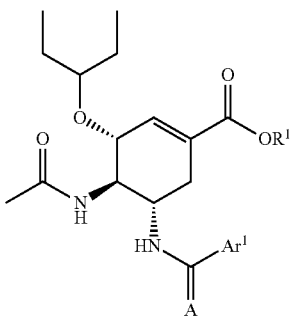

III or a pharmaceutically acceptable salt thereof, wherein A is O—; or —(C=A)- is —(CH2)-;

Ar$^1$ is selected from the group consisting of:

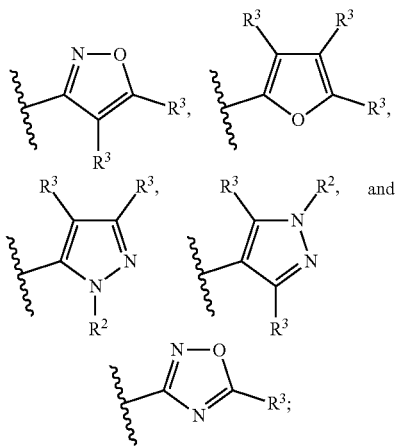

wherein R$^2$ is hydrogen, alkyl, alkenyl, alkynyl, cycloalkyl, heterocycloalkyl, aryl, aralkyl, heteroaryl, —(C=O)R, —(C=O)OR, —(C=O)NR$_2$, —(C=NR)NR$_2$, —(S=O)R, —S(O)$_2$R, —S(O)$_2$OR, —S(O)$_2$NR$_2$, —(P=O)(OR)$_2$, or —(CR$_2$)$_m$Y; and R$^3$ for each instance is independently hydrogen, alkyl, alkenyl, alkynyl, cycloalkyl, heterocycloalkyl, aryl, aralkyl, heteroaryl, OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —NR)(C=O)NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)NR$_2$, —(NR)S(O)$_2$NR$_2$, —(NR)S(O)$_2$OR, —(P=O)(OR)$_2$, halide, nitrile, nitro, or —(CR$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —(NR)(C=O)NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P=O)(OR)$_2$; and R$^1$ is hydrogen, alkyl, alkenyl, alkynyl, cycloalkyl, heterocycloalkyl, aryl, or heteroaryl.

3. The compound of claim 2, wherein Ar$^1$ is selected from the group consisting of:

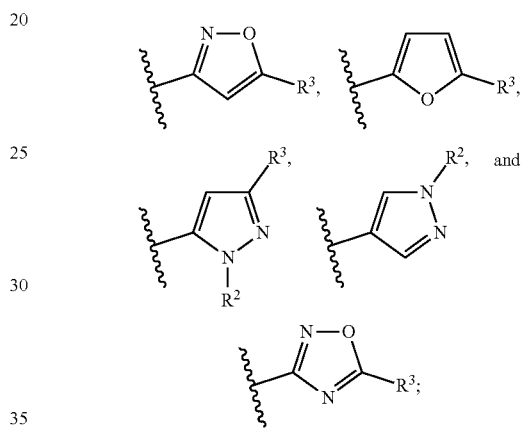

wherein R$^2$ is hydrogen, heterocycloalkyl, aryl, aralkyl, or heteroaryl; and R$^3$ is heterocycloalkyl, aryl, aralkyl, or heteroaryl.

4. The compound of claim 1, wherein the compound is selected from the group consisting of:

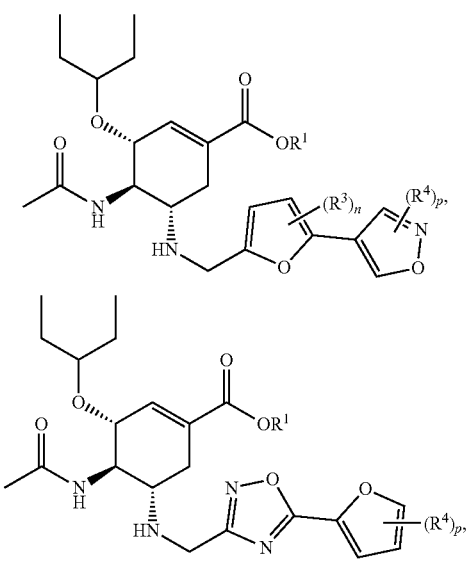

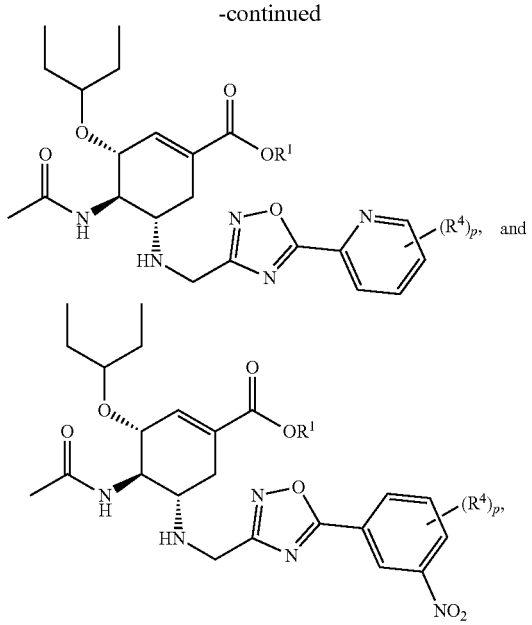

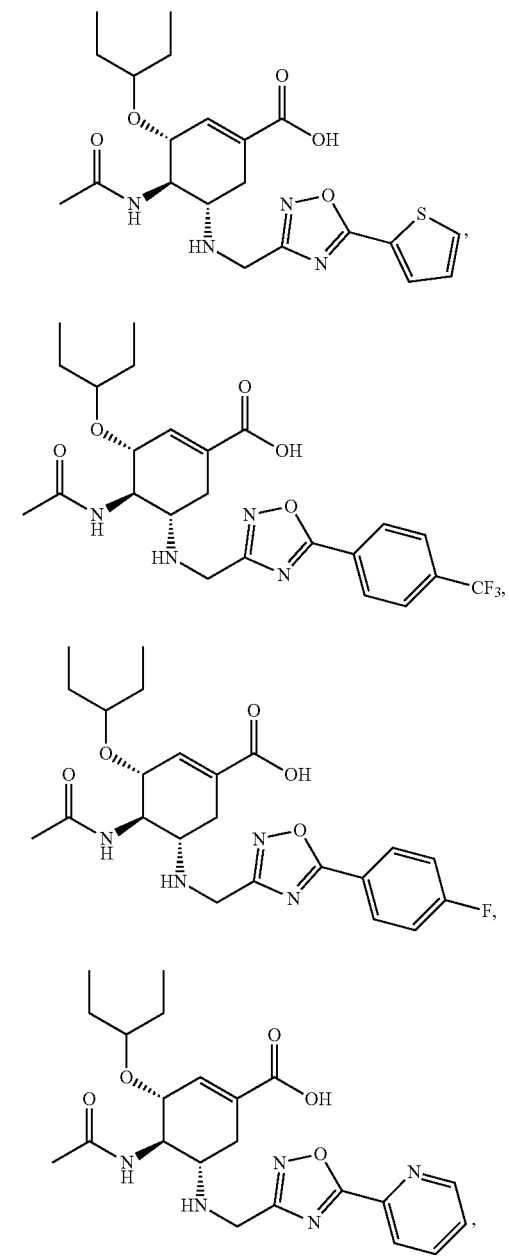

wherein n is 0, 1, or 2; p is 0, 1, or 2; and each of $R^3$ and $R^4$ for each occurrence is independently alkyl, alkenyl, alkynyl, cycloalkyl, heterocycloalkyl, aryl, aralkyl, heteroaryl, OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)(C=NR)$NR_2$, —(S=O)R, —S(O)$_2$R, —S(O)$_2$OR, —S(O)$_2NR_2$, —OS(O)$_2$R, —(NR)S(O)$_2$R, —OS(O)$_2$OR, —OS(O)$_2NR_2$, —(NR)S(O)$_2NR_2$, —(NR)S(O)$_2$OR, —(P=O)(OR)$_2$, halide, nitrile, nitro, or —(CH$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)(C=NR)$NR_2$, —(S=O)R, —S(O)$_2$R, —S(O)$_2$OR, —S(O)$_2NR_2$, —OS(O)$_2$R, —(NR)S(O)$_2$R, —OS(O)$_2$OR, —OS(O)$_2NR_2$, —(NR)S(O)$_2NR_2$, —(NR)S(O)$_2$OR, and —(P=O)(OR)$_2$.

5. The compound of claim 4, wherein n is 0; and $R^4$ for each occurrence is independently alkyl, cycloalkyl, heterocycloalkyl, aryl, aralkyl, heteroaryl, OR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)(C=NR)$NR_2$, —(S=O)R, —S(O)$_2$R, —S(O)$_2$ OR, —S(O)$_2NR_2$, —OS(O)$_2$R, —(NR)S(O)$_2$R, —OS(O)$_2$ OR, —OS(O)$_2NR_2$, —(NR)S(O)$_2NR_2$, —(NR)S(O)$_2$OR, —(P=O)(OR)$_2$, halide, nitrile, nitro, or —(CH$_2$)$_m$Y, wherein m is 1-6; and R for each occurrence is independently hydrogen, alkyl, cycloalkyl, aryl, or heteroaryl.

6. The compound of claim 1, wherein the compound is selected from the group consisting of:

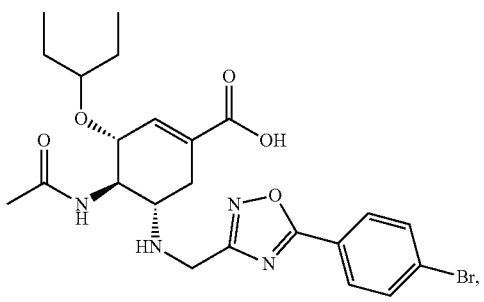

S6
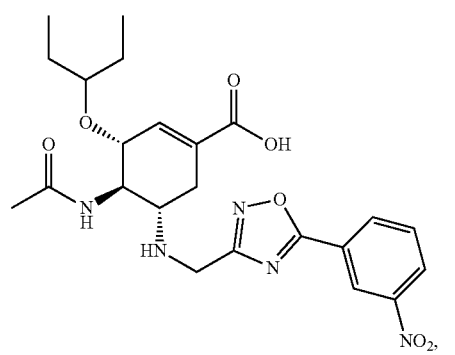
S7
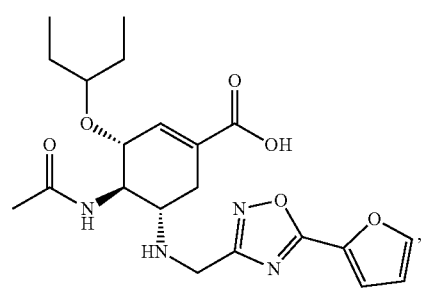
S8
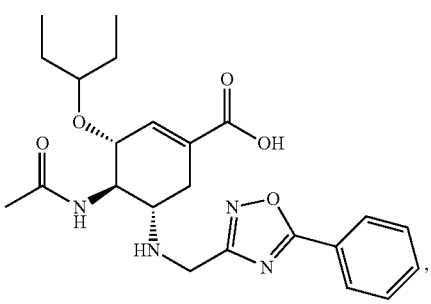
S9
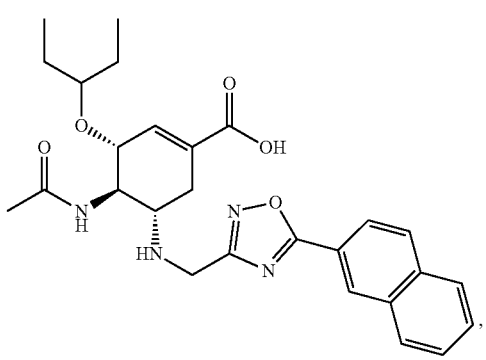
S10
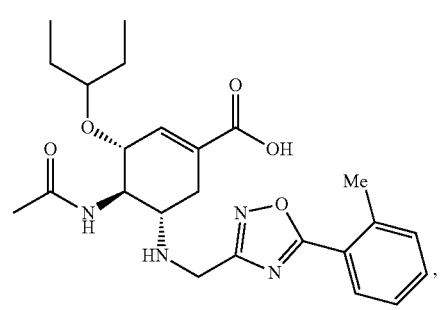
S11
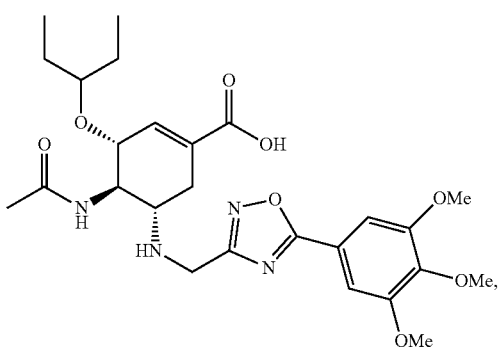
S12
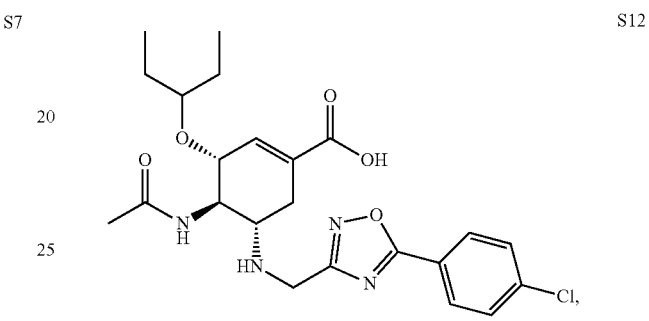
S13
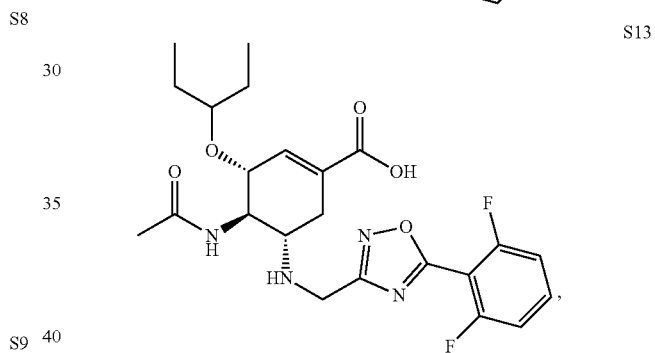
S14
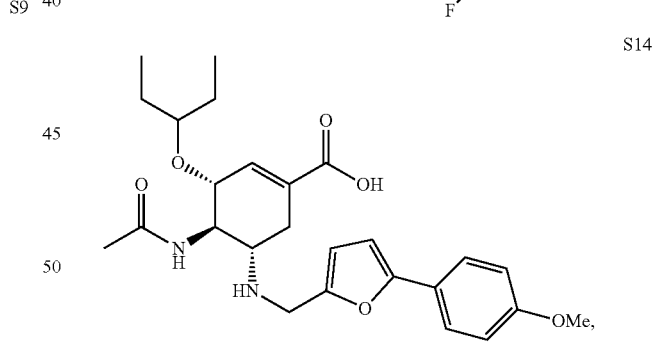
S15
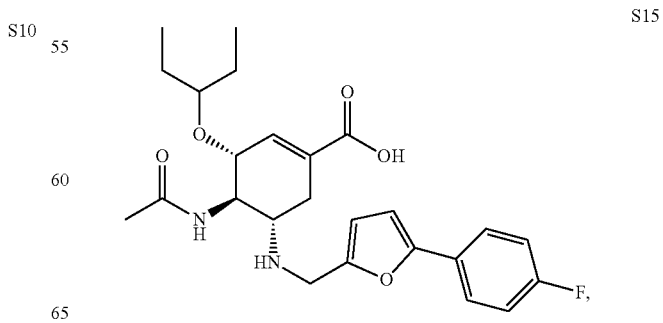

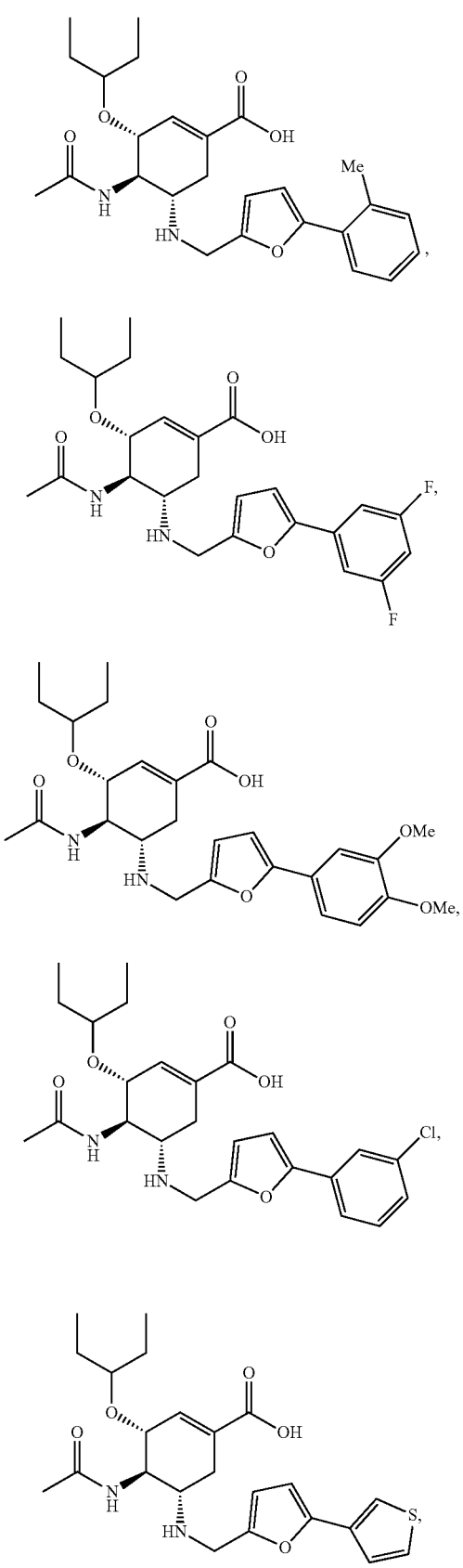
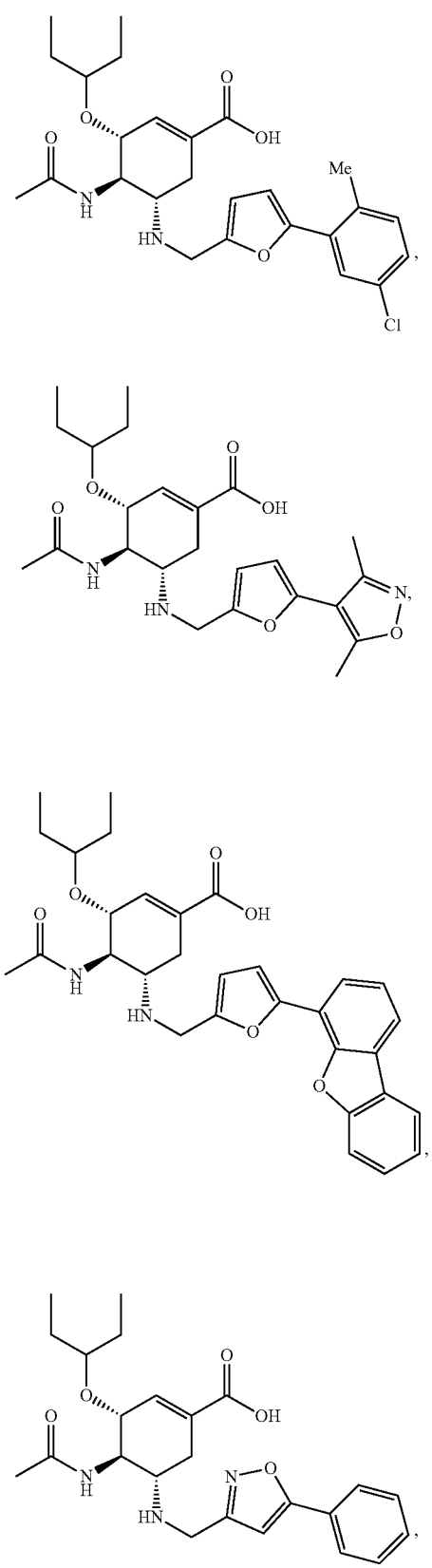

-continued
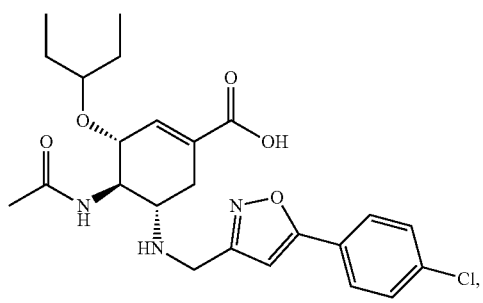
S25
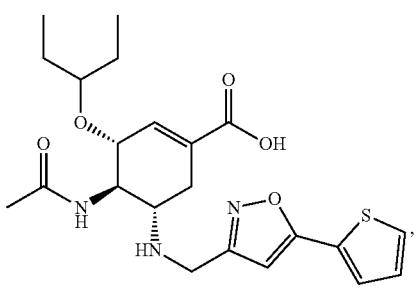
S30
S26
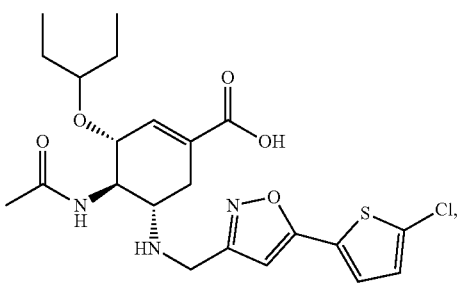
S31
S27
S28
OC-001
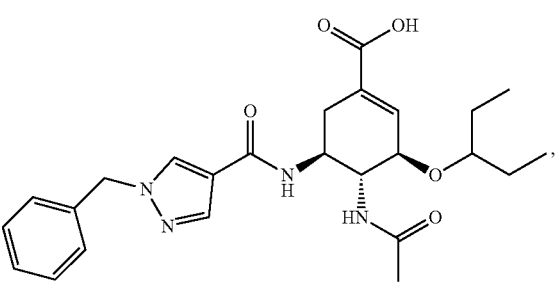
OC-002
S29
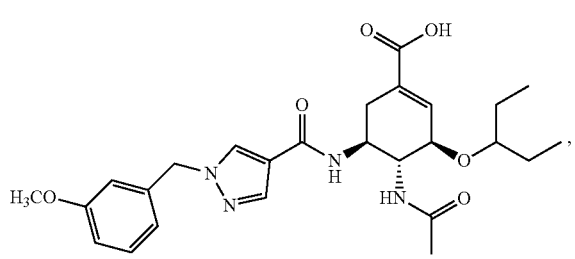
OC-003
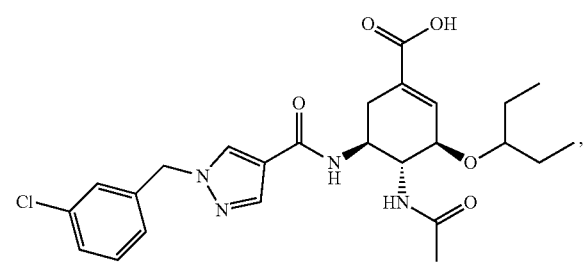

-continued
OC-004
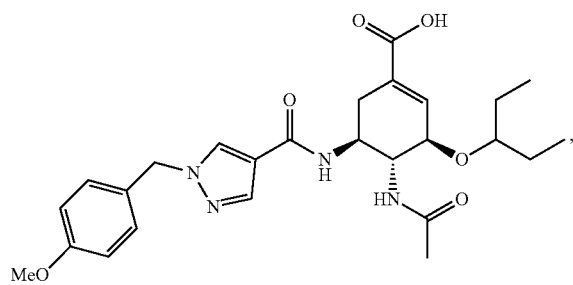
OC-005
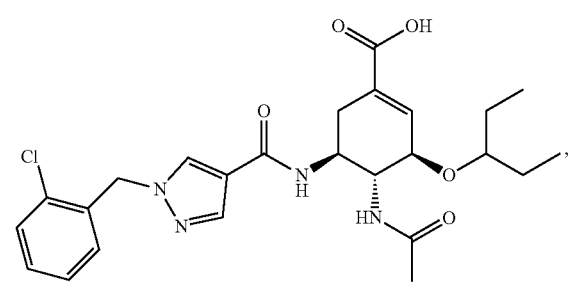
OC-006
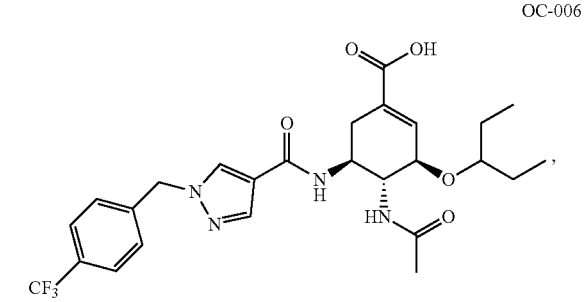
OC-007
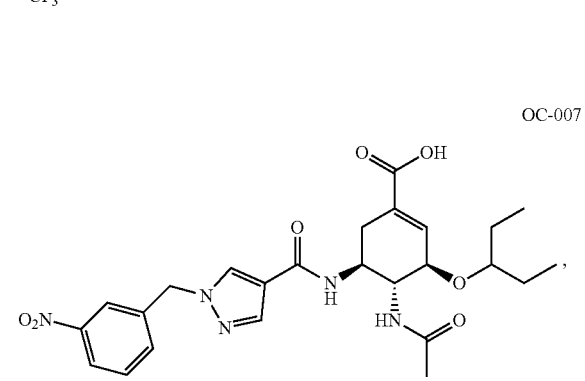
OC-008
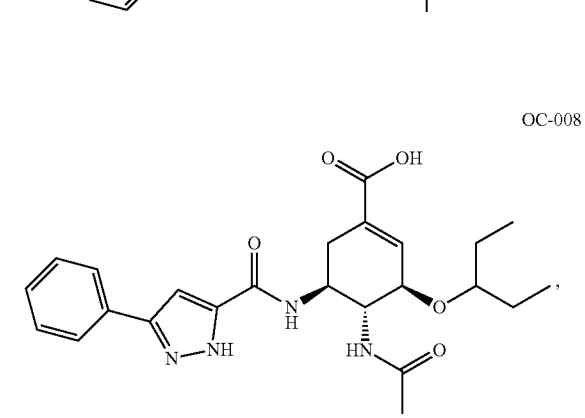
-continued
OC-009
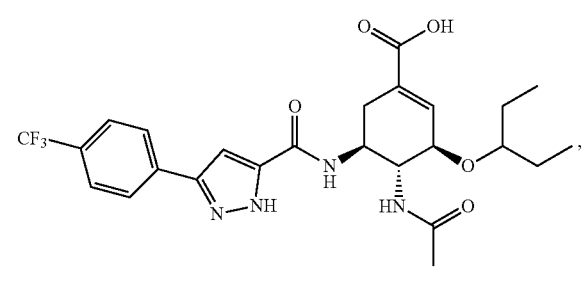
OC-010
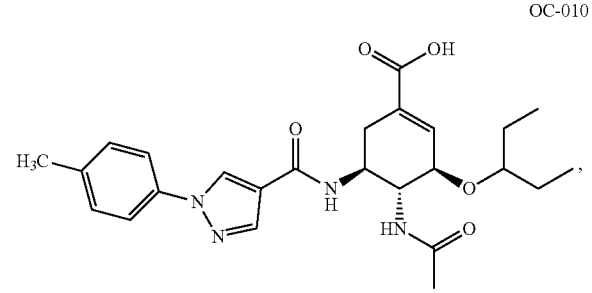
OC-011
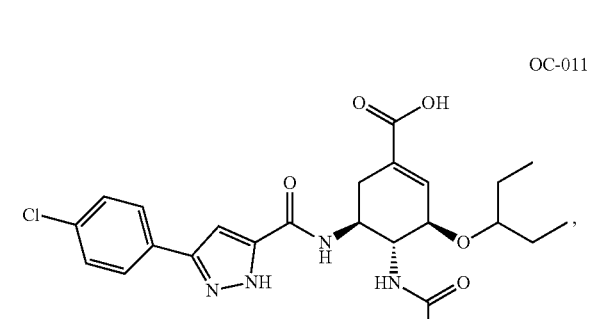
OC-012
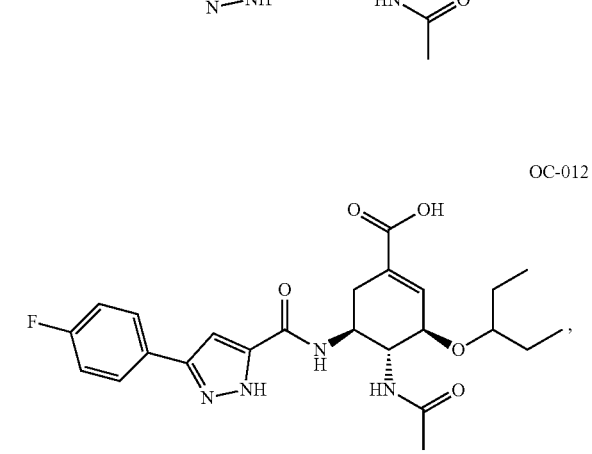
OC-013
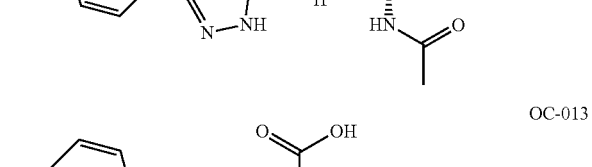
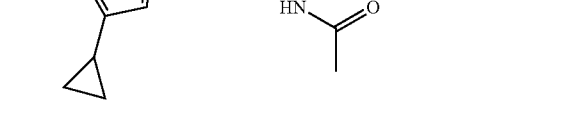

-continued
OC-014
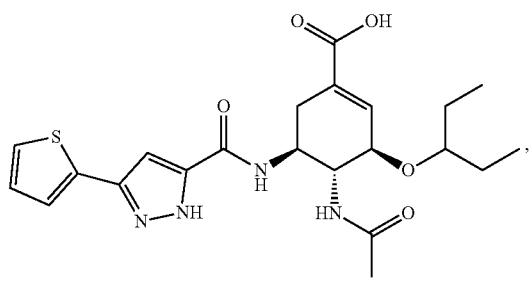
OC-015
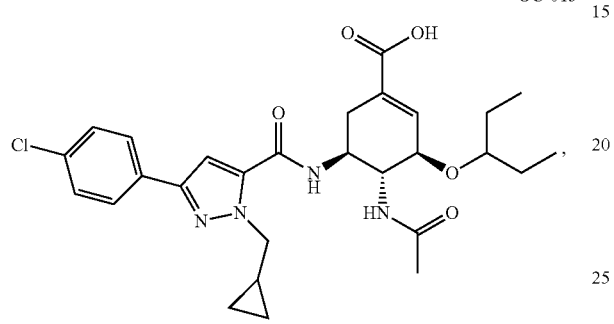
OC-016
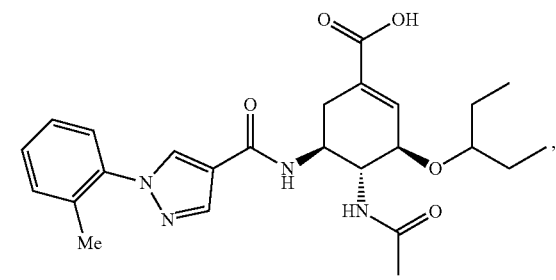
OC-017
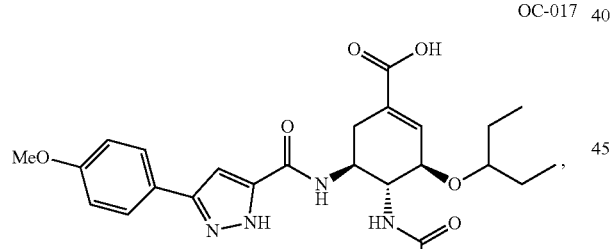
OC-018
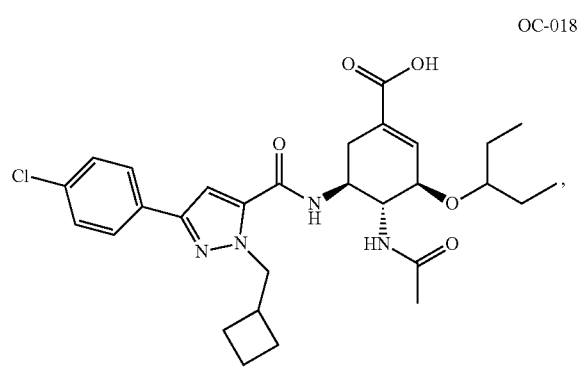
-continued
OC-0019
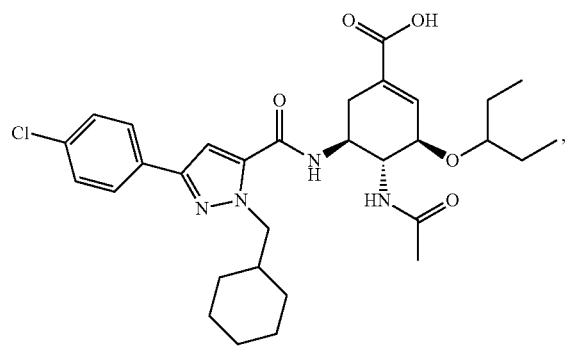
OC-0020
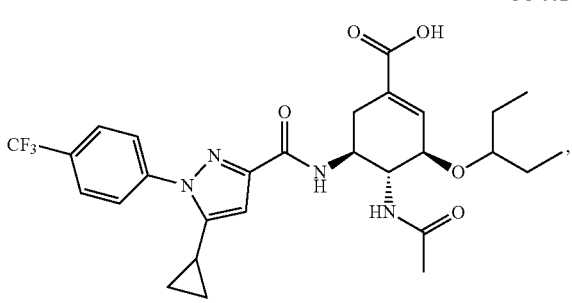
OC-0021
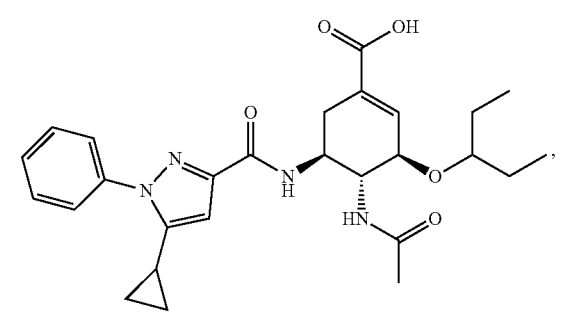
OC-022
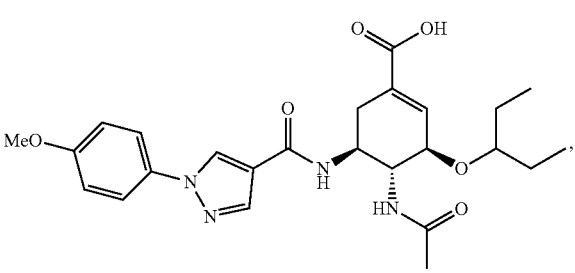
OC-023
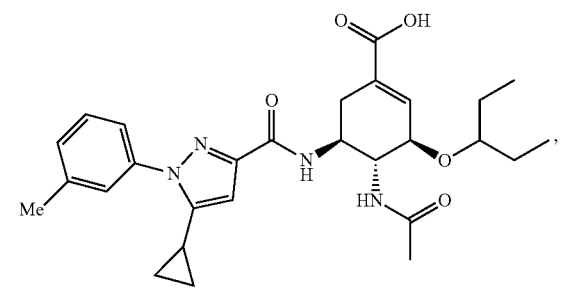

OC-024
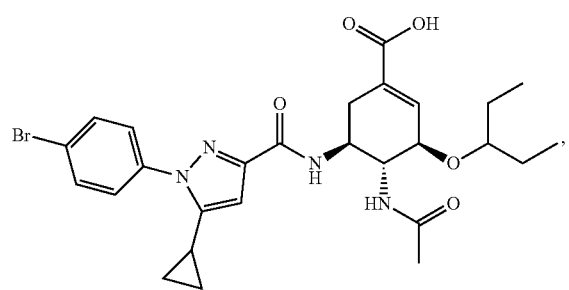
OC-025
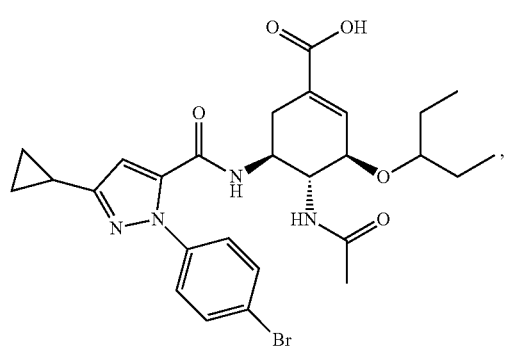
OC-026
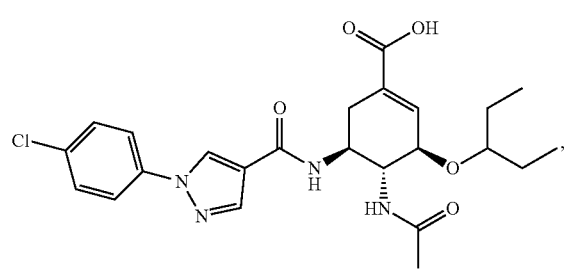
OC-027
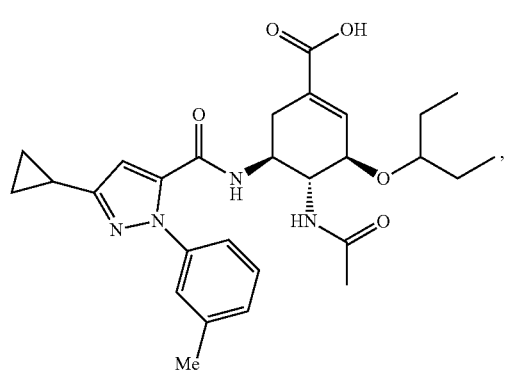
OC-028
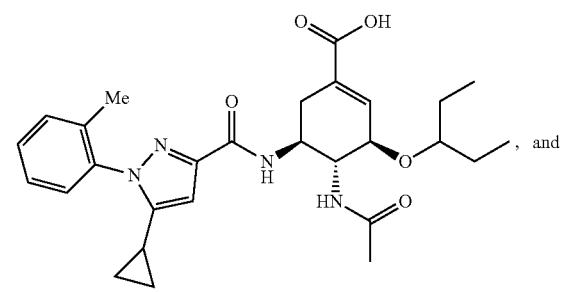, and
OC-029
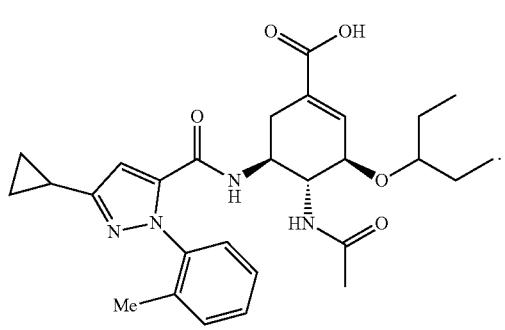
7. The compound of claim 1, wherein the compound is selected from the group consisting of:
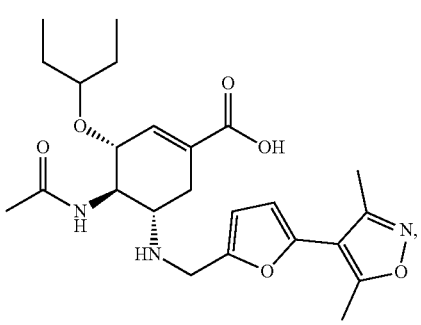
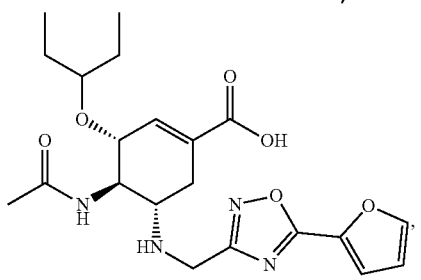
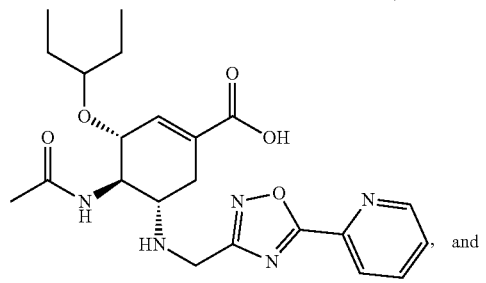, and
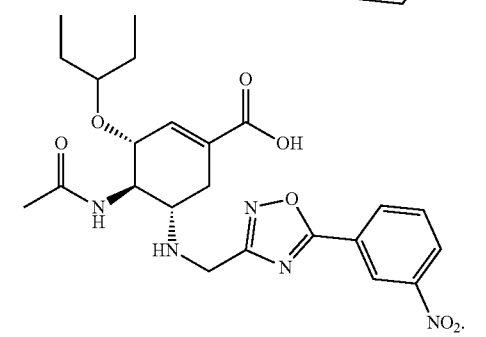

8. A pharmaceutical composition comprising a compound of claim 1 and at least one pharmaceutically acceptable carrier.

9. A method of preparing a compound of claim 1, the method comprising:

contacting a compound of Formula IV:

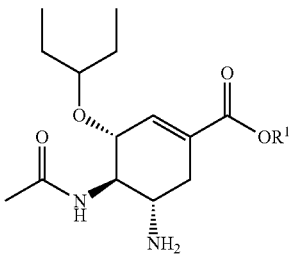

IV wherein $R^1$ is hydrogen, alkyl, alkenyl, alkynyl, cycloalkyl, heterocycloalkyl, aryl, or heteroaryl; with a compound Formula V:

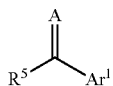

V wherein A is O; or —(C=A)- is —(CH$_2$)—; $R^5$ is a leaving group; and $Ar^1$ is selected from the group consisting of:

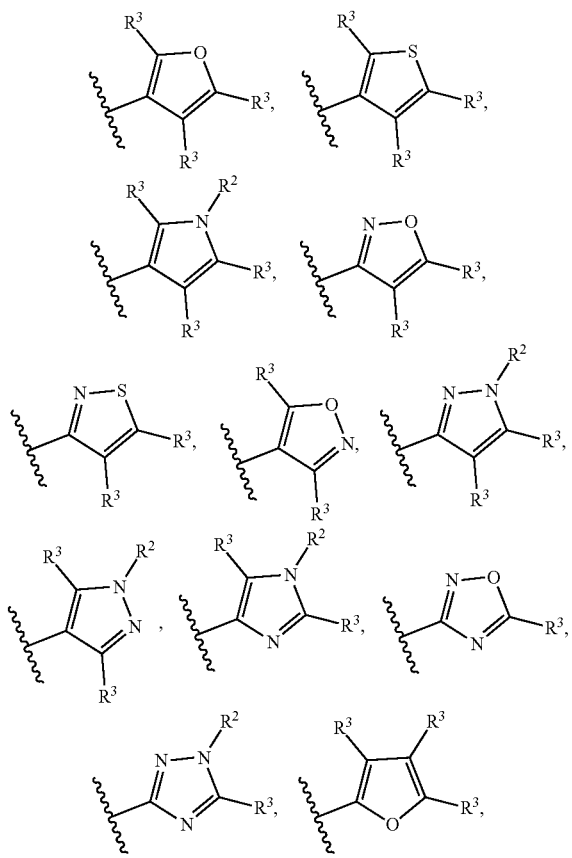

-continued

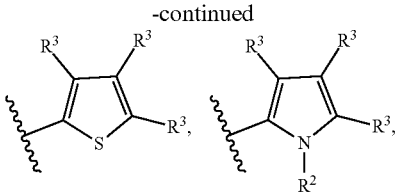

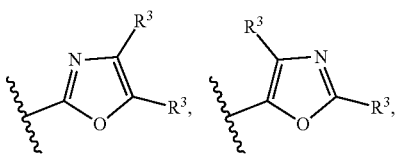

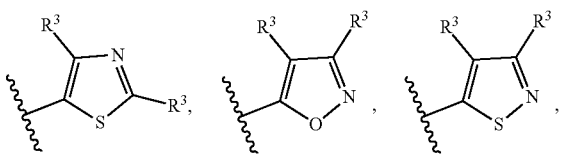

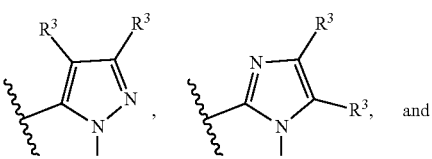

and

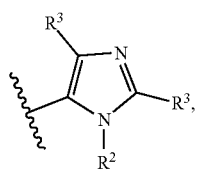

wherein $R^2$ is hydrogen, alkyl, alkenyl, alkynyl, cycloalkyl, heterocycloalkyl, aryl, aralkyl, heteroaryl, —(C=O)R, —(C=O)OR, —(C=O)NR$_2$, —(C=NR)NR$_2$, —(S=O)R, —S(O)$_2$R, —S(O)$_2$OR, —S(O)$_2$NR$_2$, —(P=O)(OR)$_2$, or —(CR$_2$)$_m$Y; and $R^3$ for each instance is independently hydrogen, alkyl, alkenyl, alkynyl, cycloalkyl, heterocycloalkyl, aryl, aralkyl, heteroaryl, OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —NR)(C=O)NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)NR$_2$, —(NR)S(O)$_2$NR$_2$, —(NR)S(O)$_2$OR, —(P=O)(OR)$_2$, halide, nitrile, nitro, or —(CR$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR$_2$, —(C=O)R, —(C=O)OR, —O(C=O)R, —O(C=O)OR, —(C=O)NR$_2$, —(NR)(C=O)R, —(NR)(C=O)OR, —O(C=O)NR$_2$, —O(C=NR)NR$_2$, —(NR)(C=O)NR$_2$, —(C=NR)NR$_2$, —(NR)(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P=O)(OR)$_2$; or contacting the compound of Formula 3 with a compound Formula VI:

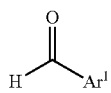

VI wherein Ar¹ is selected from the group consisting of:

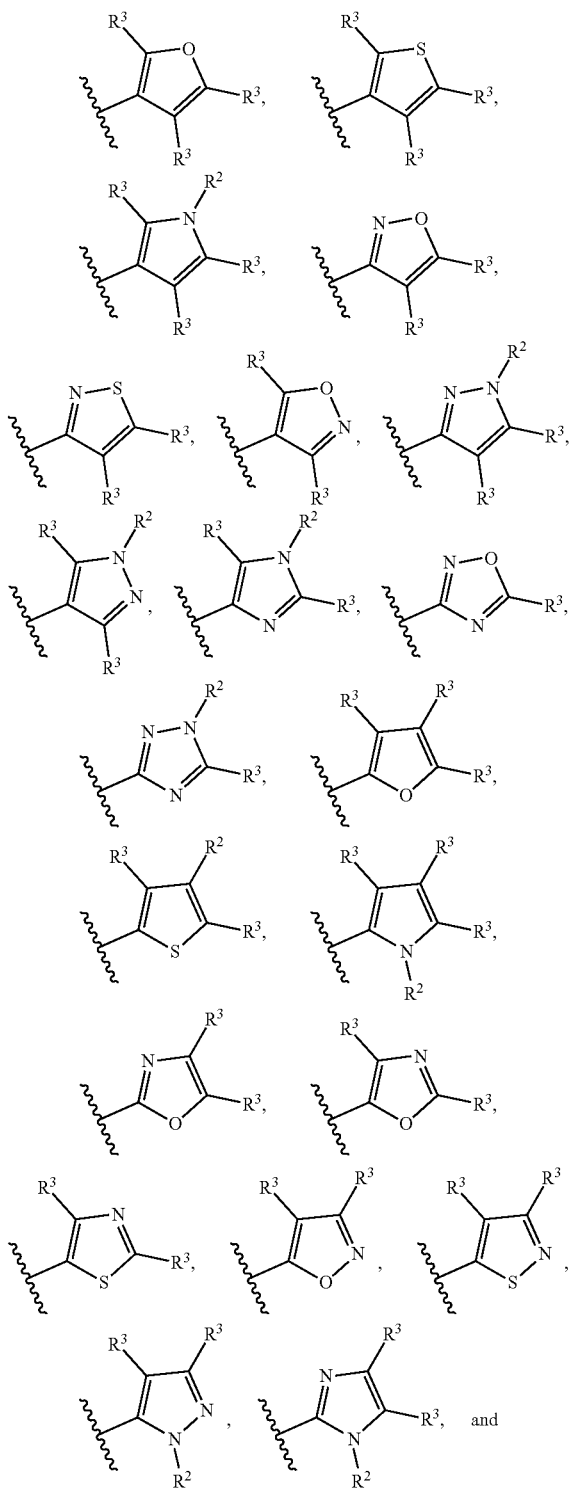

-continued

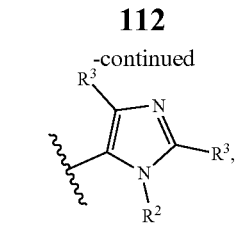

wherein $R^2$ is hydrogen, alkyl, alkenyl, alkynyl, cycloalkyl, heterocycloalkyl, aryl, aralkyl, heteroaryl, —(C═O)R, —(C═O)OR, —(C═O)NR$_2$, —(C═NR)NR$_2$, —(S═O)R, —S(O)$_2$R, —S(O)$_2$OR, —S(O)$_2$NR$_2$, —(P═O)(OR)$_2$, or —(CR$_2$)$_m$Y; and $R^3$ for each instance is independently hydrogen, alkyl, alkenyl, alkynyl, cycloalkyl, heterocycloalkyl, aryl, aralkyl, heteroaryl, OR, SR, NR$_2$, —(C═O)R, —(C═O)OR, —O(C═O)R, —O(C═O)OR, —(C═O)NR$_2$, —(NR)(C═O)R, —(NR)(C═O)OR, —O(C═O)NR$_2$, —O(C═NR)NR$_2$, —NR)(C═O)NR$_2$, —(C═NR)NR$_2$, —(NR)(C═NR)NR$_2$, —(S═O)R, —S(O)$_2$R, —S(O)$_2$OR, —S(O)$_2$NR$_2$, —OS(O)$_2$R, —(NR)S(O)$_2$R, —OS(O)$_2$OR, —OS(O)NR$_2$, —(NR)S(O)$_2$NR$_2$, —(NR)S(O)$_2$OR, —(P═O)(OR)$_2$, halide, nitrile, nitro, or —(CR$_2$)$_m$Y, wherein m for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, NR$_2$, —(C═O)R, —(C═O)OR, —O(C═O)R, —O(C═O)OR, —(C═O)NR$_2$, —(NR)(C═O)R, —(NR)(C═O)OR, —O(C═O)NR$_2$, —O(C═NR)NR$_2$, —(NR)(C═O)NR$_2$, —(C═NR)NR$_2$, —(NR)(C═NR)NR$_2$, —(S═O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P═O)(OR)$_2$; and a reducing agent; thereby forming the compound of claim 1.

10. The method of claim 9, wherein $R^5$ is a halide; and the reducing agent is NaCNBH$_3$.

11. A method of treating a viral infection in a subject in need thereof comprising the step of administering a therapeutically effective amount of the compound of claim 1 to the subject.

12. The method of claim 11, wherein the viral infection is an influenza viral infection.

13. The method of claim 11, wherein the viral infection is a H1N1 or H3N2 infection.

14. The method of claim 11, wherein the compound is selected from the group consisting of:

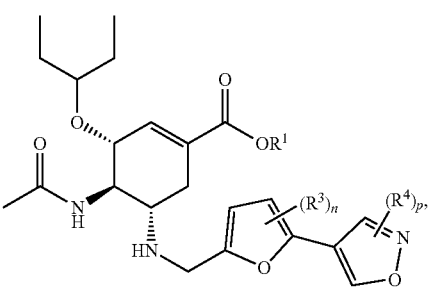

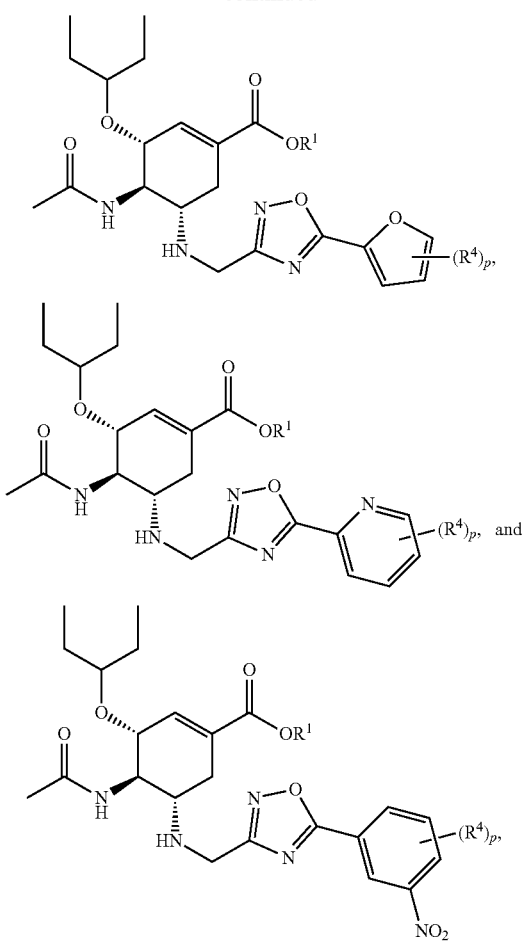

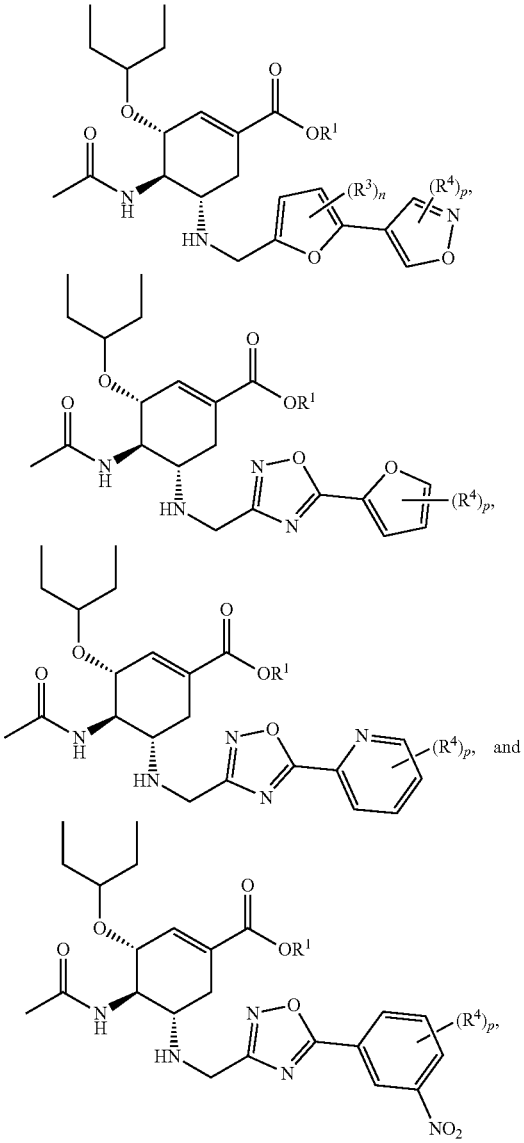

wherein n is 0, 1, or 2; p is 0, 1, or 2; and each of $R^3$ and $R^4$ for each occurrence is independently alkyl, alkenyl, alkynyl, cycloalkyl, heterocycloalkyl, aryl, aralkyl, heteroaryl, OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)(C=NR)$NR_2$, —(S=O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, —(P=O)(OR)$_2$, halide, nitrile, nitro, or —(CH$_2$)$_m$Y, wherein in for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)(C=NR)$NR_2$, —(S=O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, and —(P=O)(OR)$_2$.

15. The method of claim 13, wherein the compound is selected from the group consisting of:

wherein n is 0, 1, or 2; p is 0, 1, or 2; and each of $R^3$ and $R^4$ for each occurrence is independently alkyl, alkenyl, alkynyl, cycloalkyl, heterocycloalkyl, aryl, aralkyl, heteroaryl, OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)(C=NR)$NR_2$, —(S=O)R, —S(O)$_2$R, —S(O)$_2$OR, —S(O)$_2$$NR_2$, —OS(O)$_2$R, —(NR)S(O)$_2$R, —OS(O)$_2$OR, —OS(O)$_2$$NR_2$, —(NR)S(O)$_2$$NR_2$, —(NR)S(O)$_2$OR, —(P=O)(OR)$_2$, halide, nitrile, nitro, or —(CH$_2$)$_m$Y, wherein in for each occurrence is a whole number selected from 1-10; R for each occurrence is independently selected from the group consisting of hydrogen, alkyl, alkenyl, alkynyl, cycloalkyl, heterocycloalkyl, aryl, and heteroaryl; and Y for each occurrence is selected from the group consisting of OR, SR, $NR_2$, —(C=O)R, —(C=O)OR, —O(C=O)R, —O(C=O)OR, —(C=O)$NR_2$, —(NR)(C=O)R, —(NR)(C=O)OR, —O(C=O)$NR_2$, —O(C=NR)$NR_2$, —(NR)(C=O)$NR_2$, —(C=NR)$NR_2$, —(NR)

(C=NR)NR$_2$, —(S=O)R, —S(O)$_2$R, —S(O)$_2$OR, —S(O)$_2$NR$_2$, —OS(O)$_2$R, —(NR)S(O)$_2$R, —OS(O)$_2$OR, —OS(O)$_2$NR$_2$, —(NR)S(O)$_2$NR$_2$, —(NR)S(O)$_2$OR, and —(P=O)(OR)$_2$.

* * * * *